(12) United States Patent
Stamos et al.

(10) Patent No.: US 8,841,282 B2
(45) Date of Patent: Sep. 23, 2014

(54) PYRROLIDINONE BENZENESULFONAMIDE DERIVATIVES AS MODULATORS OF ION CHANNELS

(71) Applicant: Vertex Pharmaceuticals Incorporated, Cambridge, MA (US)

(72) Inventors: Dean Stamos, Carlsbad, CA (US); Esther Ann Martinborough, San Diego, CA (US); Nicole Hilgraf, San Diego, CA (US); Timothy Donald Neubert, San Diego, CA (US); Mehdi Numa, San Diego, CA (US); Tara Whitney, Carlsbad, CA (US); Aarti Sameer Kawatkar, Newton, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 13/967,732

(22) Filed: Aug. 15, 2013

(65) Prior Publication Data

US 2013/0338119 A1 Dec. 19, 2013

Related U.S. Application Data

(62) Division of application No. 13/178,877, filed on Jul. 8, 2011, which is a division of application No. 12/269,108, filed on Nov. 12, 2008, now Pat. No. 7,994,166.

(60) Provisional application No. 61/088,141, filed on Aug. 12, 2008, provisional application No. 60/987,485, filed on Nov. 13, 2007.

(51) Int. Cl.
  *C07D 417/14* (2006.01)

(52) U.S. Cl.
  CPC .................................. *C07D 417/14* (2013.01)
  USPC ........................................................ 514/158

(58) Field of Classification Search
  None
  See application file for complete search history.

(56) References Cited

U.S. PATENT DOCUMENTS

| | | | |
|---|---|---|---|
| 7,605,174 B2 | 10/2009 | Neubert et al. |
| 7,615,563 B2 | 11/2009 | Gonzalez, III et al. |
| 7,683,066 B2 | 3/2010 | Termin et al. |
| 7,683,083 B2 | 3/2010 | Martinborough et al. |
| 7,745,629 B2 | 6/2010 | Termin et al. |
| 7,786,137 B2 | 8/2010 | Kawatkar et al. |
| 7,799,822 B2 | 9/2010 | Martinborough et al. |
| 7,842,819 B2 | 11/2010 | Martinborough et al. |
| 7,846,954 B2 | 12/2010 | Zimmermann et al. |
| 7,855,220 B2 | 12/2010 | Neubert et al. |
| 7,989,481 B2 | 8/2011 | Neubert et al. |
| 7,994,166 B2 | 8/2011 | Stamos et al. |
| 7,994,174 B2 | 8/2011 | Martinborough et al. |
| 8,097,636 B2 | 1/2012 | Stamos et al. |
| 8,129,546 B2 | 3/2012 | Martinborough et al. |
| 8,143,297 B2 | 3/2012 | Hilgraf et al. |
| 8,153,655 B2 | 4/2012 | Gonzalez, III et al. |
| 8,163,720 B2 | 4/2012 | Martinborough et al. |
| 8,193,194 B2 | 6/2012 | Martinborough et al. |
| 8,202,861 B2 | 6/2012 | Gonzales, III et al. |
| 8,236,829 B2 | 8/2012 | Neubert et al. |
| 8,236,833 B2 | 8/2012 | Martinborough et al. |
| 8,309,543 B2 | 11/2012 | Gonzalez, III et al. |
| 8,309,587 B2 | 11/2012 | Martinborough et al. |
| 8,314,125 B2 | 11/2012 | Termin et al. |
| 8,343,763 B2 | 1/2013 | Hilgraf et al. |
| 8,357,702 B2 | 1/2013 | Neubert et al. |
| 8,362,032 B2 | 1/2013 | Kawatkar et al. |
| 8,372,843 B2 | 2/2013 | Termin et al. |
| 8,492,403 B2 | 7/2013 | Kawatkar et al. |
| 2012/0010416 A1 | 1/2012 | Stamos et al. |
| 2012/0208790 A1 | 8/2012 | Martinborough et al. |
| 2013/0035310 A1 | 2/2013 | Martinborough et al. |
| 2013/0084639 A1 | 4/2013 | Termin et al. |
| 2013/0184258 A1 | 7/2013 | Gonzalez, III et al. |

OTHER PUBLICATIONS

Horig et al., Journal of Translational Medicine 2004, 2(44).*
Medicines in Development for Mental Illnesses 2010.*
Sabido-David et al., Expert Opin. Investig. Drugs 2004, 13(10), 1249-1261.*
Schafer et al. Drug Discovery Today 2008, 13 (21/22), 913-916.*

* cited by examiner

*Primary Examiner* — Alicia L Otton
(74) *Attorney, Agent, or Firm* — Michael J. DiVerdi

(57) ABSTRACT

The present invention relates to pyrrolidinone benzenesulfonamides of the following formula:

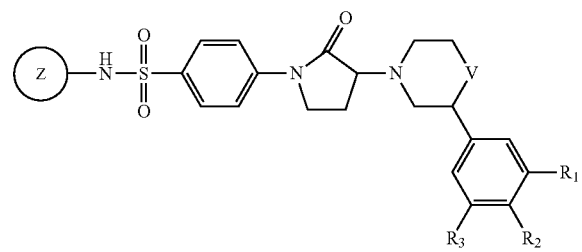

useful as inhibitors of ion channels. The invention also provides pharmaceutically acceptable compositions comprising the compounds of the invention and methods of using the compositions in the treatment of various disorders, such as pain.

26 Claims, No Drawings

PYRROLIDINONE BENZENESULFONAMIDE DERIVATIVES AS MODULATORS OF ION CHANNELS

CROSS REFERENCE TO RELATED APPLICATIONS

This application is a divisional of U.S. patent application Ser. No. 13/178,877, filed Jul. 8, 2011, which is a divisional of U.S. patent application Ser. No. 12/269,108, now U.S. Pat. No. 7,994,166, filed Nov. 12, 2008, which claims the benefit of priority to U.S. provisional patent application Ser. Nos. 60/987,485, filed Nov. 13, 2007, and 61/088,141, filed Aug. 12, 2008, the contents of all applications are incorporated herein by reference.

TECHNICAL FIELD OF THE INVENTION

The present invention relates to compounds useful as inhibitors of ion channels. The invention also provides pharmaceutically acceptable compositions comprising the compounds of the invention and methods of using the compositions in the treatment of various disorders.

BACKGROUND OF THE INVENTION

Na channels are central to the generation of action potentials in all excitable cells such as neurons and myocytes. They play key roles in excitable tissue including brain, smooth muscles of the gastrointestinal tract, skeletal muscle, the peripheral nervous system, spinal cord and airway. As such they play key roles in a variety of disease states such as epilepsy (See, Moulard, B. and D. Bertrand (2002) "Epilepsy and sodium channel blockers" *Expert Opin. Ther. Patents* 12(1): 85-91)), pain (See, Waxman, S. G., S. Dib-Hajj, et al. (1999) "Sodium channels and pain" *Proc Natl Acad Sci USA* 96(14): 7635-9 and Waxman, S. G., T. R. Cummins, et al. (2000) "Voltage-gated sodium channels and the molecular pathogenesis of pain: a review" *J Rehabil Res Dev* 37(5): 517-28), myotonia (See, Meola, G. and V. Sansone (2000) "Therapy in myotonic disorders and in muscle channelopathies" *Neurol Sci* 21(5): S953-61 and Mankodi, A. and C. A. Thornton (2002) "Myotonic syndromes" *Curr Opin Neurol* 15(5): 545-52), ataxia (See, Meisler, M. H., J. A. Kearney, et al. (2002) "Mutations of voltage-gated sodium channels in movement disorders and epilepsy" *Novartis Found Symp* 241: 72-81), multiple sclerosis (See, Black, J. A., S. Dib-Hajj, et al. (2000) "Sensory neuron-specific sodium channel SNS is abnormally expressed in the brains of mice with experimental allergic encephalomyelitis and humans with multiple sclerosis" *Proc Natl Acad Sci USA* 97(21): 11598-602, and Renganathan, M., M. Gelderblom, et al. (2003) "Expression of Na(v)1.8 sodium channels perturbs the firing patterns of cerebellar purkinje cells" *Brain Res* 959(2): 235-42), irritable bowel (See, Su, X., R. E. Wachtel, et al. (1999) "Capsaicin sensitivity and voltage-gated sodium currents in colon sensory neurons from rat dorsal root ganglia" *Am J Physiol* 277(6 Pt 1): G1180-8, and Laird, J. M., V. Souslova, et al. (2002) "Deficits in visceral pain and referred hyperalgesia in Nav1.8 (SNS/PN3)-null mice" *J Neurosci* 22(19): 8352-6), urinary incontinence and visceral pain (See, Yoshimura, N., S. Seki, et al. (2001) "The involvement of the tetrodotoxin-resistant sodium channel Na(v)1.8 (PN3/SNS) in a rat model of visceral pain" *J Neurosci* 21(21): 8690-6), as well as an array of psychiatry dysfunctions such as anxiety and depression (See, Hurley, S. C. (2002) "Lamotrigine update and its use in mood disorders" *Ann Pharmacother* 36(5): 860-73).

Voltage gated Na channels comprise a gene family consisting of 9 different subtypes (NaV1.1-NaV1.9). As shown in Table 1, these subtypes show tissue specific localization and functional differences (See, Goldin, A. L. (2001) "Resurgence of sodium channel research" *Annu Rev Physiol* 63: 871-94). Three members of the gene family (NaV1.8, 1.9, 1.5) are resistant to block by the well-known Na channel blocker TTX, demonstrating subtype specificity within this gene family. Mutational analysis has identified glutamate 387 as a critical residue for TTX binding (See, Noda, M., H. Suzuki, et al. (1989) "A single point mutation confers tetrodotoxin and saxitoxin insensitivity on the sodium channel II" *FEBS Lett* 259(1): 213-6).

TABLE 1

| Na isoform | Tissue | TTX IC50 | Indications |
|---|---|---|---|
| NaV1.1 | CNS, PNS soma of neurons | 10 nM | Pain, Epilepsy, neurodegeneration |
| NaV1.2 | CNS, high in axons | 10 nM | Neurodegeneration Epilepsy |
| NaV1.3 | CNS, embryonic, injured nerves | 15 nM | Pain |
| NaV1.4 | Skeletal muscle | 25 nM | Myotonia |
| NaV1.5 | Heart | 2 µM | Arrhythmia, long QT |
| NaV1.6 | CNS widespread, most abundant | 6 nM | Pain, movement disorders |
| NaV1.7 | PNS, DRG, terminals neuroendocrine | 25 nM | Pain, Neuroendocrine disorders |
| NaV1.8 | PNS, small neurons in DRG & TG | >50 µM | Pain |
| NaV1.9 | PNS, small neurons in DRG & TG | 1 µM | Pain |

(Abbreviations: CNS = central nervous system, PNS = peripherial nervous system, DRG = dorsal root ganglion, TG = Trigeminal ganglion):

In general, voltage-gated sodium channels (NaVs) are responsible for initiating the rapid upstroke of action potentials in excitable tissue in nervous system, which transmit the electrical signals that compose and encode normal and aberrant pain sensations. Antagonists of NaV channels can attenuate these pain signals and are useful for treating a variety of pain conditions, including but not limited to acute, chronic, inflammatory, and neuropathic pain. Known NaV antagonists, such as TTX, lidocaine (See, Mao, J. and L. L. Chen (2000) "Systemic lidocaine for neuropathic pain relief" *Pain* 87(1): 7-17.) bupivacaine, phenyloin (See, Jensen, T. S. (2002) "Anticonvulsants in neuropathic pain: rationale and clinical evidence" *Eur J Pain* 6 (Suppl A): 61-8), lamotrigine (See, Rozen, T. D. (2001) "Antiepileptic drugs in the management of cluster headache and trigeminal neuralgia" *Headache* 41 Suppl 1: S25-32 and Jensen, T. S. (2002) "Anticonvulsants in neuropathic pain: rationale and clinical evidence" *Eur J Pain* 6 (Suppl A): 61-8.), and carbamazepine (See, Backonja, M. M. (2002) "Use of anticonvulsants for treatment of neuropathic pain" *Neurology* 59(5 Suppl 2): S14-7), have been shown to be useful attenuating pain in humans and animal models.

Hyperalgesia (extreme sensitivity to something painful) that develops in the presence of tissue injury or inflammation reflects, at least in part, an increase in the excitability of high-threshold primary afferent neurons innervating the site of injury. Voltage sensitive sodium channels activation is critical for the generation and propagation of neuronal action potentials. There is a growing body of evidence indicating that modulation of NaV currents is an endogenous mechanism used to control neuronal excitability (See, Goldin, A. L. (2001) "Resurgence of sodium channel research" *Annu Rev Physiol* 63: 871-94). Several kinetically and pharmacologically distinct voltage-gated sodium channels are found in dorsal root ganglion (DRG) neurons. The TTX-resistant current is insensitive to micromolar concentrations of tetrodotoxin, and displays slow activation and inactivation kinetics and a more depolarized activation threshold when compared to other voltage-gated sodium channels. TTX-resistant sodium currents are primarily restricted to a subpopulation of sensory neurons likely to be involved in nociception. Specifically, TTX-resistant sodium currents are expressed almost exclusively in neurons that have a small cell-body diameter; and give rise to small-diameter slow-conducting axons and that are responsive to capsaicin. A large body of experimental evidence demonstrates that TTX-resistant sodium channels are expressed on C-fibers and are important in the transmission of nociceptive information to the spinal cord.

Intrathecal administration of antisense oligo-deoxynucleotides targeting a unique region of the TTX-resistant sodium channel (NaV1.8) resulted in a significant reduction in $PGE_2$-induced hyperalgesia (See, Khasar, S. G., M. S. Gold, et al. (1998) "A tetrodotoxin-resistant sodium current mediates inflammatory pain in the rat" *Neurosci Lett* 256(1): 17-20). More recently, a knockout mouse line was generated by Wood and colleagues, which lacks functional NaV1.8. The mutation has an analgesic effect in tests assessing the animal's response to the inflammatory agent carrageenan (See, Akopian, A. N., V. Souslova, et al. (1999) "The tetrodotoxin-resistant sodium channel SNS has a specialized function in pain pathways" *Nat Neurosci* 2(6): 541-8.). In addition, deficit in both mechano- and thermoreception were observed in these animals. The analgesia shown by the Nav1.8 knockout mutants is consistent with observations about the role of TTX-resistant currents in nociception.

Immunohistochemical, in-situ hybridization and in-vitro electrophysiology experiments have all shown that the sodium channel NaV1.8 is selectively localized to the small sensory neurons of the dorsal root ganglion and trigeminal ganglion (See, Akopian, A. N., L. Sivilotti, et al. (1996) "A tetrodotoxin-resistant voltage-gated sodium channel expressed by sensory neurons" *Nature* 379(6562): 257-62.). The primary role of these neurons is the detection and transmission of nociceptive stimuli. Antisense and immunohistochemical evidence also supports a role for NaV1.8 in neuropathic pain (See, Lai, J., M. S. Gold, et al. (2002) "Inhibition of neuropathic pain by decreased expression of the tetrodotoxin-resistant sodium channel, NaV1.8" *Pain* 95(1-2): 143-52, and Lai, J., J. C. Hunter, et al. (2000) "Blockade of neuropathic pain by antisense targeting of tetrodotoxin-resistant sodium channels in sensory neurons" *Methods Enzymol* 314: 201-13.). NaV1.8 protein is upregulated along uninjured C-fibers adjacent to the nerve injury. Antisense treatment prevents the redistribution of NaV1.8 along the nerve and reverses neuropathic pain. Taken together the gene-knockout and antisense data support a role for NaV1.8 in the detection and transmission of inflammatory and neuropathic pain.

In neuropathic pain states there is a remodeling of Na channel distribution and subtype. In the injured nerve, expression of NaV1.8 and NaV1.9 are greatly reduced whereas expression of the TTX sensitive subunit NaV1.3 is 5-10 fold upregulated (See, Dib-Hajj, S. D., J. Fjell, et al. (1999) "Plasticity of sodium channel expression in DRG neurons in the chronic constriction injury model of neuropathic pain." *Pain* 83(3): 591-600.) The timecourse of the increase in NaV1.3 parallels the appearance of allodynia in animal models subsequent to nerve injury. The biophysics of the NaV1.3 channel is distinctive in that it shows very fast repriming after inactivation following an action potential. This allows for sustained rates of high firing as is often seen in the injured nerve (See, Cummins, T. R., F. Aglieco, et al. (2001) "Nav1.3 sodium channels: rapid repriming and slow closed-state inactivation display quantitative differences after expression in a mammalian cell line and in spinal sensory neurons" *J Neurosci* 21(16): 5952-61.). NaV1.3 is expressed in the central and peripheral systems of man. NaV1.9 is similar to NaV1.8 as it is selectively localized to small sensory neurons of the dorsal root ganglion and trigeminal ganglion (See, Fang, X., L. Djouhri, et al. (2002). "The presence and role of the tetrodotoxin-resistant sodium channel Na(v)1.9 (NaN) in nociceptive primary afferent neurons." *J Neurosci* 22(17): 7425-33.). It has a slow rate of inactivation and left-shifted voltage dependence for activation (See, Dib-Hajj, S., J. A. Black, et al. (2002) "NaN/Nav1.9: a sodium channel with unique properties" *Trends Neurosci* 25(5): 253-9.). These two biophysical properties allow NaV1.9 to play a role in establishing the resting membrane potential of nociceptive neurons. The resting membrane potential of NaV1.9 expressing cells is in the −55 to −50 mV range compared to −65 mV for most other peripheral and central neurons. This persistent depolarization is in large part due to the sustained low-level activation of NaV1.9 channels. This depolarization allows the neurons to more easily reach the threshold for firing action potentials in response to nociceptive stimuli. Compounds that block the NaV1.9 channel may play an important role in establishing the set point for detection of painful stimuli. In chronic pain states, nerve and nerve ending can become swollen and hypersensitive exhibiting high frequency action potential firing with mild or even no stimulation. These pathologic nerve swellings are termed neuromas and the primary Na channels expressed in them are NaV1.8 and NaV1.7 (See, Kretschmer, T., L. T. Happel, et al. (2002) "Accumulation of PN1 and PN3 sodium channels in painful human neuroma-evidence from immunocytochemistry" *Acta Neurochir (Wien)* 144(8): 803-10; discussion 810.). NaV1.6 and NaV1.7 are also expressed in dorsal root ganglion neurons and contribute to the small TTX sensitive component seen in these cells. NaV1.7 in particular may therefore be a potential pain target in addition to it's role in neuroendocrine excitability (See, Klugbauer, N., L. Lacinova, et al. (1995) "Structure and functional expression of a new member of the tetrodotoxin-sensitive voltage-activated sodium channel family from human neuroendocrine cells" *Embo J* 14(6): 1084-90).

NaV1.1 (See, Sugawara, T., E. Mazaki-Miyazaki, et al. (2001) "Nav1.1 mutations cause febrile seizures associated with afebrile partial seizures." *Neurology* 57(4): 703-5.) and NaV1.2 (See, Sugawara, T., Y. Tsurubuchi, et al. (2001) "A missense mutation of the Na+ channel alpha II subunit gene Na(v)1.2 in a patient with febrile and afebrile seizures causes channel dysfunction" *Proc Natl Acad Sci USA* 98(11): 6384-9) have been linked to epilepsy conditions including febrile seizures. There are over 9 genetic mutations in NaV1.1 associated with febrile seizures (See, Meisler, M. H., J. A. Kearney, et al. (2002) "Mutations of voltage-gated sodium channels in movement disorders and epilepsy" *Novartis Found Symp* 241: 72-81)

Antagonists for NaV1.5 have been developed and used to treat cardiac arrhythmias. A gene defect in NaV1.5 that produces a larger noninactivating component to the current has been linked to long QT in man and the orally available local anesthetic mexilitine has been used to treat this condition (See, Wang, D. W., K. Yazawa, et al. (1997) "Pharmacological targeting of long QT mutant sodium channels." *J Clin Invest* 99(7): 1714-20).

Several Na channel blockers are currently used or being tested in the clinic to treat epilepsy (See, Moulard, B. and D. Bertrand (2002) "Epilepsy and sodium channel blockers" *Expert Opin. Ther. Patents* 12(1): 85-91.); acute (See, Wiffen, P., S. Collins, et al. (2000) "Anticonvulsant drugs for acute and chronic pain" *Cochrane Database Syst Rev* 3), chronic (See, Wiffen, P., S. Collins, et al. (2000) "Anticonvulsant drugs for acute and chronic pain" *Cochrane Database Syst Rev* 3, and Guay, D. R. (2001) "Adjunctive agents in the management of chronic pain" *Pharmacotherapy* 21(9): 1070-81), inflammatory (See, Gold, M. S. (1999) "Tetrodotoxin-resistant Na+ currents and inflammatory hyperalgesia." *Proc Natl Acad Sci USA* 96(14): 7645-9), and neuropathic pain (See, Strichartz, G. R., Z. Zhou, et al. (2002) "Therapeutic concentrations of local anaesthetics unveil the potential role of sodium channels in neuropathic pain" *Novartis Found Symp* 241: 189-201, and Sandner-Kiesling, A., G. Rumpold Seitlinger, et al. (2002) "Lamotrigine monotherapy for control of neuralgia after nerve section" *Acta Anaesthesiol Scand* 46(10): 1261-4); cardiac arrhythmias (See, An, R. H., R. Bangalore, et al. (1996) "Lidocaine block of LQT-3 mutant human Na+ channels" *Circ Res* 79(1): 103-8, and Wang, D. W., K. Yazawa, et al. (1997) "Pharmacological targeting of long QT mutant sodium channels" *J Clin Invest* 99(7): 1714-20); neuroprotection (See, Taylor, C. P. and L. S. Narasimhan (1997) "Sodium channels and therapy of central nervous system diseases" *Adv Pharmacol* 39: 47-98) and as anesthetics (See, Strichartz, G. R., Z. Zhou, et al. (2002) "Therapeutic concentrations of local anaesthetics unveil the potential role of sodium channels in neuropathic pain" *Novartis Found Symp* 241: 189-201).

Various animal models with clinical significance have been developed for the study of sodium channel modulators for numerous different pain indications. E.g., malignant chronic pain, see, Kohase, H., et al., Acta Anaesthesiol Scand. 2004; 48(3):382-3; femur cancer pain (see, Kohase, H., et al., Acta Anaesthesiol Scand. 2004; 48(3):382-3; non-malignant chronic bone pain (see, Ciocon, J. O. et al., J Am Geriatr Soc. 1994; 42(6):593-6); rheumatoid arthritis (see, Calvino, B. et al., Behav Brain Res. 1987; 24(1):11-29); osteoarthritis (see, Guzman, R. E., et al., Toxicol Pathol. 2003; 31(6):619-24); spinal stenosis (see, Takenobu, Y. et al., J Neurosci Methods. 2001; 104(2):191-8); Neuropathic low back pain (see, Hines, R., et al., Pain Med. 2002; 3(4):361-5; Massie, J. B., et al., J Neurosci Methods. 2004; 137(2):283-9; neuropathic low back pain (see, Hines, R., et al., Pain Med. 2002; 3(4):361-5; Massie, J. B., et al., J Neurosci Methods. 2004; 137(2):283-9); myofascial pain syndrome (see, Dalpiaz & Dodds, J Pain Palliat Care Pharmacother. 2002; 16(1):99-104; Sluka K A et al., Muscle Nerve. 2001; 24(1):37-46); fibromyalgia (see, Bennet & Tai, Int J Clin Pharmacol Res. 1995; 15(3):115-9); temporomandibular joint pain (see, Ime H, Ren K, Brain Res Mol Brain Res. 1999; 67(1):87-97); chronic visceral pain, including, abdominal (see, Al-Chaer, E. D., et al., Gastroenterology. 2000; 119(5):1276-85); pelvic/perineal pain, (see, Wesselmann et al., Neurosci Lett. 1998; 246(2):73-6); pancreatic (see, Vera-Portocarrero, L. B., et al., Anesthesiology. 2003; 98(2):474-84); IBS pain (see, Verne, G. N., et al., Pain. 2003; 105(1-2):223-30; La J H et al., World Gastroenterol. 2003; 9(12):2791-5); chronic headache pain (see, Willimas & Stark, Cephalalgia. 2003; 23(10):963-71); migraine (see, Yamamura, H., et al., J Neurophysiol. 1999; 81(2):479-93); tension headache, including, cluster headaches (see, Costa, A., et al., Cephalalgia. 2000; 20(2):85-91); chronic neuropathic pain, including, post-herpetic neuralgia (see, Attal, N., et al., Neurology. 2004; 62(2):218-25; Kim & Chung 1992, Pain 50:355); diabetic neuropathy (see, Beidoun A et al., Clin J Pain. 2004; 20(3):174-8; Courteix, C., et al., Pain. 1993; 53(1):81-8); HIV-associated neuropathy (see, Portegies & Rosenberg, Ned Tijdschr Geneeskd. 2001; 145(15):731-5; Joseph E K et al., Pain. 2004; 107(1-2):147-58; Oh, S. B., et al., J Neurosci. 2001; 21(14):5027-35); trigeminal neuralgia (see, Sato, J., et al., Oral Surg Oral Med Oral Pathol Oral Radiol Endod. 2004; 97(1):18-22; Imamura Y et al., Exp Brain Res. 1997; 116(1):97-103); Charcot-Marie Tooth neuropathy (see, Sereda, M., et al., Neuron. 1996; 16(5):1049-60); hereditary sensory neuropathies (see, Lee, M. J., et al., Hum Mol Genet. 2003; 12(15):1917-25); peripheral nerve injury (see, Attal, N., et al., Neurology. 2004; 62(2):218-25; Kim & Chung 1992, Pain 50:355; Bennett & Xie, 1988, Pain 33:87; Decostered, I. & Woolf, C. J., 2000, Pain 87:149; Shir, Y. & Seltzer, Z. 1990; Neurosci Lett 115:62); painful neuromas (see, Nahabedian & Johnson, Ann Plast Surg. 2001; 46(1):15-22; Devor & Raber, Behav Neural Biol. 1983; 37(2):276-83); ectopic proximal and distal discharges (see, Liu, X. et al., Brain Res. 2001; 900(1):119-27); radiculopathy (see, Devers & Galer, Clin J Pain. 2000; 16(3):205-8; Hayashi N et al., Spine. 1998; 23(8):877-85); chemotherapy induced neuropathic pain (see, Aley, K. O., et al., Neuroscience. 1996; 73(1):259-65); radiotherapy-induced neuropathic pain; post-mastectomy pain (see, Devers & Galer, Clin J Pain. 2000; 16(3):205-8); central pain (Cahana, A., et al., Anesth Analg. 2004; 98(6):1581-4), spinal cord injury pain (see, Hains, B. C., et al., Exp Neurol. 2000; 164(2):426-37); post-stroke pain; thalamic pain (see, LaBuda, C. J., et al., Neurosci Lett. 2000; 290(1):79-83); complex regional pain syndrome (see, Wallace, M. S., et al., Anesthesiology. 2000; 92(1):75-83; Xantos D et al., J Pain. 2004; 5(3 Suppl 2):S1); phantom pain (see, Weber, W. E., Ned Tijdschr Geneeskd. 2001; 145(17):813-7; Levitt & Heyback, Pain. 1981; 10(1): 67-73); intractable pain (see, Yokoyama, M., et al., Can J Anaesth. 2002; 49(8):810-3); acute pain, acute post-operative pain (see, Koppert, W., et al., Anesth Analg. 2004; 98(4): 1050-5; Brennan, T. J., et al., Pain. 1996; 64(3):493-501); acute musculoskeletal pain; joint pain (see, Gotoh, S., et al., Ann Rheum Dis. 1993; 52(11):817-22); mechanical low back pain (see, Kehl, L. J., et al., Pain. 2000; 85(3):333-43); neck pain; tendonitis; injury/exercise pain (see, Sesay, M., et al., Can J Anaesth. 2002; 49(2):137-43); acute visceral pain, including, abdominal pain; pyelonephritis; appendicitis; cholecystitis; intestinal obstruction; hernias; etc (see, Giambernardino, M. A., et al., Pain. 1995; 61(3):459-69); chest pain, including, cardiac Pain (see, Vergona, R. A., et al., Life Sci. 1984; 35(18):1877-84); pelvic pain, renal colic pain, acute obstetric pain, including, labor pain (see, Segal, S., et al., Anesth Analg. 1998; 87(4):864-9); cesarean section pain; acute inflammatory, burn and trauma pain; acute intermittent pain, including, endometriosis (see, Cason, A. M., et al., Horm Behav. 2003; 44(2):123-31); acute herpes zoster pain; sickle cell anemia; acute pancreatitis (see, Toma, H; Gastroenterology. 2000; 119(5):1373-81); breakthrough pain; orofacial pain, including, sinusitis pain, dental pain (see, Nusstein, J., et al., J Endod. 1998; 24(7):487-91; Chidiac, J. J., et al., Eur J Pain. 2002; 6(1):55-67); multiple sclerosis (MS) pain (see, Sakurai & Kanazawa, J Neurol Sci. 1999; 162(2):162-8); pain in depression (see, Greene B, Curr Med Res Opin. 2003; 19(4):272-7); leprosy pain; behcet's disease pain; adiposis dolorosa (see, Devillers & Oranje, Clin Exp Dermatol. 1999; 24(3):240-1); phlebitic pain; Guillain-Barre pain; painful legs and moving toes; Haglund syndrome;

erythromelalgia pain (see, Legroux-Crespel, E., et al., Ann Dermatol Venereol. 2003; 130(4):429-33); Fabry's disease pain (see, Germain, D. P., J Soc Biol. 2002; 196(2):183-90); Bladder and urogenital disease, including, urinary incontinence (see, Berggren, T., et al., J Urol. 1993; 150(5 Pt 1):1540-3); hyperactivity bladder (see, Chuang, Y. C., et al., Urology. 2003; 61(3):664-70); painful bladder syndrome (see, Yoshimura, N., et al., J Neurosci. 2001; 21(21):8690-6); interstitial cyctitis (IC) (see, Giannakopoulos & Campilomatos, Arch Ital Urol Nefrol Androl. 1992; 64(4):337-9; Boucher, M., et al., J Urol. 2000; 164(1):203-8); and prostatitis (see, Mayersak, J. S., Int Surg. 1998; 83(4):347-9; Keith, I. M., et al., J Urol. 2001; 166(1):323-8).

Unfortunately, as described above, the efficacy of currently used sodium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel antagonists, preferably those with higher potency and fewer side effects.

SUMMARY OF THE INVENTION

It has now been found that compounds of this invention, and pharmaceutically acceptable compositions thereof, are useful as inhibitors of voltage-gated sodium channels. These compounds have the general formula I:

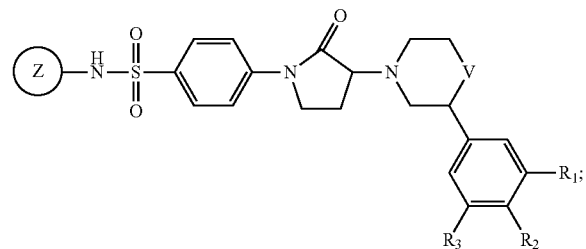

or a pharmaceutically acceptable salt thereof.

These compounds and pharmaceutically acceptable compositions are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

DETAILED DESCRIPTION OF THE INVENTION

In one embodiment, the present invention provides compounds of formula I:

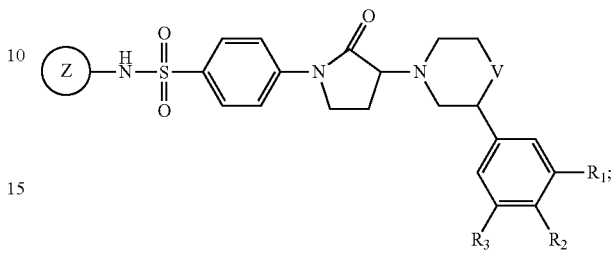

or a pharmaceutically acceptable salt thereof,
wherein,
ring Z is a thiazole or thiadiazole optionally substituted with 0-2 occurrences of R;
V is $CH_2$, NH, O, or S; and
R, $R_1$, $R_2$, and $R_3$ are hydrogen, C1-C6 aliphatic, aryl, C3-C8 cycloaliphatic, halo, CN, $NO_2$, $CF_3$, $OCF_3$, OH, $NH_2$, NH(C1-C6 aliphatic), N(C1-C6 aliphatic)$_2$, COOH, COO (C1-C6 aliphatic), O(C1-C6 aliphatic), $CHF_2$, or $CH_2F$.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable (i.e., having the requisite valency available for a given substituent) position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, alkynyl groups. The term "cycloaliphatic" means a monocyclic hydrocarbon, bicyclic, or tricyclic hydrocarbon that is completely saturated or that contains one or more units of unsaturation, but which is not aromatic and has a single point of attachment to the rest of the molecule. In some embodiments, "cycloaliphatic" refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members.

Unless otherwise specified, the term "heterocycle", "heterocyclyl", "heterocycloaliphatic", or "heterocyclic" as used herein means non-aromatic, monocyclic, bicyclic, or tricyclic ring systems in which one or more ring atoms in one or more ring members is an independently selected heteroatom. Heterocyclic ring can be saturated or can contain one or more unsaturated bonds. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the ring system contains 3 to 7 ring members.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

The term "alkylidene chain" refers to a straight or branched carbon chain that may be fully saturated or have one or more units of unsaturation and has two points of attachment to the rest of the molecule.

The term "spirocycloalkylene" refers to a cycloaliphatic ring that has two points of attachment from the same carbon atom to the rest of the molecule.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. For example, certain embodiments of compounds of formula (I), wherein hydrogen and ring Z is, e.g., thiazol-2-yl or pyridimidin-2-yl, can exist in tautomeric forms as shown below for compounds wherein Z is thiazol-2-yll:

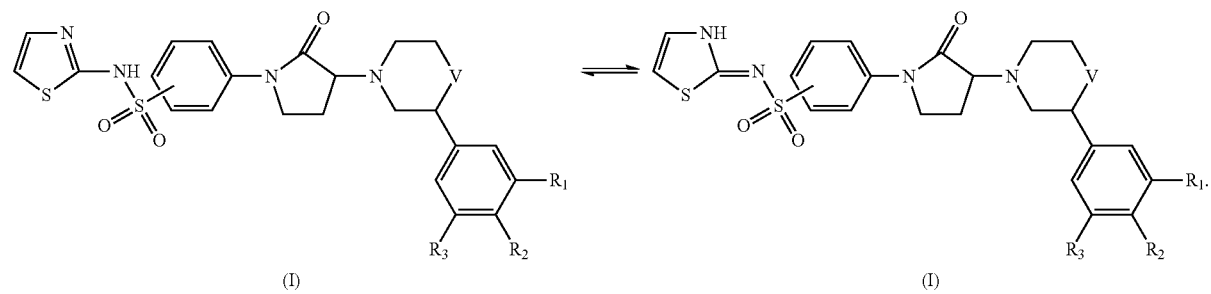

(I)

The term "heteroatom" means oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation but is not aromatic.

The term "alkoxy", or "thioalkyl", as used herein, refers to an alkyl group, as previously defined, attached to the principal carbon chain through an oxygen ("alkoxy") or sulfur ("thioalkyl") atom.

The term "aryl" used alone or as part of a larger moiety as in "aralkyl", "aralkoxy", or "aryloxyalkyl", refers to monocyclic, bicyclic, and tricyclic ring systems having a total of five to fourteen ring carbon atoms, wherein at least one ring in the system is aromatic and wherein each ring in the system contains 3 to 7 ring carbon atoms. The term "aryl" may be used interchangeably with the term "aryl ring".

Thus, included within the scope of the invention are tautomers of compounds of formula (I), wherein ring Z is a thiazole or thiadiazole, wherein the ring nitrogen atom in ring Z is amenable to a 1-3 tautomeric shift (e.g., when ring Z is a thiazol-2-yl ring) or 1-5 tautomeric shift (e.g., when ring Z is a thiadiazol-2-yl ring).

Additionally, unless otherwise stated, structures depicted herein are also meant to include compounds that differ only in the presence of one or more isotopically enriched atoms. For example, compounds of formula (I), wherein one or more hydrogen atoms are replaced deuterium or tritium, or one or more carbon atoms are replaced by a $^{13}C$- or $^{14}C$-enriched carbon are within the scope of this invention. Such compounds are useful, for example, as analytical tools, probes in biological assays, or sodium channel blockers with improved therapeutic profile.

In one embodiment, Z is an optionally substituted ring selected from:

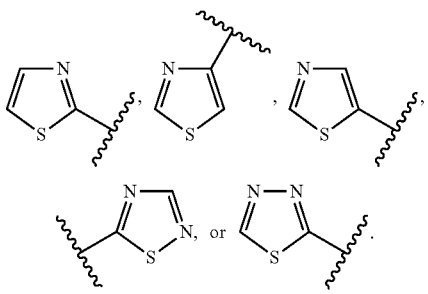

In certain embodiments of the compounds of the present invention, Z is selected from:

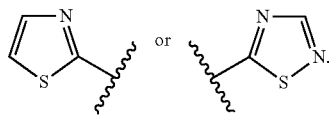 [SMILES: *c1nccs1 ; *c1ncns1]

In certain embodiments of the compounds of the present invention, Z is

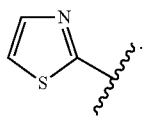

In certain embodiments of the compounds of the present invention, Z is

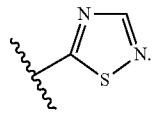

In one embodiment, $R_1$, $R_2$, and $R_3$ are hydrogen, C1-C6 aliphatic, halo, $CF_3$, $OCF_3$, $CHF_2$, $CH_2F$, or —$OCF_3$. In another embodiment, $R_1$, $R_2$, and $R_3$ are hydrogen, C1-C6 aliphatic, halo, or $CF_3$.

In one embodiment, Z is

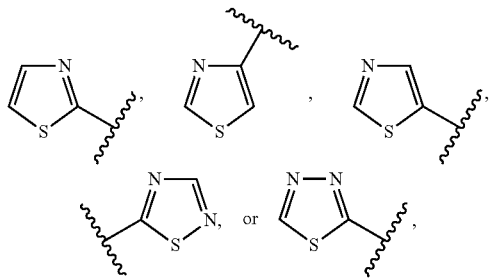

and $R_1$, $R_2$, and $R_3$ are hydrogen, C1-C6 aliphatic, halo, $CF_3$, $OCF_3$, $CHF_2$, $CH_2F$, or —$OCF_3$.

In one embodiment, Z is

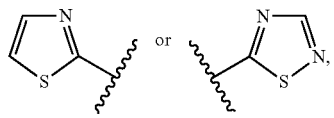 [SMILES: *c1nccs1 ; *c1ncns1]

and $R_1$, $R_2$, and $R_3$ are hydrogen, C1-C6 aliphatic, halo, or $CF_3$. In another embodiment, Z is

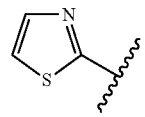

and $R_1$, $R_2$, and $R_3$ are hydrogen, C1-C6 aliphatic, halo, or $CF_3$.

In one embodiment, V is O or $CH_2$. In another embodiment, V is $CH_2$. In another embodiment, V is O.

In one embodiment, at least one of $R_1$, $R_2$, or $R_3$ is a halo. In another embodiment, at least two of $R_1$, $R_2$, or $R_3$ are halo. In another embodiment, $R_1$, $R_2$, and $R_3$ are H or halo. In another embodiment, $R_1$, $R_2$, and $R_3$ are H or Cl. In another embodiment, $R_1$ and $R_3$ are Cl. In another embodiment, $R_1$ and $R_2$ are Cl.

In one embodiment, Z is

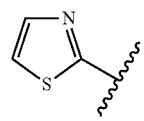

and V is $CH_2$. In another embodiment, Z is

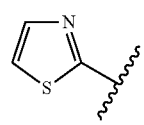 [SMILES: *c1nccs1]

and V is O.

In one embodiment, Z is

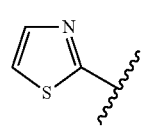 [SMILES: *c1nccs1]

and $R_1$ and $R_3$ are Cl. In another embodiment, Z is

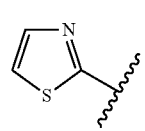 [SMILES: *c1nccs1]

and $R_1$ and $R_2$ are Cl.

In one embodiment, Z is

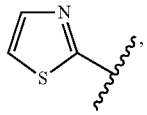

V is CH$_2$, and R$_1$ and R$_3$ are Cl.

In one embodiment, Z is

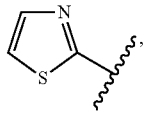

V is O, and R$_1$ and R$_3$ are Cl.

In one embodiment, Z is

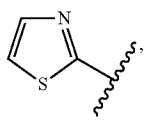

V is O, and R$_1$ and R$_2$ are Cl.

In one embodiment, the present invention provides compounds of formula Ia:

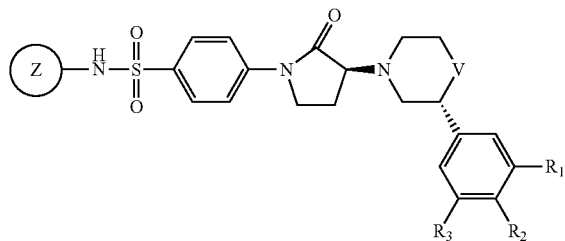

Ia wherein:

ring Z is a thiazole or thiadiazole optionally substituted with 0-2 occurrences of R;

V is CH$_2$, NH, O, or S; and

R, R$_1$, R$_2$, and R$_3$ are hydrogen, C1-C6 aliphatic, aryl, C3-C8 cycloaliphatic, halo, CN, NO$_2$, CF$_3$, OCF$_3$, OH, NH$_2$, NH(C1-C6 aliphatic), N(C1-C6 aliphatic)$_2$, COOH, COO(C1-C6 aliphatic), O(C1-C6 aliphatic), CHF$_2$, or CH$_2$F.

In one embodiment, Z is an optionally substituted ring selected from:

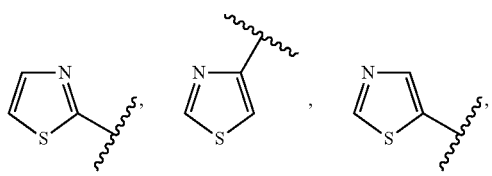

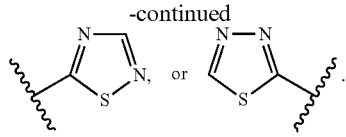

In certain embodiments of the compounds of the present invention, Z is selected from:

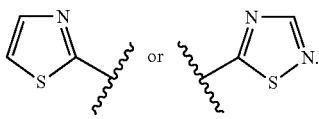 [SMILES: *c1nccs1 ; "or" ; *c1ncns1]

In certain embodiments of the compounds of the present invention, Z is

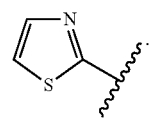 [SMILES: *c1nccs1 ; "."]

In certain embodiments of the compounds of the present invention, Z is

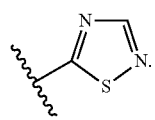 [SMILES: *c1ncns1]

In one embodiment, R$_1$, R$_2$, and R$_3$ are hydrogen, C1-C6 aliphatic, halo, CF$_3$, OCF$_3$, CHF$_2$, CH$_2$F, or —OCF$_3$. In another embodiment, R$_1$, R$_2$, and R$_3$ are hydrogen, C1-C6 aliphatic, halo, or CF$_3$.

In one embodiment, Z is

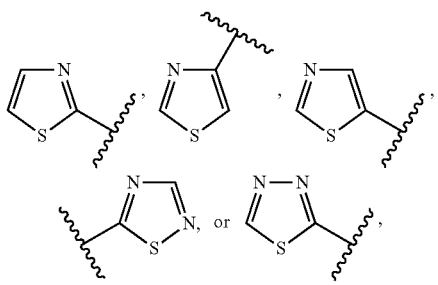

and R$_1$, R$_2$, and R$_3$ are hydrogen, C1-C6 aliphatic, halo, CF$_3$, OCF$_3$, CHF$_2$, CH$_2$F, or —OCF$_3$.

In one embodiment, Z is

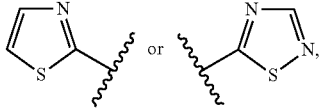 [SMILES: *c1nccs1 ; "or" ; *c1ncns1]

and R$_1$, R$_2$, and R$_3$ are hydrogen, C1-C6 aliphatic, halo, or CF$_3$. In another embodiment, Z is

[Structure: thiazol-2-yl group]

and R₁, R₂, and R₃ are hydrogen, C1-C6 aliphatic, halo, or CF₃.

In one embodiment, V is O or CH₂. In another embodiment, V is CH₂. In another embodiment, V is O.

In one embodiment, at least one of $R_1$, $R_2$, or $R_3$ is a halo. In another embodiment, at least two of $R_1$, $R_2$, or $R_3$ are halo. In another embodiment, $R_1$, $R_2$, and $R_3$ are H or halo. In another embodiment, $R_1$, $R_2$, and $R_3$ are H or Cl. In another embodiment, $R_1$ and $R_3$ are Cl. In another embodiment, $R_1$ and $R_2$ are Cl.

In one embodiment, Z is

[Structure: thiazol-2-yl group]

and V is CH₂. In another embodiment, Z is

[Structure: thiazol-2-yl group]

and V is O.

In one embodiment, Z is

[Structure: thiazol-2-yl group]

and $R_1$ and $R_3$ are Cl. In another embodiment, Z is

[Structure: thiazol-2-yl group]

and $R_1$ and $R_2$ are Cl.

In one embodiment, the present invention provides compounds of formula Ib:

[Structure of formula Ib]

or a pharmaceutically acceptable salt thereof,
wherein,
ring Z is a thiazole or thiadiazole optionally substituted with 0-2 occurrences of R;
V is CH₂, NH, O, or S; and
R, $R_1$, $R_2$, and $R_3$ are hydrogen, C1-C6 aliphatic, aryl, C3-C8 cycloaliphatic, halo, CN, NO₂, CF₃, OCF₃, OH, NH₂, NH(C1-C6 aliphatic), N(C1-C6 aliphatic)₂, COOH, COO(C1-C6 aliphatic), O(C1-C6 aliphatic), CHF₂, or CH₂F.

In one embodiment, Z is

[Structures: thiazole or thiadiazole groups]

In another embodiment, Z is

[Structures: five thiazole/thiadiazole groups]

In one embodiment, $R_1$, $R_2$, and $R_3$ are hydrogen, C1-C6 aliphatic, halo, CF₃, OCF₃, CHF₂, CH₂F, or —OCF₃. In another embodiment, $R_1$, $R_2$, and $R_3$ are hydrogen, C1-C6 aliphatic, halo, or CF₃.

In another embodiment, Z is

[Structures: five thiazole/thiadiazole groups]

and $R_1$, $R_2$, and $R_3$ are hydrogen, C1-C6 aliphatic, halo, CF₃, OCF₃, CHF₂, CH₂F, or —OCF₃. In another embodiment, Z is

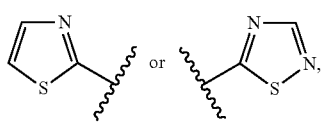 [SMILES: *c1nccs1 ; "or" ; *c1ncns1]

and $R_1$, $R_2$, and $R_3$ are hydrogen, C1-C6 aliphatic, halo, or $CF_3$.

In one embodiment, V is O or $CH_2$. In another embodiment, V is $CH_2$. In another embodiment, V is O.

In one embodiment, at least one of $R_1$, $R_2$, or $R_3$ is a halo. In another embodiment, at least two of $R_1$, $R_2$, or $R_3$ are halo. In another embodiment, $R_1$, $R_2$, and $R_3$ are H or halo. In another embodiment, $R_1$, $R_2$, and $R_3$ are H or Cl. In another embodiment, $R_1$ and $R_3$ are Cl. In another embodiment, $R_1$ and $R_2$ are Cl.

In one embodiment, Z is

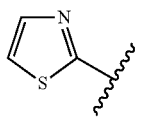

and V is $CH_2$. In another embodiment, Z is

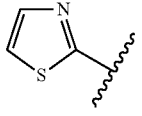 [SMILES: *c1nccs1]

and V is O. In another embodiment, Z is

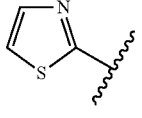 [SMILES: *c1nccs1]

and $R_1$ and $R_3$ are Cl. In another embodiment, Z is

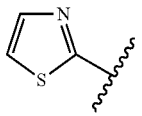 [SMILES: *c1nccs1]

and $R_1$ and $R_2$ are Cl.

Exemplary compounds of the present invention are shown below in Table 2.

TABLE 2

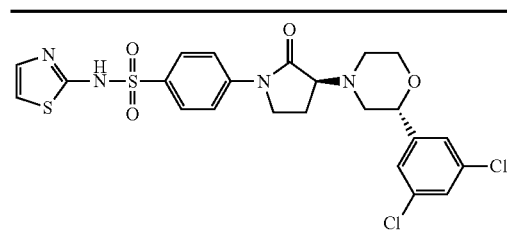

TABLE 2-continued

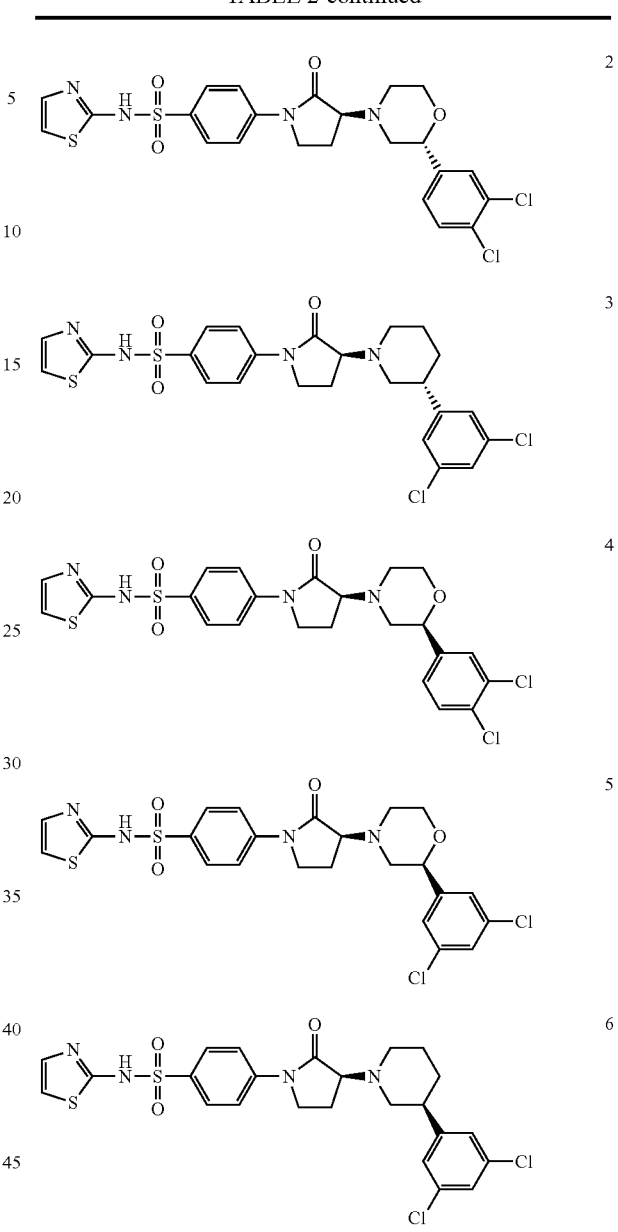

The compounds of the present invention may be prepared readily using methods known in the art. Illustrated below in Scheme 1 through Scheme 8 are methods for preparing the compounds of the present invention.

General Scheme 1

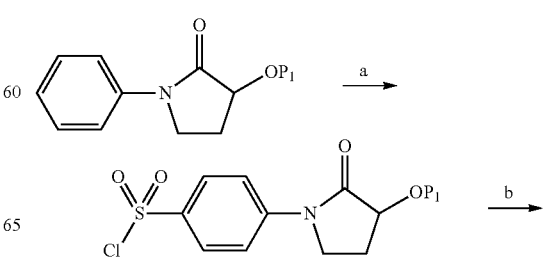

19
-continued
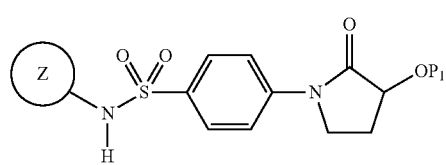
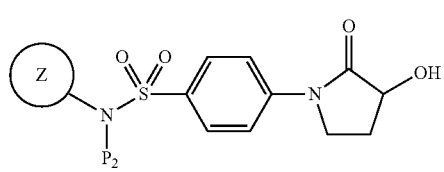
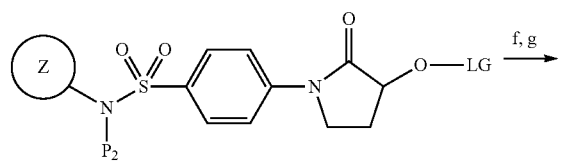
20
-continued
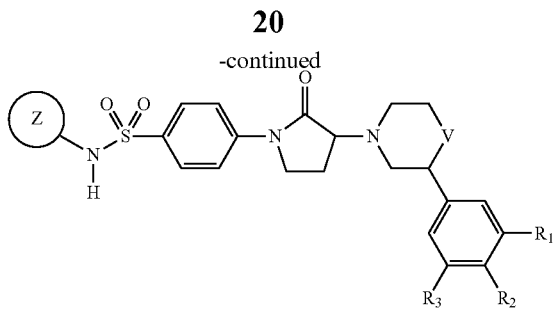
P$_1$ and P$_2$=H or PG, PG=protecting group; LG=leaving group. (a) ClSO$_3$H; (b) ZNH$_2$, base; (c, d) if P$_1$=PG then deprotection, if P$_2$=PG then protection; (e) addition of LG; (f, g)
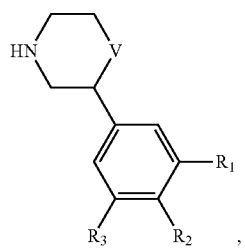
base, if P$_2$=PG then deprotection.
General Scheme 2
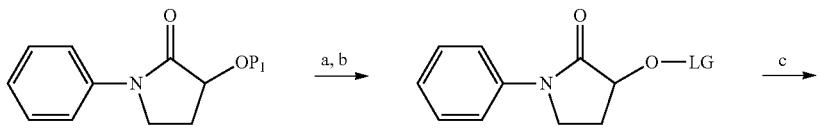
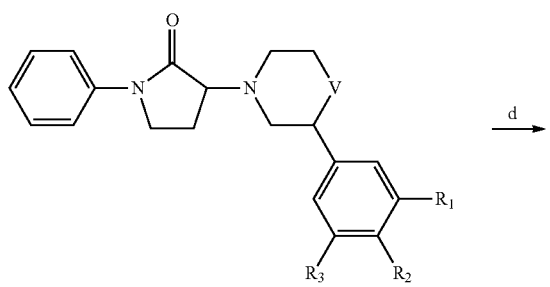
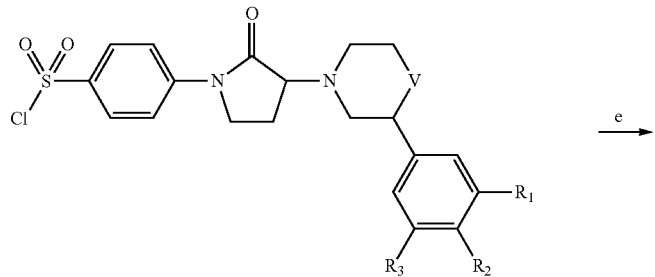

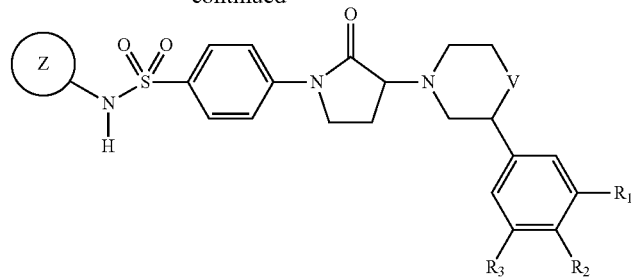
P₁=H or PG, PG=protecting group; LG=leaving group. (a, b) if P₁=PG then deprotection; addition of LG; (c)
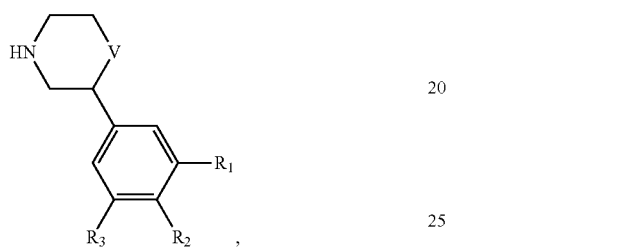
base; (d) ClSO₃H; (e) ZNH₂, base.
General Scheme 3
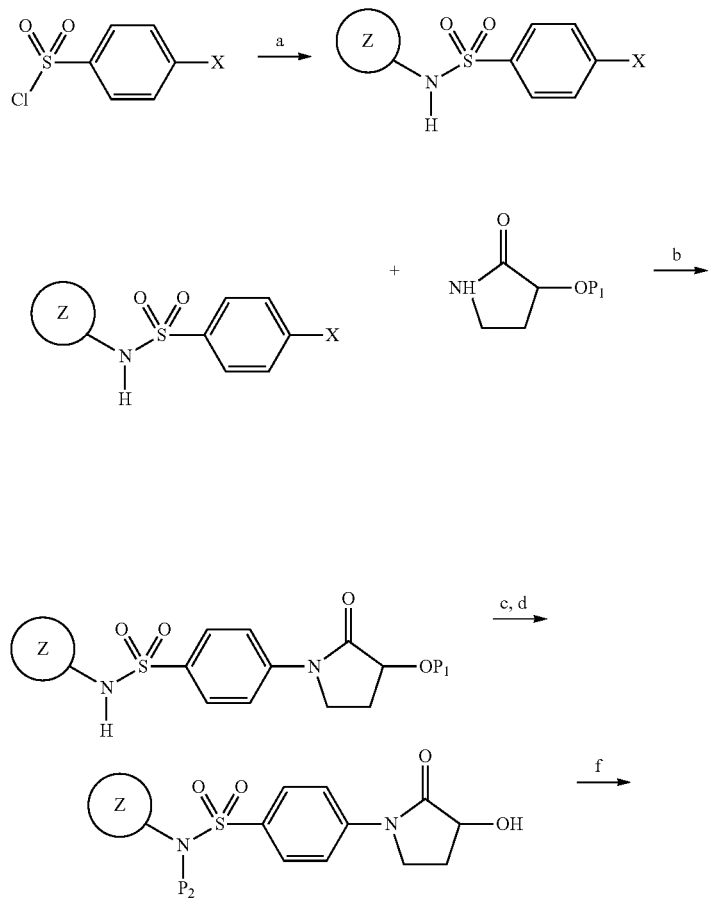

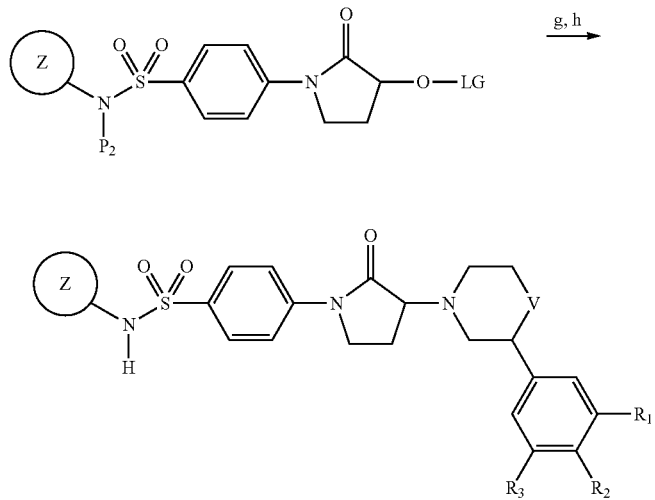
P₁ and P₂=H or PG, PG=protecting group; X=halogen. (a) ZNH₂, base; (b) CuI, base; (c,d) if P₁=PG then deprotection; if P₂=PG then protection; (e) addition of LG; (f, g)
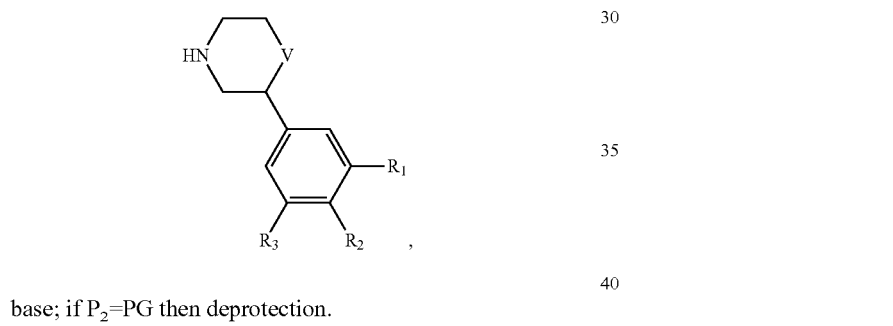
base; if P₂=PG then deprotection.
General Scheme 4
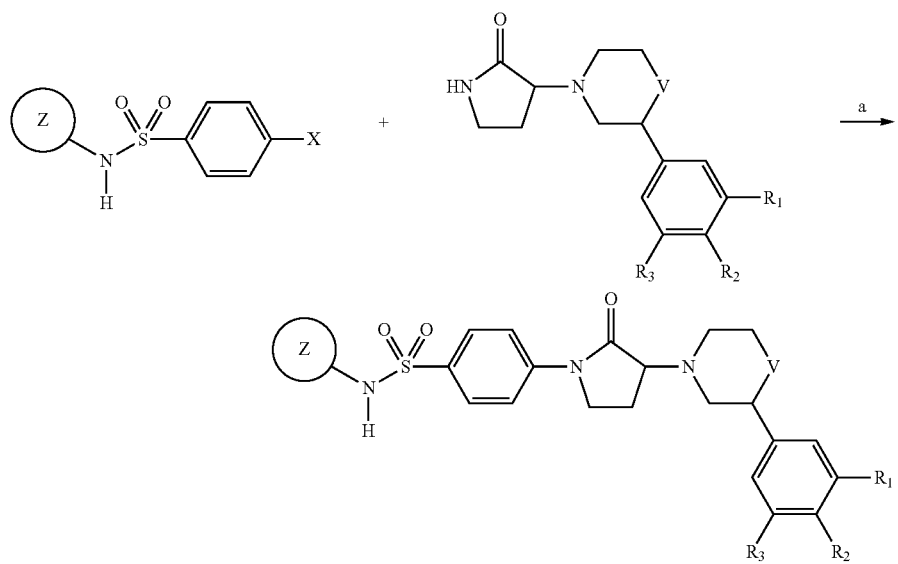

(a) CuI, base.
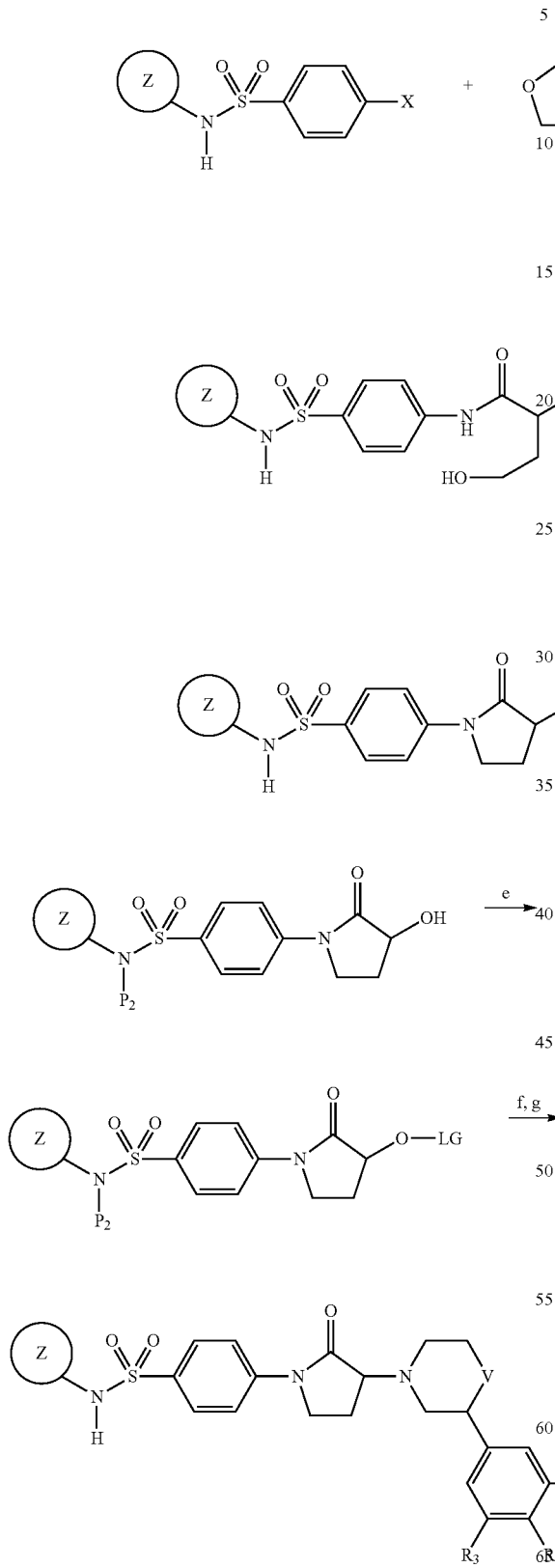
General Scheme 5

P$_1$ and P$_2$=H or PG, PG=protecting group; LG=leaving group; (a) AlMe$_3$, DCM; (b) PBu$_3$, DBAD, THF; or PPh$_3$, CBr$_4$, DCM, then DBU, CHCl$_3$; (c, d) if P$_1$=PG then deprotection, if P$_2$=PG then protection; (e) addition of LG; (f, g)
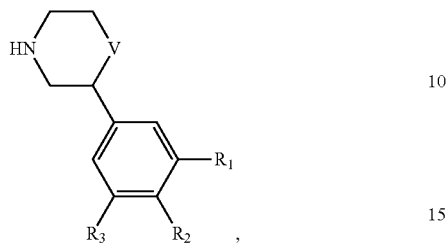
base; if P$_2$=PG then deprotection.
General Scheme 6
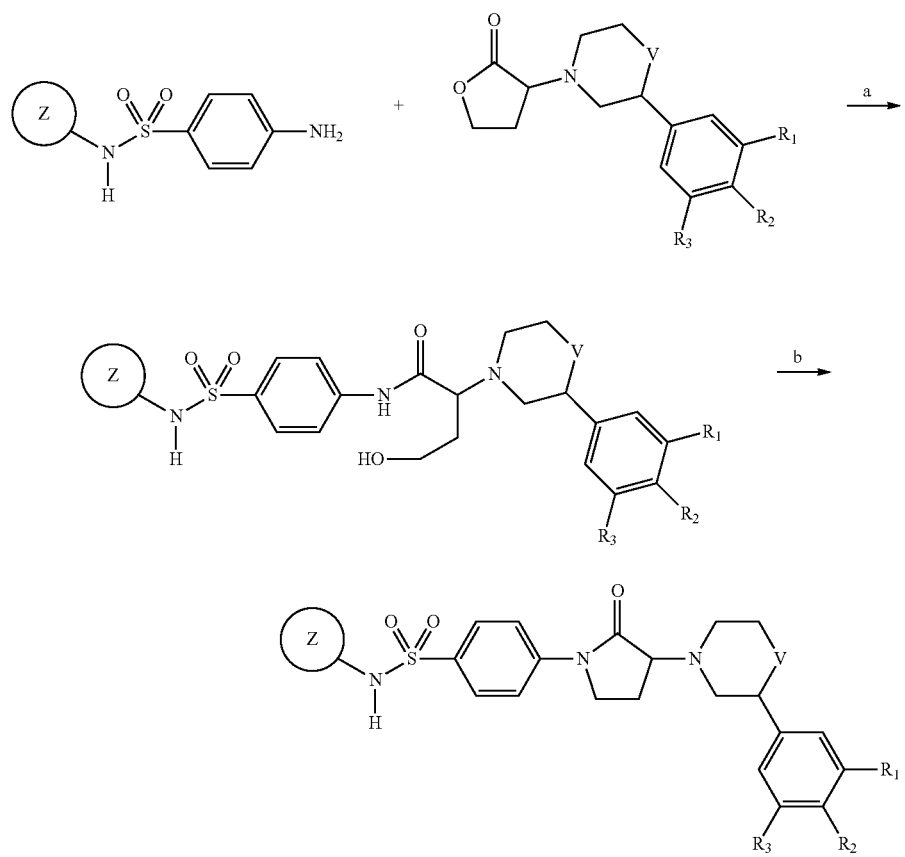
(a) AlMe$_3$, DCM; (b) PBu$_3$, DBAD, THF.
General Scheme 7
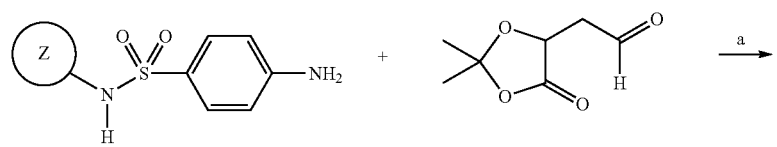

-continued
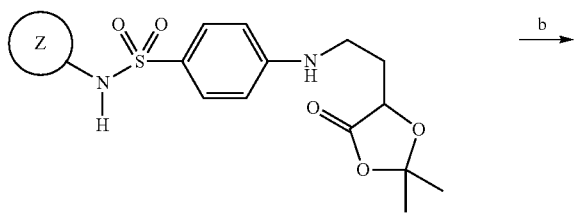
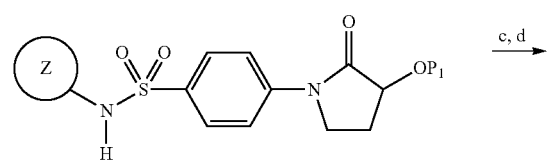
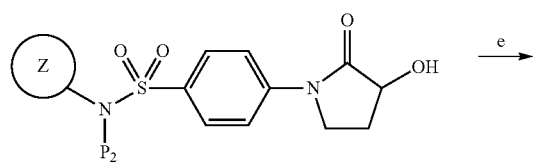
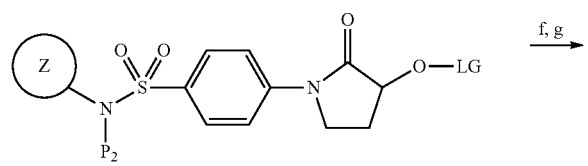
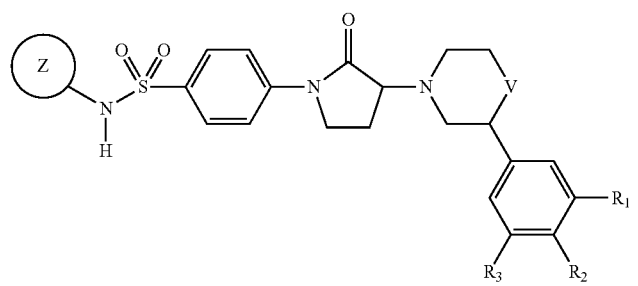
$P_1$ and $P_2$=H or PG, PG=protecting group; LG=leaving group; (a) NaBH$_4$, TFA, MeOH; (b) PTSA, THF; (c, d) if $P_1$=PG then deprotection, if $P_2$=PG then protection; (e) addition of LG; (f, g)

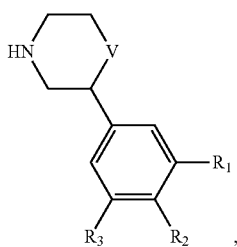

base; if P₂=PG then deprotection.

General Scheme 8

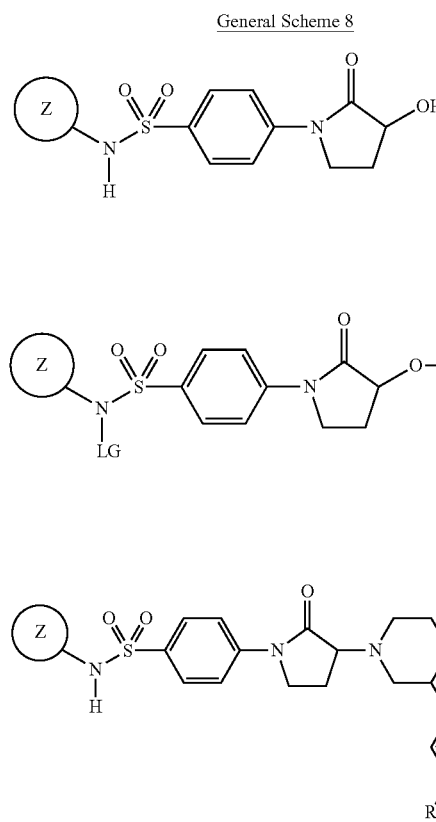

LG=leaving group. (a) addition of LG; (b)

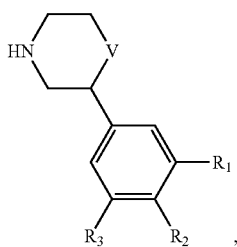

base.

Intermediates
1. A compound having formula N-1:

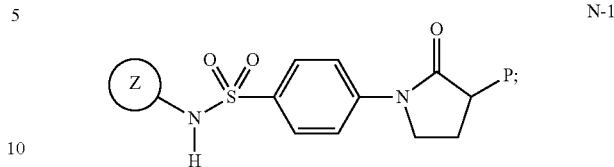

wherein:
ring Z is a thiazole or thiadiazole optionally substituted with 0-2 occurrences of R;
R is hydrogen, C1-C6 aliphatic, aryl, C3-C8 cycloaliphatic, halo, CN, $NO_2$, $CF_3$, $OCF_3$, OH, $NH_2$, NH(C1-C6 aliphatic), N(C1-C6 aliphatic)$_2$, COOH, COO (C1-C6 aliphatic), O(C1-C6 aliphatic), $CHF_2$, or $CH_2F$;
P is —O—PG or a suitable protecting group; and
PG is a suitable leaving group.

In one embodiment, P is a suitable protecting group. Suitable protecting groups include methoxymethyl, methoxyethyl, tetrahydropyranyl, allylcarbonate, trimethylsilyl, t-butyl-diphenylsilyl, t-butyl-dimethyl-silyl, acetate, benzoyl, benzyl, p-methoxybenzyl, etc. Other suitable protecting groups are well known to one of skill in the art, e.g., Greene, T. W.; Wuts, P. G. M. "Protecting Groups in Organic Synthesis", 3rd Ed; John Wiley & Sons, Inc.: New York, 1999; Chapter 2, p 17-245.

In another embodiment, P is —O—PG. Suitable leaving group, as used herein is a group capable of displacement. See, "Advanced Organic Chemistry: Reactions, Mechanisms, and Structure," pp. 339-357, Jerry March, 4$^{th}$ Ed., John Wiley & Sons (1992).

Examples of such leaving groups include trifluoromethanesulfonate, methanesulfonate, tosylate, halo, etc. Other suitable leaving groups are well known to one of skill in the art.

Uses, Formulation and Administration

Pharmaceutically Acceptable Compositions

As discussed above, the present invention provides compounds that are inhibitors of voltage-gated sodium ion channels, and thus the present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a subject in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel.

Pharmaceutically acceptable salts are well known in the art. For example, S. M. Berge, et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof.

In certain embodiments, a method of treatment or lessening the severity of stroke, cerebral ischemia, traumatic brain injury, amyotrophic lateral sclerosis, stress- or exercise induced angina, palpitations, hypertension, migraine, or abnormal gastro-intestinal motility is provided comprising administering an effective amount of a compound, or a pharmaceutically acceptable composition comprising a compound to a subject in need thereof.

In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, tinnitis or cancer pain is provided comprising administering an effective amount of a compound or a pharmaceutically acceptable composition to a subject in need thereof.

In certain embodiments, a method for the treatment or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic and acute headache pain; migraine; tension headache, including, cluster headaches; chronic and acute neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac Pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); or prostatitis; complex regional pain syndrome (CRPS), type I and type II; angina-induced pain is provided, comprising administering an effective amount of a compound or a pharmaceutically acceptable composition to a subject in need thereof.

In certain embodiments of the present invention an "effective amount" of the compound or pharmaceutically acceptable composition is that amount effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain.

The compounds and compositions, according to the method of the present invention, may be administered using any amount and any route of administration effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions of the present invention will be decided by the attending physician within the scope of sound medical judgment. The specific effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed, and like factors well known in the medical arts. The term "subject", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels. In one embodiment, the compounds and compositions of the invention are inhibitors of one or more of NaV1.1, NaV1.2, NaV1.3, NaV1.4, NaV1.5, NaV1.6, NaV1.7, NaV1.8, or NaV1.9, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease, condition, or disorder. When activation or hyperactivity of NaV1.1, NaV1.2, NaV1.3, NaV1.4, NaV1.5, NaV1.6, NaV1.7, NaV1.8, or NaV1.9 is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder". Accordingly, in another aspect, the present invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, or NaV1.9 may be assayed according to methods described generally in the Examples herein, or according to methods available to one of ordinary skill in the art.

In certain exemplary embodiments, compounds of the invention are useful as inhibitors of NaV1.3 and/or NaV1.1.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting one or more of NaV1.1, NaV1.2, NaV1.3, NaV1.4, NaV1.5, NaV1.6, NaV1.7, NaV1.8, or NaV1.9, activity in a biological sample or a subject, which method comprises administering to the subject, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of one or more of NaV1.1, NaV1.2, NaV1.3, NaV1.4, NaV1.5, NaV1.6, NaV1.7, NaV1.8, or NaV1.9, activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

EXAMPLES

General Methods $^1$H NMR (400 MHz) and $^{13}$C NMR (100 MHz) spectra were obtained as solutions in deuteriochloroform (CDCl$_3$) or dimethyl sulfoxide-D$_6$ (DMSO). Mass spectra (MS) were obtained using an Applied Biosystems API EX LC/MS system equipped with a Phenomenex 50×4.60 mm luna-5µ C18 column. The LC/MS eluting system was 10-99% acetonitrile in H$_2$O with 0.035% v/v trifluoroacetic acid using a 4.5 minute linear gradient and a flow rate of 4.0 mL/minute. Silica gel chromatography was performed using silica gel-60 with a particle size of 230-400 mesh. Pyridine, dichloromethane (CH$_2$Cl$_2$), tetrahydrofuran (THF), were from Aldrich Sure-Seal bottles kept under dry nitrogen. All reactions were stirred magnetically unless otherwise noted. Unless specified otherwise, all temperatures refer to internal reaction temperatures. In the methods below, Q represents

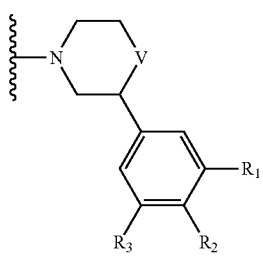

wherein V, $R_1$, $R_2$, and $R_3$ are as defined above and is generally referred to as "amine."

Synthesis of 1,2,4-Thiadiazol-5-ylamine

Method A (E)-N'-Carbamothioyl-N,N-dimethylformimidamide

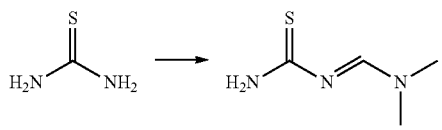

Under an $N_2$ atmosphere at RT, 1,1-dimethoxy-N,N-dimethylmethanamine (174 mL, 150 g, 1.31 mol) was added to a mixture of thiourea (90.0 g, 1.2 mol) and MeOH (950 mL), and the reaction was heated to reflux for 4 h. The mixture was allowed to cool to RT and stirred for 19 h. The reaction was then cooled to 0° C. and stirred for 1 h. The formed precipitate was filtered off and washed with a 1:1 mixture of MeOH and hexanes to obtain (E)-N'-carbamothioyl-N,N-dimethylformimidamide as a white solid (133 g, 85%). $^1$H NMR (400 MHz, DMSO-d6) δ 8.62 (s, 1H), 8.20 (s, 1H), 7.93 (s, 1H), 3.13 (s, 3H), 2.99 (s, 3H). LC/MS (10%-99% $CH_3CN$ (0.035% TFA)/$H_2O$ (0.05% TFA)), m/z: M+1 obs=132.0; $t_R$=0.37 min.

1,2,4-Thiadiazol-5-ylamine

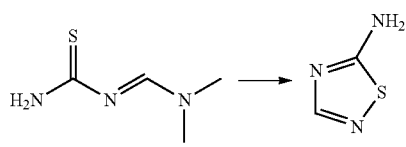

A mixture of (E)-N'-carbamothioyl-N,N-dimethylformimidamide (3.9 g, 30 mmol), hydroxylamine-O-sulfonic acid (3.7 g, 33 mmol) and EtOH (100 mL) was heated at 80° C. for 8 h. After cooling to RT, triethylamine was added, and the mixture was stirred at RT for 19 h. The solvents were evaporated under reduced pressure, and the residue was taken up in a 9:1 mixture of $CH_2Cl_2$:MeOH (10 mL) and purified via silica gel chromatography using 5% MeOH in $CH_2Cl_2$ to obtain 1,2,4-thiadiazol-5-amine as a white solid (1.4 g, 47%). $^1$H NMR (400 MHz, DMSO-d6) δ 7.95 (s, 2H), 7.85 (s, 1H). LC/MS (10%-99% $CH_3CN$ (0.035% TFA)/$H_2O$ (0.05% TFA)), m/z: M+1 obs=102.1; $t_R$=0.39 min.

Method B 1,2,4-Thiadiazol-5-ylamine

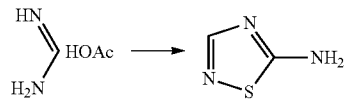

To a solution of formamidine (HOAc salt, 500 g, 4.8 mol) in MeOH (1500 mL) was added potassium thiocyanate (465 g, 4.8 mol). After stirring at room temperature for 10 min, a solution of sodium methoxide (520 g, 9.6 mol) in MeOH (1500 mL) was added to the resulting solution at 0° C., and then bromine (250 mL, 4.8 mol) was added dropwise to the solution at −15° C. After stirring at −10° C. for 0.5 h, 0° C. for 0.5 h, and at room temperature for 3 h, MeOH was removed under reduced pressure. The residue was dissolved in EtOAc, and the insoluble material was filtered. The filtrate was poured into a saturated aqueous NaCl solution, and the aqueous layer was extracted with EtOAc. The organic layer was dried over $Na_2SO_4$ and evaporated under reduced pressure. The residual gum was extracted with $Et_2O$ to give the crude compound [1,2,4]thiadiazol-5-ylamine (221 g), which was used in the next step without further purification.

1,2,4-Thiadiazol-5-ylamine hydrochloride

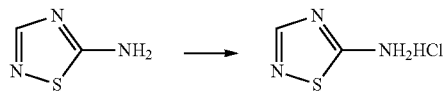

To a solution of 1,2,4-thiadiazol-5-ylamine (220 g, 2.19 mol) in MeOH (1000 mL) was added solution of HCl in MeOH (4 M, 1000 mL). After addition, the resulting suspension was stirred at room temperature for 1 h. The solid product was collected by filtration, washed with MeOH, and dried to give 1,2,4-thiadiazol-5-amine hydrochloride (137.7 g, 21% over two steps). $^1$H NMR (300 MHz, $D_2O$) δ 8.02 (s, 1H). MS (ESI) m/e (M+H$^+$) 101.2.

General Procedure 1

Method A

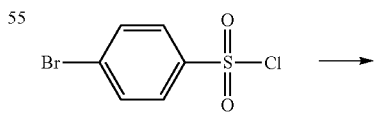

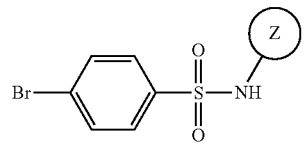

A mixture of 4-bromobenzene-1-sulfonyl chloride (1 equivalent), amino heterocycle (1 equivalent) and pyridine (2.2-4.4 M) was stirred under an $N_2$ atmosphere at RT for 19 h. Purification via silica gel chromatography using 5% MeOH in $CH_2Cl_2$ gave the desired product.

Method B

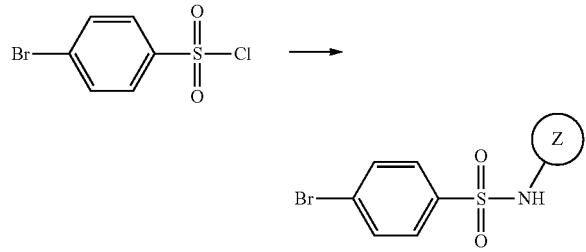

A mixture of 4-bromobenzene-1-sulfonyl chloride (1 equivalent, 1 mmol), amino heterocycle (1 equivalent, 1 mmol), 1,4-diazabicyclo[2.2.2]octane (DABCO) (1 equivalent, 1 mmol) and acetonitrile (4.8 mL) was stirred at RT overnight. Purification via silica gel chromatography using MeOH in $CH_2Cl_2$ gave the desired products.

4-Bromo-N-(thiazol-2-yl)benzenesulfonamide

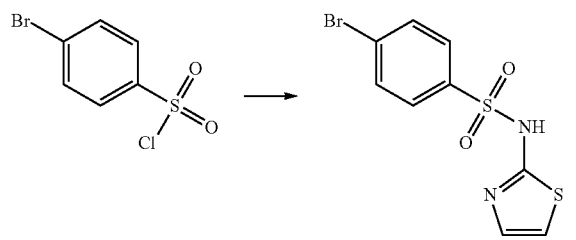 [SMILES: O=S(=O)(Cl)c1ccc(Br)cc1 ; O=S(=O)(Nc1nccs1)c1ccc(Br)cc1]

Synthesized according to General procedure 1, Method A. Yield: 99%. $^1$H NMR (400 MHz, DMSO-d6) δ 7.77-7.71 (m, 4H), 7.29 (d, J=4.6 Hz, 1H), 6.87 (d, J=4.6 Hz, 1H). LC/MS (10%-99% $CH_3CN$ (0.035% TFA)/$H_2O$ (0.05% TFA)), m/z: M+1 obs=319.0; $t_R$=3.22 min.

General Procedure 2

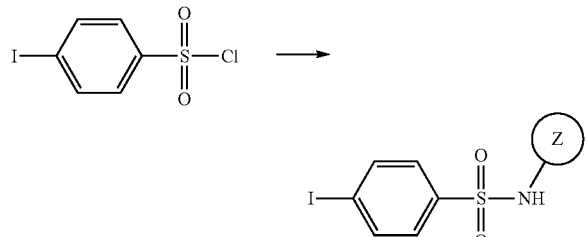

To a stirring solution of the aminoheterocycle (2.4 equivalents, 2.4 mmol) and pyridine (0.35 mL) under $N_2$, at 0° C., was added pipsyl chloride (1 equivalent, 1 mmol). The mixture was stirred at ambient temperature for 17 hours. $CH_2Cl_2$/MeOH-2/1 was added. The mixture was filtered and the filtrate was purified via silica gel chromatography using MeOH in $CH_2Cl_2$. The solid was triturated to give the desired products.

4-Iodo-N-(thiazol-2-yl)benzenesulfonamide

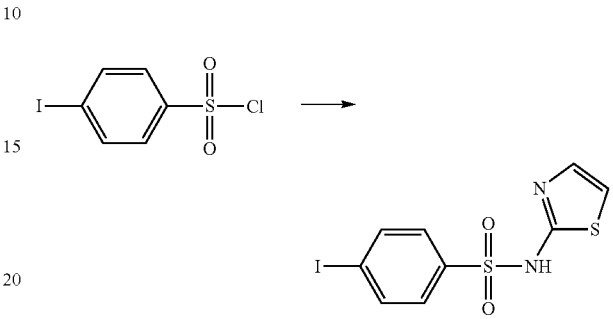

To a stirring solution of 2-aminothiazole (13.2 g, 132.2 mmol) and pyridine (20 mL) under $N_2$, at 0° C., was added pipsyl chloride (20.0 g, 55.1 mmol). The mixture was stirred at ambient temperature for 17 hours. $CH_2Cl_2$/MeOH-2/1 (100 mL) was added. The mixture was filtered and the filtrate was purified via silica gel chromatography using 5% MeOH in $CH_2Cl_2$. The solid was triturated with $CH_2Cl_2$ to obtain the desired sulfonamide as a white solid (8.4 g, 20.9 mmol, 38% yield). $^1$H NMR (400 MHz, DMSO-d6) δ 12.83 (s, 1H), 7.94-7.90 (m, 2H), 7.57-7.54 (m, 2H), 7.26 (d, J=4.6 Hz, 1H), 6.86 (d, J=4.6 Hz, 1H).

Route 1

(R)-5-(2-Hydroxyethyl)-2,2-dimethyl-1,3-dioxolan-4-one

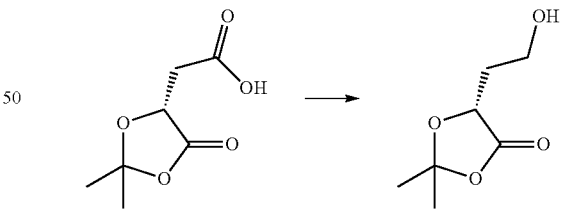

To a stirring solution of (R)-(−)-dimethyl-5-oxo-1,2-dioxolane-4-acetic acid (15.8 g, 91 mmol), and THF (90 mL), at 0° C., under $N_2$, was added borane-THF complex (1.0 M in THF, 100 mL, 100 mmol) dropwise over 60 minutes. The mixture was stirred at 0° C. for 2.5 hours and then allowed to warm to 25° C. The mixture was stirred at room temperature for 19 hours. The mixture was poured into MeOH (150 mL) and the solution was evaporated to dryness under reduced pressure at 25° C. The residue was purified via silica gel chromatography using 30% EtOAc in hexanes to obtain the desired alcohol as a clear oil (7.1 g, 44.6 mmol, 49% yield). $^1$H NMR (400 MHz, CDCl₃) δ 4.61-4.51 (m, 1H), 3.89-3.80 (m, 2H), 2.20-2.12 (m, 2H), 2.05-1.98 (m, 1H), 1.64 (s, 3H), 1.57 (s, 3H).

(R)-3-Hydroxydihydrofuran-2(3H)-one

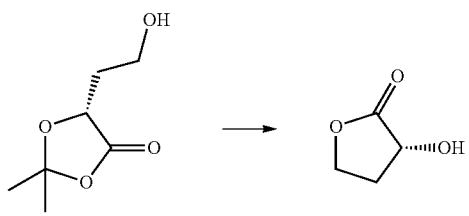

A solution of (R)-5-(2-hydroxyethyl)-2,2-dimethyl-1,3-dioxolan-4-one (33.0 g, 206 mmol), p-toluenesulfonic acid monohydrate (400 mg, 2.1 mmol), and benzene (300 mL) was stirred at 25° C. for 3 hours. The solution was evaporated to dryness under reduced pressure at 25° C. The residue was purified via silica gel chromatography using 50% EtOAc in hexanes to give the desired lactone as a clear oil (18.0 g, 176 mmol, 85% yield). ¹H NMR (400 MHz, CDCl₃) δ 4.57-4.52 (m, 1H), 4.44 (td, J=9.0, 3.6 Hz, 1H), 4.28-4.21 (m, 1H), 3.72 (s, 1H), 2.66-2.58 (m, 1H), 2.35-2.24 (m, 1H).

(R)-3-(tert-butyldiphenylsilyloxy)dihydrofuran-2(3H)-one

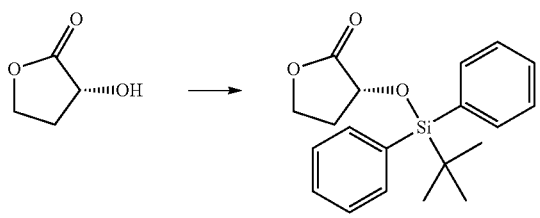 [SMILES: O=C1OCC[C@H]1O ; CC(C)(C)[Si](O[C@@H]1CCOC1=O)(c1ccccc1)c1ccccc1]

To a stirring solution of (R)-3-hydroxydihydrofuran-2(3H)-one (41.0 g, 401 mmol), imidazole (61.4 g, 920 mmol), and CH₂Cl₂ (175 mL) at 0° C., under N₂, was added t-butyldiphenylsilyl chloride (129 mL, 138 g, 497 mmol) dropwise over 30 minutes. The mixture was stirred at room temperature for 19 hours. The mixture was partitioned between CH₂Cl₂ (700 mL) and H₂O (100 mL). The organic portion concentrated to dryness under reduced pressure. The residue was purified via silica gel chromatography using 50% EtOAc in hexane to give the desired lactone as a white solid (127 g, 373 mmol, 93% yield). ¹H NMR (400 MHz, CDCl₃) δ 7.84-7.82 (m, 2H), 7.73-7.71 (m, 2H), 7.50-7.40 (m, 6H), 4.41-4.31 (m, 2H), 4.06-4.00 (m, 1H), 2.29-2.19 (m, 2H), 1.10 (s, 9H).

General Procedure 3

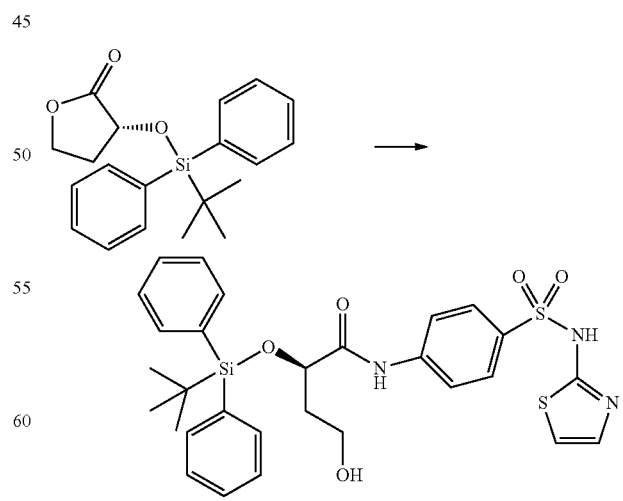

To a stirring suspension of the aniline (1.3 mmol) and CH₂Cl₂ (5.5 mL) under N₂, at 0° C., was added trimethylaluminum (1.3 mmol) dropwise over 20 minutes. The solution was stirred at ambient temperature for 30 minutes. The solution was cooled to 0° C. followed by the dropwise addition of (R)-3-(tert-butyldiphenylsilyloxy)dihydrofuran-2(3H)-one (1 mmol) in CH₂Cl₂ (1.0 mL) over 30 minutes. The solution was stirred at ambient temperature for 19 hours. The solution was cooled to 0° C. and aqueous 1.0 M HCl was added dropwise over 1.5 hours. The organic portion was washed with 1.0 N aqueous HCl (2×1.0 mL) and evaporated to dryness under reduced pressure. The residue was purified via silica gel using MeOH in CH₂Cl₂ to obtain the desired amide as a white solid.

(R)-2-(tert-Butyldiphenylsilyloxy)-4-hydroxy-N-(4-(N-thiazol-2-ylsulfamoyl)phenyl)butanamide Synthesized according to General procedure 3. The reaction was set up with sulfathiazole (122 g, 477 mmol), CH₂Cl₂ (1.5 L), trimethylaluminum (2.0 M in hexanes, 239 mL, 477 mmol), and (R)-3-(tert-butyldiphenylsilyloxy)dihydrofuran-2(3H)-one (125 g, 367 mmol) in CH$_2$Cl$_2$ (250 mL). The reaction was purified via silica gel using 10% MeOH in CH$_2$Cl$_2$ to obtain the desired amide as a white solid (207 g, 348 mmol, 95% yield). $^1$H NMR (400 MHz, DMSO-d6) δ 8.73 (s, 1H), 7.76 (dd, J=1.8, 7.0 Hz, 1H), 7.74 (s, 1H), 7.59-7.53 (m, 4H), 7.44-7.28 (m, 8H), 7.09 (d, J=4.6 Hz, 1H), 6.46 (d, J=4.6 Hz, 1H), 4.34 (dd, J=4.1, 6.7 Hz, 1H), 3.64-3.59 (m, 1H), 3.54 (dd, J=6.1, 11.4 Hz, 1H), 1.99-1.91 (m, 1H), 1.81-1.70 (m, 1H), 1.10 (s, 9H). LC/MS (10%-99% CH$_3$CN (0.035% TFA)/H$_2$O (0.05% TFA)), m/z: M+1 obs=596.5; $t_R$=1.93 min.

General Procedure 4 mide. To a solution of the bromide (1.0 equivalent, 1.0 mmol) in chloroform (3.5 mL; HPLC grade), DBU (2.0 equivalents, 2.0 mmol) was added and stirred at room temperature under N$_2$ atmosphere for 1 h. The reaction was diluted with DCM and the organic layer was washed with aqueous 1 N HCl (3×), saturated aqueous NaHCO$_3$ (2×) and brine (1×). The organic layer was dried over Na$_2$SO$_4$ and concentrated to provide the desired lactam.

(R)-4-(3-(tert-Butyldiphenylsilyloxy)-2-oxopyrrolidin-1-yl)-N-(thiazol-2-yl)benzenesulfonamide

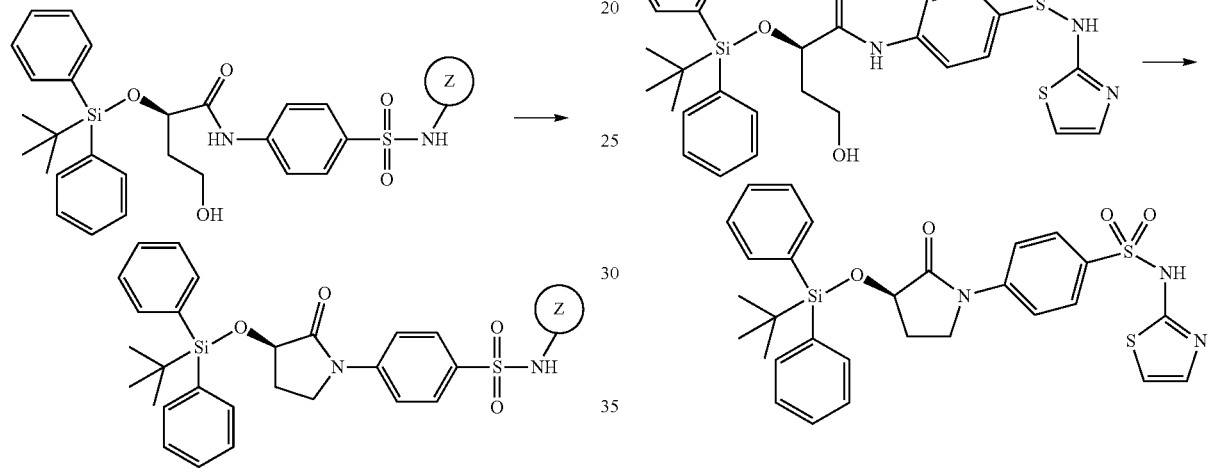

Method A

To a stirring solution of di-tert-butyl-azodicarboxylate (3.0 equivalent, 3.0 mmol) and THF (2.0 mL), under N$_2$, at 0° C., was added tributylphosphine (3.0 equivalent, 3.0 mmol), dropwise over 5 minutes. The colourless solution was stirred at 0° C. for 30 minutes. A solution of amidoalcohol (1.0 equivalent, 1.0 mmol) in THF (0.60 mL) was added dropwise over 5 minutes. The solution was stirred at ambient temperature for 2 hours. To this solution was added H$_2$O (40 uL) and the solution was evaporated to dryness. The residue was purified via silica gel using EtOAc in hexanes to give the desired lactam.

Method B

The alcohol (1.0 equivalent, 1.0 mmol) in anhydrous DCM (4.0 mL) was stirred and cooled down to 0° C. To this, a solution of PPh$_3$ (1.5 equivalents, 1.5 mmol) in anhydrous DCM (0.90 mL) was slowly added followed by the slow addition of CBr$_4$ (1.5 equivalents, 1.5 mmol) in anhydrous DCM (0.90 mL). On completion of CBr$_4$ addition, the reaction was maintained at 0° C. for 5 min. The ice bath was removed and the reaction was stirred at room temperature for 4 h. The reaction was diluted with DCM and the organic layer was washed with saturated aqueous NaHCO$_3$ (2×) and brine (1×). The organic layer was dried over Na$_2$SO$_4$ and concentrated. The crude product was purified by column chromatography (gradient 0-100% EtOAc/Hexane) to provide the bro- Synthesized according to General procedure 4, Method A. The reaction was set up with di-tert-butyl-azodicarboxylate (1.81 g, 7.88 mmol), THF (15 mL), tributylphosphine (1.59 g, 7.88 mmol), and (R)-2-(tert-butyldiphenylsilyloxy)-4-hydroxy-N-(4-(N-thiazol-2-ylsulfamoyl)phenyl)butanamide (1.56 g, 2.63 mmol). The residue was purified via silica gel using 40% EtOAc in hexanes to give the desired lactam as a white solid (1.3 g, 2.3 mmol, 86% yield). $^1$H NMR (400 MHz, DMSO-d6) δ 7.83-7.76 (m, 4H), 7.70 (dd, J=1.9, 7.0 Hz, 2H), 7.65 (dd, J=1.5, 8.0 Hz, 2H), 7.39-7.29 (m, 6H), 7.06 (d, J=4.6 Hz, 1H), 6.44 (d, J=4.6 Hz, 1H), 4.35 (dd, J=7.9, 9.2 Hz, 1H), 3.67-3.62 (m, 1H), 3.48-3.42 (m, 1H), 2.18-1.98 (m, 2H) 1.11 (s, 9H).

Synthesized according to General procedure 4, Method B. The reaction was set up with (R)-2-(tert-Butyldiphenylsilyloxy)-4-hydroxy-N-(4-(N-thiazol-2-ylsulfamoyl) phenyl)butanamide (10.0 g, 16.78 mmol, 1.0 equiv.), DCM (70 mL), PPh$_3$ (6.6 g, 25.2 mmol, 1.5 equiv.), CBr$_4$ (8.35 g, 25.2 mmol, 1.5 equiv.), DBU (3.53 mL, 23.58 mmol, 2.0 equiv.) The organic layer was dried over Na$_2$SO$_4$ and concentrated to provide the lactam as a yellow solid (6.25 g, 92%). $^1$H NMR (400 MHz, DMSO-d6) δ 7.83-7.76 (m, 4H), 7.70 (dd, J=1.9, 7.0 Hz, 2H), 7.65 (dd, J=1.5, 8.0 Hz, 2H), 7.39-7.29 (m, 6H), 7.06 (d, J=4.6 Hz, 1H), 6.44 (d, J=4.6 Hz, 1H), 4.35 (dd, J=7.9, 9.2 Hz, 1H), 3.67-3.62 (m, 1H), 3.48-3.42 (m, 1H), 2.18-1.98 (m, 2H) 1.11 (s, 9H).

General Procedure 5

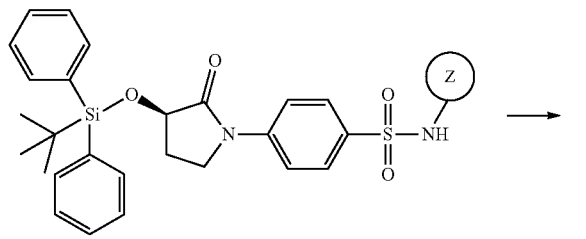

To a stirring suspension of benzenesulfonamide (1.0 mmol) in CH$_2$Cl$_2$ (2.3 mL), under N$_2$, at 0° C., was added N,N-diisopropylethylamine (2.0 mmol) followed by allylbromide (2.0 mmol). The mixture was stirred at ambient temperature for 19 hours. The mixture was evaporated to dryness under reduced pressure. The residue was purified via silica gel using EtOAc in hexanes to give the desired alkylsulfonamide.

(R)—N-Allyl-4-(3-(tert-butyldiphenylsilyloxy)-2-oxopyrrolidin-1-yl)-N-(thiazol-2-yl)benzenesulfonamide

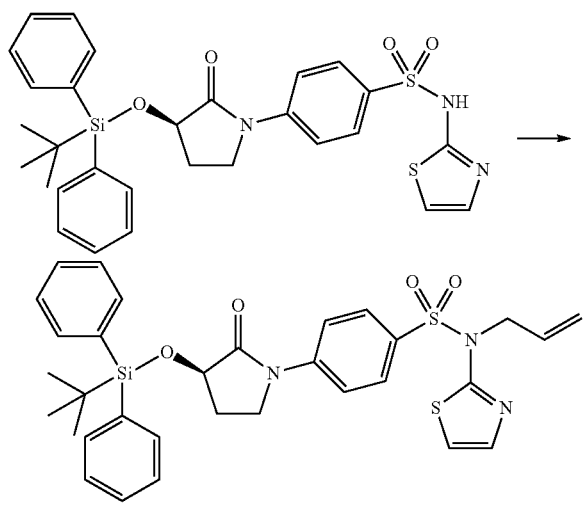

Synthesized according to General procedure 5. The reaction was set up with (R)-4-(3-(tert-butyldiphenylsilyloxy)-2-oxopyrrolidin-1-yl)-N-(thiazol-2 yl)benzene-sulfonamide (50.0 g, 86.6 mmol), CH$_2$Cl$_2$ (200 mL), N,N-diisopropylethylamine (30.2 mL, 173.2 mmol), and allylbromide (15.0 mL, 173.2 mmol). The residue was purified via silica gel using 50% EtOAc in hexanes to give the desired sulfonamide as a white solid (45.0 g, 72.7 mmol, 84% yield). $^1$H NMR (400 MHz, DMSO-d6) δ. 7.85-7.79 (m, 6H), 7.70 (dd, J=1.6, 7.7 Hz, 2H), 7.49-7.40 (m, 6H), 7.36 (d, J=4.7 Hz, 1H), 6.93 (d, J=4.7 Hz, 1H), 5.90-5.82 (m, 1H), 5.16 (dd, J=1.3, 10.3 Hz, 1H), 4.97 (d, J=1.3 Hz, 1H), 4.56-4.52 (m, 3H), 3.76-3.72 (m, 1H), 3.56-3.48 (m, 1H), 2.28-2.25 (m, 1H), 2.19-1.98 (m, 1H), 1.11 (s, 9H).

(R)—N-Allyl-4-(3-hydroxy-2-oxopyrrolidin-1-yl)-N-(thiazol-2-yl)benzenesulfonamide

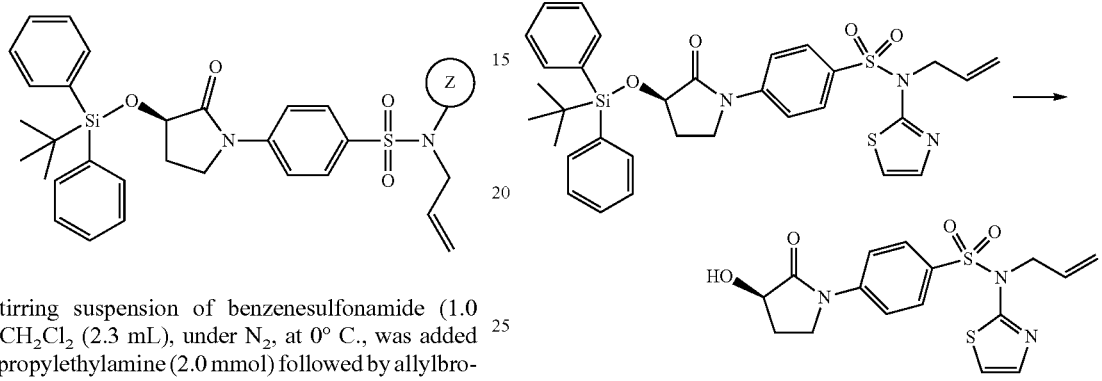

To a stirring solution of (R)—N-allyl-4-(3-(tert-butyldiphenylsilyloxy)-2-oxopyrrolidin-1-yl)-N-(thiazol-2-yl) benzenesulfonamide (78.7 g, 127 mmol) and THF (300 mL) under N$_2$, at 0° C., was added tetrabutylammonium fluoride (1.0 M in THF, 255 mL, 255 mmol) dropwise over 20 minutes. The mixture was stirred at ambient temperature for 2 hours. To this solution was added H$_2$O (5 mL) followed by evaporation to dryness. The residue was purified via silica gel using 30% EtOAc in hexanes to obtain the desired alcohol as a white solid (39.5 g, 104 mmol, 82% yield). $^1$H NMR (400 MHz, DMSO-d6) δ 7.86-7.80 (m, 4H), 7.37 (d, J=4.7 Hz, 1H), 6.93 (d, J=4.7 Hz, 1H), 5.92-5.83 (m, 2H), 5.17 (dd, J=1.3, 10.3 Hz, 1H), 4.98 (q, J=1.4 Hz, 1H), 4.55 (dt, J=5.3, 1.7 Hz, 2H), 4.36-4.30 (m, 1H), 3.81-3.76 (m, 1H), 3.70 (td, J=9.5, 5.4 Hz, 1H), 2.45-2.38 (m, 1H), 1.90-1.80 (m, 1H).

General Procedure 6

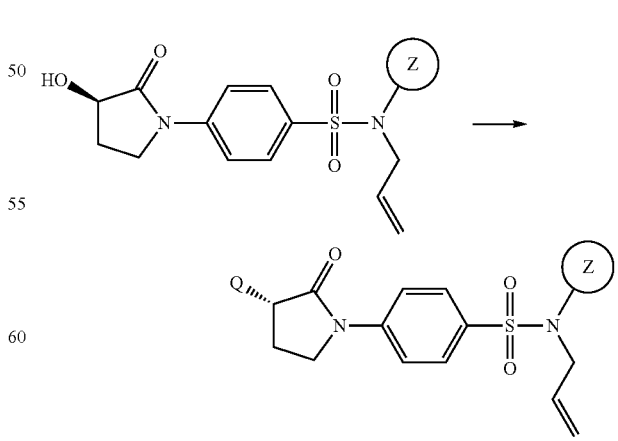

To a stirring solution of alcohol (1.0 mmol) in CH$_2$Cl$_2$ (3.0 mL) under N$_2$, at −40° C., was added N,N-diisopropylethylamine (2.0 mmol) followed by the dropwise addition of triflic anhydride (1.1 mmol) over 20 minutes. The mixture was stirred at −40° C. for 1 hour. To this solution was added the amine (1.5 mmol) at −40° C. The solution was held at a specific temperature (−20° C. to 25° C.) for a specified time followed by quenching with $H_2O$. The reaction was evaporated to dryness under reduced pressure. The residue was purified via silica gel using MeOH in $CH_2Cl_2$ to obtain the desired lactam.

General Procedure 7

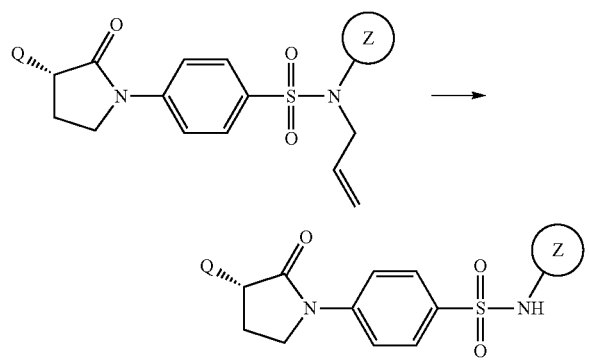

To a stirring suspension of allyl sulfonamide (1.0 mmol) and $CH_3CN$ (3.8 mL) was added $Pd(PPh_3)_4$ (0.2 mmol) and 1,3-dimethylbarbituric acid (10 mmol). The mixture was heated at 60° C. for 4 hours. The reaction was evaporated to dryness under reduced pressure. The residue was purified via silica gel using MeOH in $CH_2Cl_2$ to obtain the desired sulfonamide.

Route 2

General Procedure 8

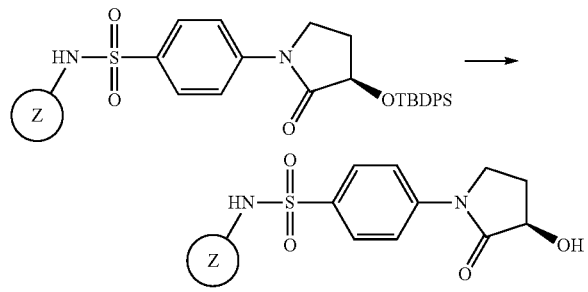

To a solution of protected TBDPS sulfonamide (1 equivalent) in THF (0.5-1 M) under $N_2$, was added a solution of tetrabutylammonium fluoride in THF (1M, 4 equivalent). Upon completion of addition, the mixture was stirred at RT overnight. The reaction mixture was poured into water and extracted with $CH_2Cl_2$ (2×), dried over magnesium sulfate, and concentrated. Purification via silica gel chromatography using 2-10% MeOH in $CH_2Cl_2$ gave desired product.

(R)-4-(3-Hydroxy-2-oxopyrrolidin-1-yl-N-(thiazol-2-yl)benzenesulfonamide

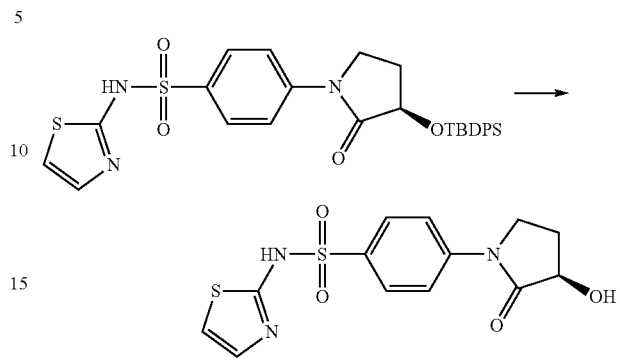

Synthesized according to General procedure 8. To a solution of (R)-4-(3-(tert-butyldiphenylsilyloxy)-2-oxopyrrolidin-1-yl-N-(thiazol-2-yl)benzenesulfonamide (5.5 g, 9.53 mmol) in THF (40 mL) under $N_2$, was added a solution of tetrabutylammonium fluoride in THF (1M, 40 mL, 38.1 mmol). Upon completion of addition, the mixture was stirred at RT overnight. The reaction mixture was poured into water and extracted with $CH_2Cl_2$ (2×50 mL), dried over magnesium sulfate, and concentrated. Purification via silica gel chromatography using 2-10% MeOH in $CH_2Cl_2$ gave (R)-4-(3-hydroxy-2-oxopyrrolidin-1-yl-N-(thiazol-2-yl)benzenesulfonamide (2.6 g, 76%). LC/MS (10%-99% $CH_3CN$ (0.035% TFA)/$H_2O$ (0.05% TFA)), m/z: M+1 obs=340.0; $t_R$=0.54 min.

General Procedure 9

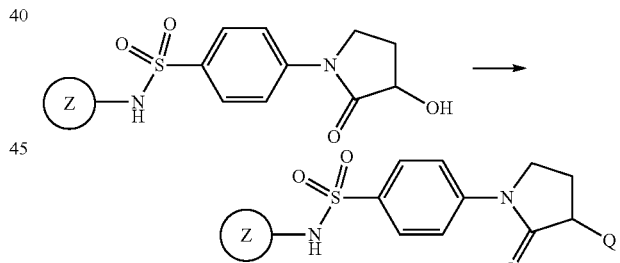

Under an $N_2$ atmosphere at −40° C., N,N-diisopropylethylamine (2-4 equivalent) was added dropwise to a solution of alcohol (1 equivalent) in $CH_2Cl_2$ (0.5 M). Trifluoromethanesulfonic anhydride (1.1-2.1 equivalent) was added dropwise to this solution maintaining the internal temperature of the reaction mixture below −40° C. Upon completion of addition, the mixture was stirred at −40° C. for 1 h. A solution of amine (1.5-3 equivalent) in $CH_2Cl_2$ (40 mL) was added dropwise to this solution maintaining the internal temperature of the reaction mixture below −40° C. The reaction was allowed to warm up to −20° C. and was kept at this temperature for 48 h. The reaction mixture was washed with saturated aqueous sodium bicarbonate (2×), brine, dried over magnesium sulfate, and concentrated. Purification via silica gel chromatography using 0-40% ethyl acetate in hexane gave desired prod

General Procedure 10

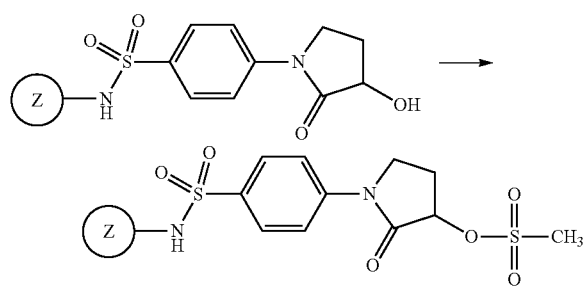

Under an N₂ atmosphere at 0° C., DMAP (1.5-3 equivalent) was added to a solution of alcohol (1 equivalent) in CH₂Cl₂ (0.5 M). To the reaction mixture was then added triethylamine (20 equivalent). Methanesulfonic anhydride (10 equivalent) was added dropwise to this solution at 0° C. Upon completion of addition, the mixture was stirred at RT overnight. The reaction mixture was poured into water and extracted with CH₂Cl₂ (2×), dried over magnesium sulfate, and concentrated. Purification via silica gel chromatography using 2-10% MeOH in CH₂Cl₂ gave mesylated alcohol.

(R)-2-Oxo-1-(4-(N-thiazol-2-ylsulfamoyl)phenyl) pyrrolidin-3-yl methanesulfonate

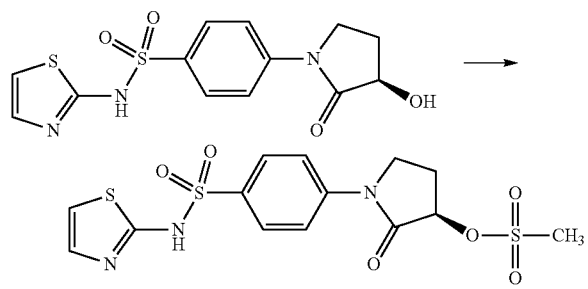

Synthesized according to General procedure 10. LC/MS (10%-99% CH₃CN (0.035% TFA)/H₂O (0.05% TFA)), m/z: M+1 obs=498.3; $t_R$=1.18 min.

General Procedure 11

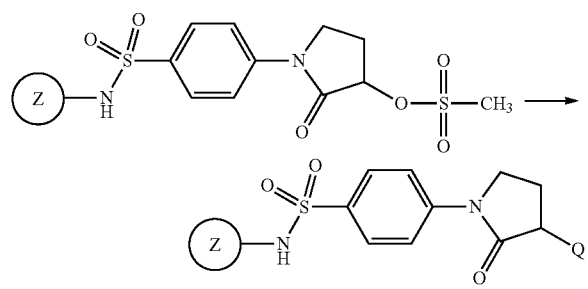

Method A

A solution of mesylate (1 equivalent), triethylamine (3 equivalents), amine (2-5 equivalents) in DMF (0.3-0.5 M) was stirred under an N₂ atmosphere at RT for 19 h. Purification via reverse phase HPLC using 10%-99% CH₃CN (0.035% TFA)/H₂O (0.05% TFA) gave the desired product.

Method B

A solution of mesylate (1 equivalent), potassium fluoride (1 equivalent), amine (2-5 equivalent) in acetonitrile (0.3-0.5 M) was heated under microwave irradiation at 150° C. for 10 min. Purification via reverse phase HPLC using 10%-99% CH₃CN (0.035% TFA)/H₂O (0.05% TFA) gave the desired product.

General Procedure 12

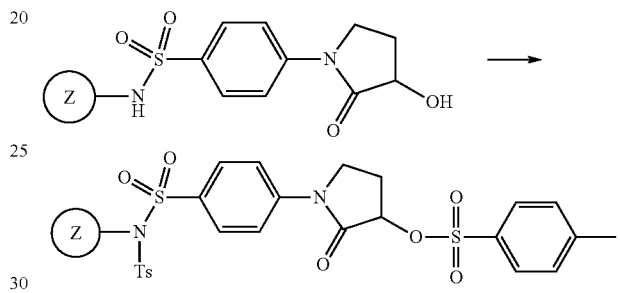

Under an N₂ atmosphere at −20° C., DMAP (1.5-3 equivalent) was added to a solution of alcohol (1 equivalent) in CH₂Cl₂ (0.5 M). To the reaction mixture then added triethylamine (3 equivalents). P-toluenesulfonic anhydride (3 equivalents) was added dropwise to this solution at −20° C. Upon completion of addition, the mixture was stirred at RT overnight. The reaction mixture was poured into water and extracted with CH₂Cl₂ (2×), dried over magnesium sulfate, and concentrated. Purification via silica gel chromatography using 2-10% MeOH in CH₂Cl₂ gave bis tosylated alcohol.

(R)-2-oxo-1-(4-(N-(thiazol-2-yl)-N-tosylsulfamoyl) phenyl)-pyrrolidin-3-yl 4-methylbenzenesulfonate Synthesized according to General procedure 12. LC/MS (10%-99% CH₃CN (0.035% TFA)/H₂O (0.05% TFA)), m/z: M+1 obs=648.5; $t_R$=1.92 min.

General Procedure 13

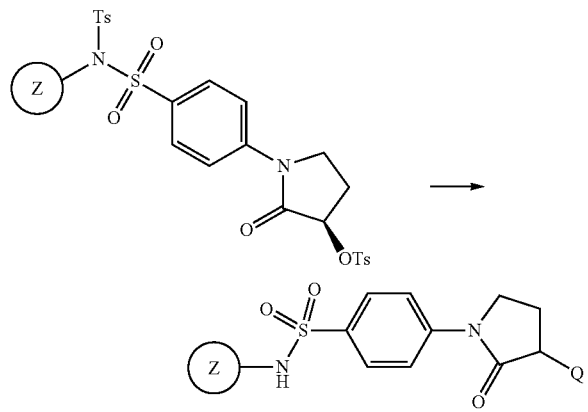

A solution of tosylated alcohol (1 equivalent), triethylamine (4 equivalents), amine (4 equivalents) in DMF (0.3-0.5 M) was stirred under $N_2$ atmosphere at 60° C. for 19 h. Purification via reverse phase HPLC using 10%-99% $CH_3CN$ (0.035% TFA)/$H_2O$ (0.05% TFA) gave the desired product.

4-((S)-3-((R)-2-(3,5-dichlorophenyl)morpholino)-2-oxopyrrolidin-1-yl)-N-(thiazol-2-yl)benzenesulfonamide and 4-((S)-3-((S)-2-(3,5-dichlorophenyl)-morpholino)-2-oxopyrrolidin-1-yl)-N-(thiazol-2-yl)benzenesulfonamide

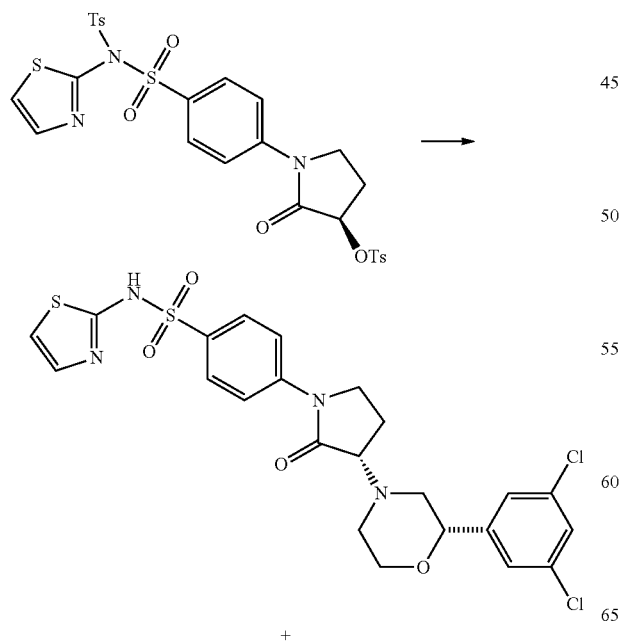

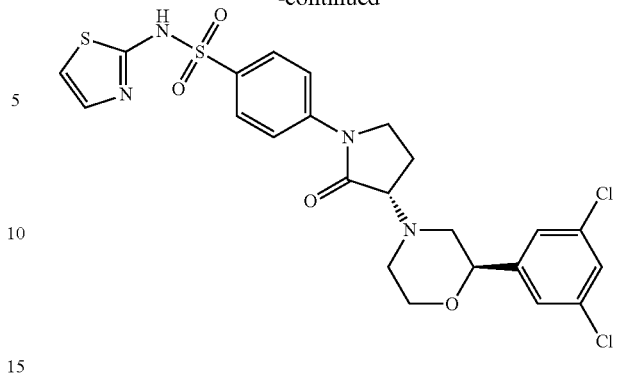

Synthesized according to General procedure 13. A solution of tosylated alcohol (2.0 g, 3 mmol), triethylamine (1.73 mL, 2.4 mmol), 2-(3,5-dichlorophenyl)morpholine (1.99 g, 6.2 mmol) in DMF (20 mL) was stirred under $N_2$ atmosphere at 60° C. for 19 h. Purification via silica gel chromatography using 2-10% methanol in $CH_2Cl_2$ gave 4-((3S)-3-(2-((3,5-dichlorophenyl)morpholino)-2-oxopyrrolidin-1-yl)-N-(thiazol-2-yl)benzenesulfonamide as a white solid (0.282 g, 16.4%). LC/MS (10%-99% $CH_3CN$ (0.035% TFA)/$H_2O$ (0.05% TFA)), m/z: M+1 obs=553.3; $t_R$=1.45 min. The diastereomeric mixture was then purified using supercritical fluid chromatography (Chiralpak AS-H column (2×25 cm), 55% methanol (1% DEA)/$CO_2$, 50 mL/min) to obtain both diastereomers 4-((S)-3((R)-2-((3,5-dichlorophenyl)morpholino)-2-oxopyrrolidin-1-yl)-N-(thiazol-2-yl)benzenesulfonamide (60 mg) and 4-((S)-3((S)-2-((3,5-dichlorophenyl)morpholino)-2-oxopyrrolidin-1-yl)-N-(thiazol-2-yl)benzenesulfonamide (45 mg).

(S, R) diastereomer: $^1$H-NMR (400 MHz, DMSO) δ 12.71 (s, 1H), 7.84-7.77 (m, 4H), 7.54-7.50 (m, 1H), 7.44 (d, J=1.8 Hz, 2H), 7.24 (d, J=4.6 Hz, 1H), 6.82 (d, J=4.6 Hz, 1H), 4.57 (dd, J=1.7, 9.8 Hz, 1H), 3.97-3.91 (m, 1H), 3.79-3.62 (m, 4H), 3.21-3.17 (m, 1H), 2.95-2.86 (m, 2H), 2.69-2.66 (m, 1H), 2.22-2.12 (m, 2H). LC/MS (10%-99% $CH_3CN$ (0.035% TFA)/$H_2O$ (0.05% TFA)), m/z: M+1 obs=553.3; $t_R$=1.45 min. SFC (Chiralpak AS-H, (0.46×25 cm), 55% methanol (1% DEA)/$CO_2$, 3 mL/min): $t_R$=5.6 min.

(S, S) diastereomer: $^1$H-NMR (400 MHz, DMSO) δ 7.85-7.78 (m, 4H), 7.54 (t, J=1.9 Hz, 1H), 7.42 (d, J=1.8 Hz, 2H), 7.25 (d, J=4.6 Hz, 1H), 6.82 (d, J=4.6 Hz, 1H), 4.53 (dd, J=1.9, 9.9 Hz, 1H), 3.97 (d, J=9.9 Hz, 1H), 3.80-3.65 (m, 4H), 3.01-2.89 (m, 2H), 2.70-2.65 (m, 1H), 2.51-2.45 (m, 1H), 2.27-2.22 (m, 1H), 2.12-2.07 (m, 1H). LC/MS (10%-99% $CH_3CN$ (0.035% TFA)/$H_2O$ (0.05% TFA)), m/z: M+1 obs=553.3; $t_R$=1.44 min. SFC (Chiralpak AS-H, (0.46×25 cm), 55% methanol (1% DEA)/$CO_2$, 3 mL/min): $t_R$=6.8 min.

Route 3

General Procedure 14

Under an $N_2$ atmosphere at –20° C., N,N-diisopropylethylamine (3 eq) was added dropwise to a solution of solution of α-hydroxy-γ-butyrolactone (1 eq) in dichloromethane (0.5 mL). Then added trifluoromethanesulfonic anhydride (1-1.2 eq) dropwise by maintaining internal temperature of the reaction mixture <–20° C. Upon completion of addition, the mixture was stirred at –20° C. for 1 hour. Then added at –20° C., amine (1.5 eq) dropwise. The reaction was allowed to warm to RT over a period of 30 minutes and continued to stir at RT for 16 hrs. The reaction mixture was diluted with 200 mL of ethylacetate and washed with saturated sodium bicarbonate (3×). The organic layer was washed with a saturated aqueous NaCl solution (2×). The solution was dried over magnesium sulfate, filtered, and concentrated. Purification via silica gel chromatography using 10-30% ethyl acetate in hexane gave desired product.

General Procedure 15

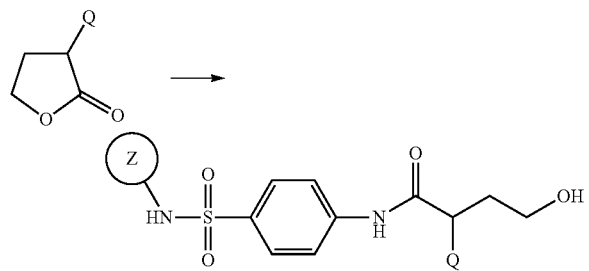

To a solution of sulfathiazole (1-1.2 eq.) in $CH_2Cl_2$ (0.5 M) under nitrogen at RT was added a solution of trimethylaluminum in hexane (2.0M, 1-1.2 eq.) over 5 min. After stirring at RT for 20 min, a solution of the lactone (1 eq.) in $CH_2Cl_2$ (0.4 M) was added over 10 min. Stirring was continued for 18-36 h at RT or reflux, then the reaction mixture was cooled to 0° C. and quenched by careful addition of aqueous 1M HCl. Phases were separated, and the aqueous phase was extracted with $CH_2Cl_2$ (2×). The combined organic extracts were dried over $MgSO_4$ and concentrated. Purification via silica gel chromatography using 2-10% MeOH in $CH_2Cl_2$ gave the desired products.

General Procedure 16

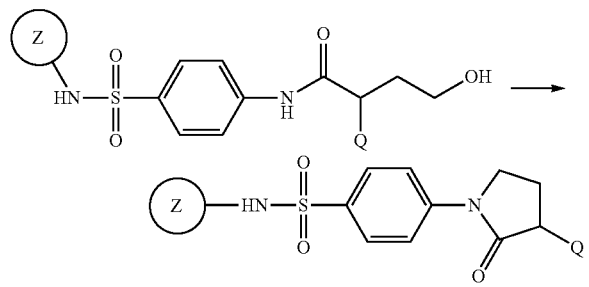

To a yellow solution of di-tert-butyl azo-dicarboxylate (2-4 eq.) in THF (0.4 M) at 0° C. under $N_2$ was slowly added tributylphosphine (2-4 eq.), The resulting colorless solution of the Mitsunobu reagent was stirred at RT for 10 min, and then added to a solution of the amidoalcohol (1 eq.) in THF (0.3 M) at 0° C. under $N_2$. The reaction mixture was stirred for 10 min. at this temperature, and quenched by addition of a saturated aqueous $NaHCO_3$ solution. EtOAc was added, the phases were separated, and the aqueous layer was extracted with EtOAc (2×). The combined organic extracts were dried over $MgSO_4$ and concentrated. Purification via silica gel chromatography using EtOAc in hexane gave the desired products.

General Procedure 17

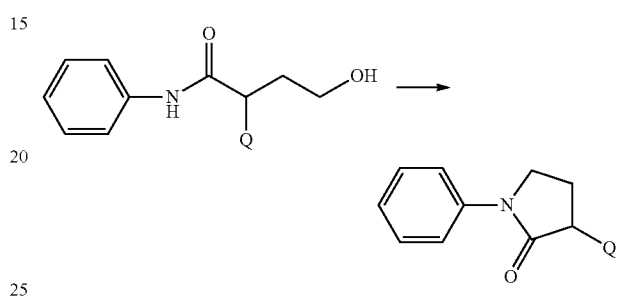

To a yellow solution of di-tert-butyl azo-dicarboxylate (2-4 eq.) in THF (0.4 M) at 0° C. under $N_2$ was slowly added tributylphosphine (2-4 eq.), The resulting colorless solution of the Mitsunobu reagent was stirred at RT for 10 min, and then added to a solution of the amido alcohol (1 eq.) in THF (0.3 M) at 0° C. under $N_2$. The reaction mixture was stirred for 10 min. at this temperature, and quenched by addition of a saturated aqueous $NaHCO_3$ solution. EtOAc was added, the phases were separated, and the aqueous layer was extracted with EtOAc (2×). The combined organic extracts were dried over $MgSO_4$ and concentrated. Purification via silica gel chromatography using EtOAc in hexane gave the desired products.

General Procedure 18

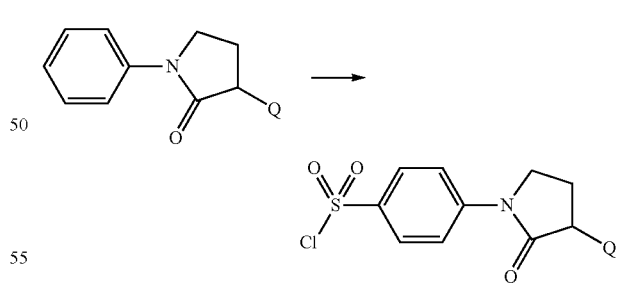

To chlorosulfonic acid (5-30 eq.) at 0° C. under $N_2$ was added the phenyl-pyrrolidin-2-one (1 eq.) in portions. The reaction mixture was heated to 50-60° C. for 15-20 min. and, after cooling to RT, carefully poured onto ice-water. EtOAc or $CH_2Cl_2$ were added, the phases were separated, and the aqueous layer was extracted with EtOAc or $CH_2Cl_2$ (2×). The combined organic extracts were dried over $MgSO_4$ and concentrated. Purification via silica gel chromatography using EtOAc in hexane gave the desired products.

General Procedure 19

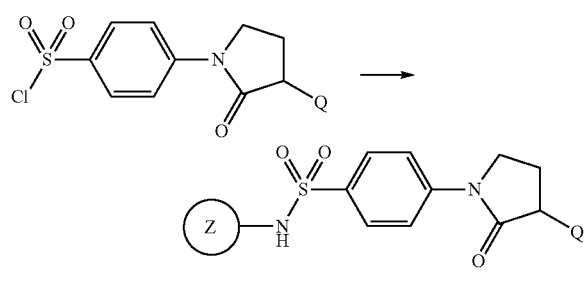

Method A

A solution of the sulfonyl chloride (1 eq.), 2-tert-butyl-1,1,3,3-tetramethylguanidine (5 eq.), and thiazole or thiadiazole amine (1 eq.) in acetonitrile (0.3-0.5 M) was stirred under an $N_2$ atmosphere at RT for 19 h. Purification via reverse phase HPLC using 10%-99% $CH_3CN$ (0.035% TFA)/$H_2O$ (0.05% TFA) gave the desired products.

Method B

A solution of the sulfonyl chloride (1 eq.), DABCO (5 eq.), and thiazole or thiadiazole amine (1 eq.) in acetonitrile (0.3-0.5 M) was stirred under an $N_2$ atmosphere at RT for 19 h. Purification via reverse phase HPLC using 10%-99% $CH_3CN$ (0.035% TFA)/$H_2O$ (0.05% TFA) gave the desired product.

Method C

A solution of the sulfonyl chloride (1 eq.), and thiazole or thiadiazole amine (1 eq.) in pyridine (0.3-0.5 M) was stirred under an $N_2$ atmosphere at RT for 19 h. Purification via reverse phase HPLC using 10%-99% $CH_3CN$ (0.035% TFA)/$H_2O$ (0.05% TFA) gave the desired product.

Method D

A solution of the sulfonyl chloride (1 eq.), phosphazene base P1-t-Bu-tris(tetramethylene) (5 eq.), and thiazole or thiadiazole amine (1 eq.) in acetonitrile (0.3-0.5 M) was stirred under an $N_2$ atmosphere at RT for 19 h. Purification via reverse phase HPLC using 10%-99% $CH_3CN$ (0.035% TFA)/$H_2O$ (0.05% TFA) gave the desired product.

General Procedure 20

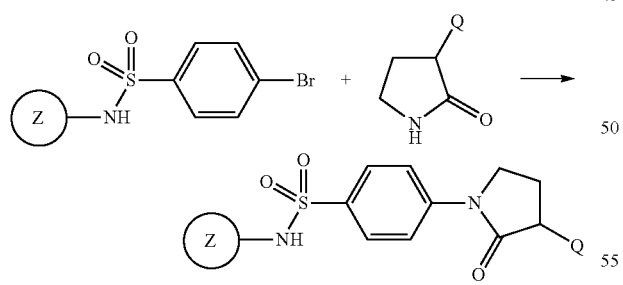

4-Bromo-benzenesulfonamide (1 eq.), pyrrolidin-2-one (1.2 eq.), copper (I) iodide (10 mol %), N,N'-dimethylethylenediamine (20 mol %), and $K_2CO_3$ (4 eq.) were combined in a microwave vial and set under nitrogen. NMP (0.4 M) was added, and the reaction mixture was heated to 200° C. for 30 min. using microwave irradiation. After cooling to RT, the reaction mixture was diluted with DMSO/MeOH (1:1) and purified via reverse phase HPLC using 10%-99% $CH_3CN$ (0.035% TFA)/$H_2O$ (0.05% TFA) to give the desired products.

Route 4

(R)—S-Ethyl 2-(2,2-dimethyl-5-oxo-1,3-dioxolan-4-yl)ethanethioate

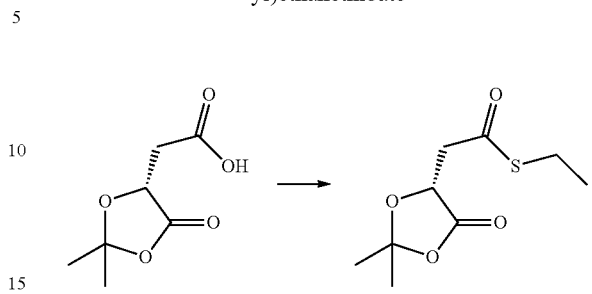

To a stirring suspension of (R)-(−)-dimethyl-5-oxo-1,2-dioxolane-4-acetic acid (3.5 g, 20 mmol), and $CH_2Cl_2$ (40 mL), at 0° C., under $N_2$, was added isovalerylchloroformate (2.9 mL, 22 mmol) dropwise over 5 minutes. The mixture was stirred at 0° C. for 10 minutes. Triethylamine (5.5 mL, 40 mmol) was added dropwise at 0° C. followed by the dropwise addition of ethanethiol (3.4 mL, 44 mmol). The pink mixture was stirred at 0° C. for 10 minutes. To the reaction was added $Et_2O$ (40 mL) and the mixture was filtered. The filtrate was washed with 1.0 N aqueous HCl (20 mL), 0.1 N aqueous NaOH (20 mL), $H_2O$ (20 mL) and brine (20 mL). The organic solution was evaporated to dryness under reduced pressure to obtain the desired thioester as a clear oil (3.4 g, 16 mmol, 82% yield). $^1$H NMR (400 MHz, CDCl3) δ 4.71-4.65 (m, 1H), 3.91-3.81 (m, 1H), 3.11-2.70 (m, 3H), 1.53 (s, 3H), 1.50 (s, 3H), 0.87-0.86 (m, 3H). LC/MS (10%-99% $CH_3CN$ (0.035% TFA)/$H_2O$ (0.05% TFA)), m/z: M+1 obs=219.4; $t_R$=1.33 min.

General Procedure 21

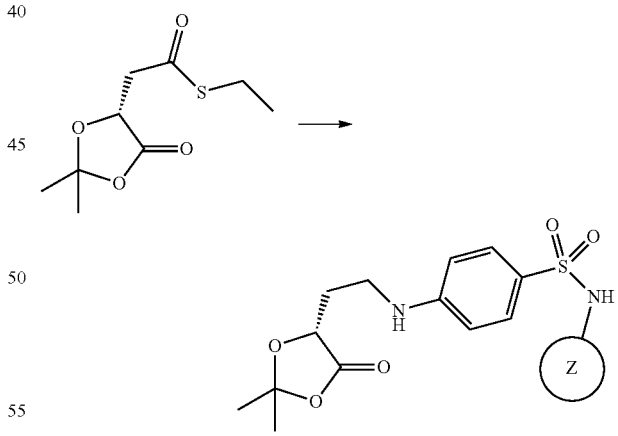

To a stirring mixture of (R)—S-ethyl 2-(2,2-dimethyl-5-oxo-1,3-dioxolan-4-yl)ethanethioate (1 equivalent), 10% palladium on carbon (470 mg), and $CH_2Cl_2$ (0.5-1 M) under $N_2$, at 25° C., was added triethylsilane (1.5 equivalent) dropwise over 10 minutes. The mixture was stirred at 25° C. for 1 hour. The mixture was filtered and the filtrate was evaporated to dryness under reduced pressure to give the desired aldehyde as clear oil. The aldehyde was added to a stirring mixture of sulfathiazole (0.5 equivalent), MeOH (1 M), and trifluoroacetic acid (0.1 M). To this solution was added sodium borohydride (2.5 equivalent) portionwise over 10 minutes. The mixture was stirred for 10 minutes and evaporated under reduced pressure. The residue was purified via silica gel chromatography using 5% MeOH in CH$_2$Cl$_2$ to obtain the desired amine.

(R)-4-(2-(2,2-Dimethyl-5-oxo-1,3-dioxolan-4-yl) ethylamino)-N-(thiazol-2-yl)benzenesulfonamide

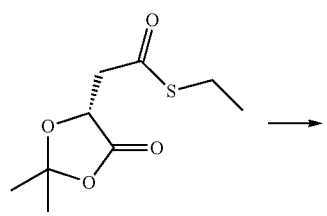

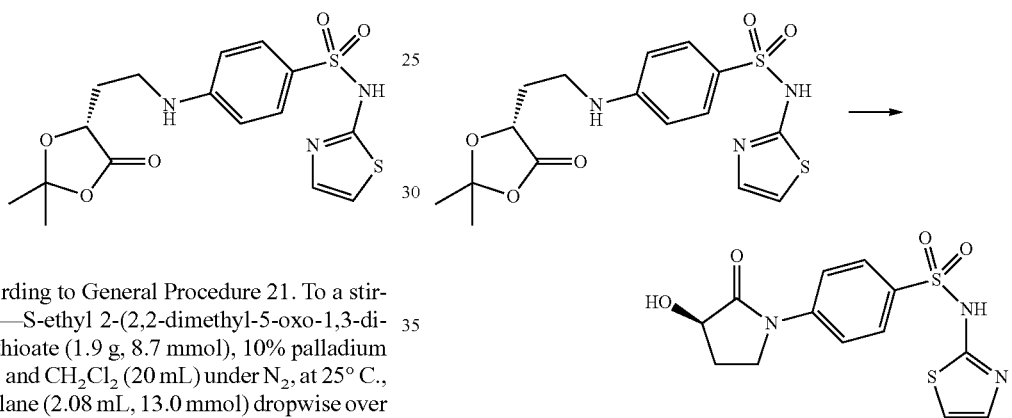

Synthesized according to General Procedure 21. To a stirring mixture of (R)—S-ethyl 2-(2,2-dimethyl-5-oxo-1,3-dioxolan-4-yl)ethanethioate (1.9 g, 8.7 mmol), 10% palladium on carbon (470 mg), and CH$_2$Cl$_2$ (20 mL) under N$_2$, at 25° C., was added triethylsilane (2.08 mL, 13.0 mmol) dropwise over 10 minutes. The mixture was stirred at 25° C. for 1 hour. The mixture was filtered and the filtrate was evaporated to dryness under reduced pressure to give the desired aldehyde as a clear oil (1.2 g). The aldehyde was added to a stirring mixture of sulfathiazole (1.1 g, 4.3 mmol), MeOH (25 mL), and trifluoroacetic acid (2.5 mL). To this solution was added sodium borohydride (813 mg, 21.4 mmol) portionwise over 10 minutes. The mixture was stirred for 10 minutes and evaporated under reduced pressure. The residue was purified via silica gel chromatography using 5% MeOH in CH$_2$Cl$_2$ to obtain the desired amine as a white solid (1.5 g, 3.9 mmol, 45% yield). LC/MS (10%-99% CH$_3$CN (0.035% TFA)/H$_2$O (0.05% TFA)), m/z: M+1 obs=398.3; t$_R$=1.18 min.

General Procedure 22

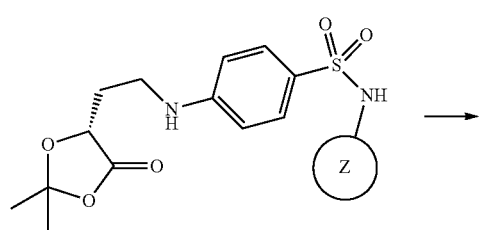

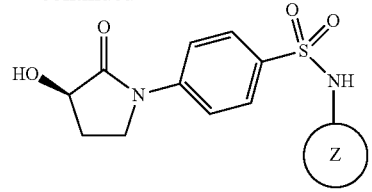

A stirring solution of benzenesulfonamide (1 equivalent), p-toluenesulfonic acid monohydrate (0.1 equivalent), and THF (0.5-1 M) was stirred at 80° C. for 3 hours. The mixture was concentrated to dryness under reduced pressure. The residue was purified via silica gel chromatography using 5% MeOH in CH$_2$Cl$_2$ to give the desired lactam.

(R)-4-(3-Hydroxy-2-oxopyrrolidin-1-yl)-N-(thiazol-2-yl)benzenesulfonamide

Synthesized according to General Procedure 22. A stirring solution of (R)-4-(2-(2,2-dimethyl-5-oxo-1,3-dioxolan-4-yl) ethylamino)-N-(thiazol-2-yl)benzene-sulfonamide (833 mg, 2.15 mmol), p-toluenesulfonic acid monohydrate (42 mg, 0.22 mmol), and THF (10 mL) was stirred at 80° C. for 3 hours. The mixture was concentrated to dryness under reduced pressure. The residue was purified via silica gel chromatography using 5% MeOH in CH$_2$Cl$_2$ to give the desired lactam as a white solid (496 g, 1.4 mmol, 65% yield). $^1$H NMR (400 MHz, DMSO-d6) δ 7.85 (dd, J=2.1, 6.9 Hz, 4H), 7.25 (d, J=4.6 Hz, 1H), 6.82 (d, J=4.6 Hz, 1H), 5.83 (d, J=5.9 Hz, 1H), 4.32 (d, J=5.3 Hz, 1H), 3.77 (dd, J=1.9, 9.0 Hz, 1H), 3.71-3.69 (m, 1H), 2.41-2.38 (m, 1H), 1.84 (dd, J=9.2, 12.3 Hz, 1H).). LC/MS (10%-99% CH$_3$CN (0.035% TFA)/H$_2$O (0.05% TFA)), m/z: M+1 obs=340.2; t$_R$=0.50 min.

General Procedure 23

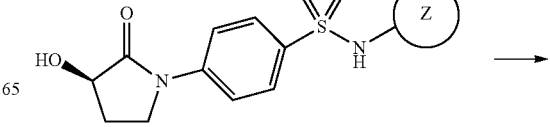

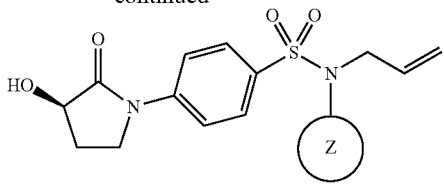

To a stirring suspension of N-benzenesulfonamide (1 equivalent) in CH$_2$Cl$_2$ (0.5-1 M), under N$_2$, at 0° C., was added N,N-diisopropylethylamine (1 equivalent) followed by allylbromide (1 equivalent). The mixture was stirred at ambient temperature for 19 hours. The mixture was evaporated to dryness under reduced pressure. The residue was purified via silica gel using 50% EtOAc in hexanes to give the desired sulfonamide.

(R)—N-Allyl-4-(3-hydroxy-2-oxopyrrolidin-1-yl)-N-(thiazol-2-yl)benzenesulfonamide

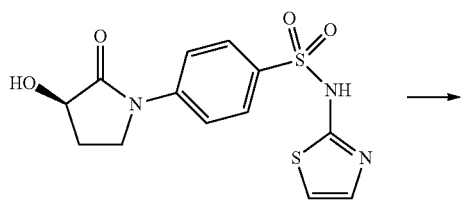

Synthesized according to General Procedure 23. To a stirring suspension of (R)-4-(3-hydroxy-2-oxopyrrolidin-1-yl)-N-(thiazol-2-yl)benzenesulfonamide (200 mg, 0.59 mmol) in CH$_2$Cl$_2$ (0.50 mL), under N$_2$, at 0° C., was added N,N-diisopropylethylamine (0.10 mL, 0.59 mmol) followed by allylbromide (51 uL, 0.59 mmol). The mixture was stirred at ambient temperature for 19 hours. The mixture was evaporated to dryness under reduced pressure. The residue was purified via silica gel using 50% EtOAc in hexanes to give the desired sulfonamide as a white solid (220 mg, 0.57 mmol, 96% yield). $^1$H NMR (400 MHz, DMSO-d6) δ 7.86-7.80 (m, 4H), 7.37 (d, J=4.7 Hz, 1H), 6.93 (d, J=4.7 Hz, 1H), 5.92-5.83 (m, 2H), 5.17 (dd, J=1.3, 10.3 Hz, 1H), 4.98 (q, J=1.4 Hz, 1H), 4.55 (dt, J=5.3, 1.7 Hz, 2H), 4.36-4.30 (m, 1H), 3.81-3.76 (m, 1H), 3.70 (td, J=9.5, 5.4 Hz, 1H), 2.45-2.38 (m, 1H), 1.90-1.80 (m, 1H).

General Procedure 24

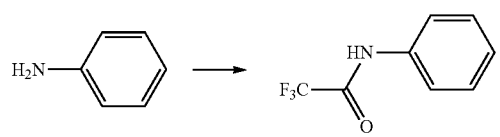 [SMILES: Nc1ccccc1 ; O=C(Nc1ccccc1)C(F)(F)F]

Under an N$_2$ atmosphere at −78° C., 2,2,2-trifluoroacetic anhydride (1 equivalent) was added drop wise to a solution of the aniline (1 equivalent), triethylamine (1 equivalent), and CH$_2$Cl$_2$ (0.6 M). The reaction was allowed to warm to RT over a period of 30 minutes. After evaporating the solvents under reduced pressure, purification via silica gel chromatography using 7/3 hexanes/EtOAc gave desired product.

General Procedure 25

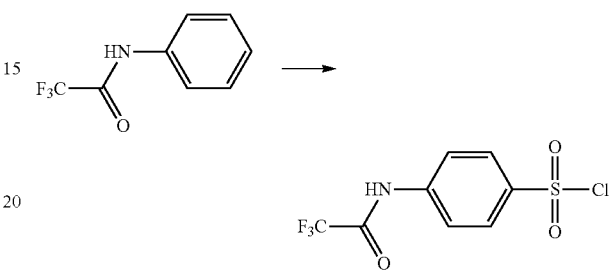

A mixture of acetamide (1 equivalent) and chlorosulfonic acid (5 equivalent) was heated at 155° C. for 15 min. After cooling to RT, the mixture was poured into ice water and extracted with EtOAc. The organic layer was concentrated and purified via silica gel chromatography using 7/3 hexanes/EtOAc gave desired product.

General Procedure 26

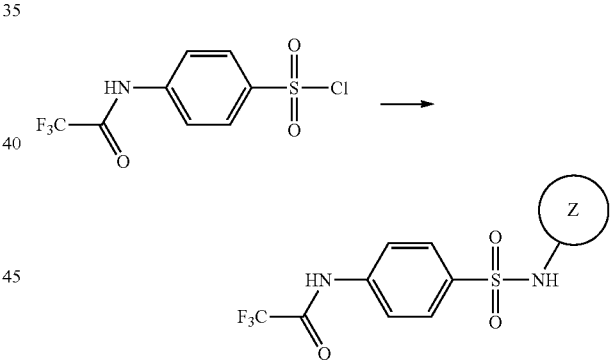

Under an N$_2$ atmosphere, a mixture of the sulfonyl chloride (1 mmol) and aminoheterocycle (1 mmol), and pyridine (1.0 mL) was stirred at RT for 19 h. The crude product was purified via silica gel chromatography using MeOH in CH$_2$Cl$_2$.

General Procedure 27

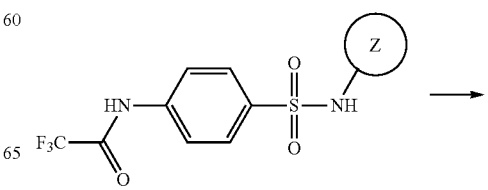

-continued

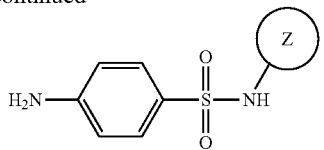

A solution of sulfonamide (1 equivalent), NaOH (10 equivalents), and H₂O (0.25 M) was stirred at RT for 1 h, then cooled to 0° C. Acetic acid (10 equivalents) was added, and the reaction was stirred at 0° C. for 20 min. The formed precipitate was filtered off and dried under vacuum to give the desired product.

General Procedure 28

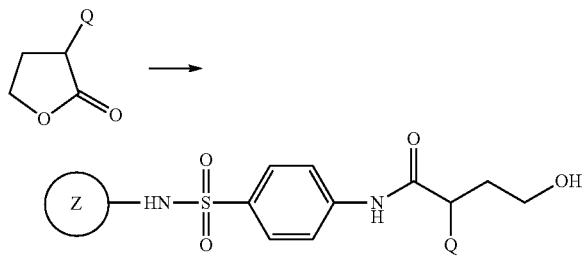

To a solution of sulfathiazole (1-1.2 eq.) in CH₂Cl₂ (0.5 M) under nitrogen at RT was added a solution of trimethylaluminum in hexane (2.0M, 1-1.2 eq.) over 5 min. After stirring at RT for 20 min, a solution of the lactone (1 eq.) in CH₂Cl₂ (0.4 M) was added over 10 min. Stirring was continued for 18-36 h at RT or reflux, then the reaction mixture was cooled to 0° C. and quenched by careful addition of aqueous 1M HCl. Phases were separated, and the aqueous phase was extracted with CH₂Cl₂ (2×). The combined organic extracts were dried over MgSO₄ and concentrated. Purification via HPLC gave the desired product.

General Procedure 29

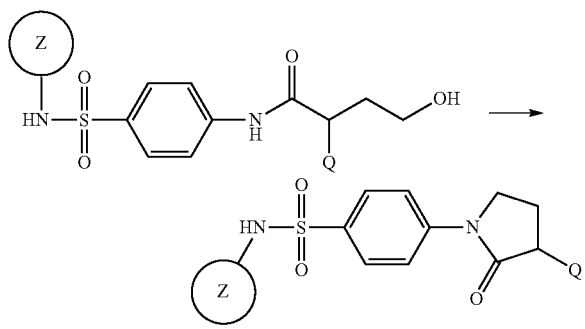

To a yellow solution of di-tert-butyl azo-dicarboxylate (2-4 eq.) in THF (0.4 M) at 0° C. under N₂ was slowly added tributylphosphine (2-4 eq.), The resulting colorless solution of the Mitsunobu reagent was stirred at RT for 10 min, and then added to a solution of the amidoalcohol (1 eq.) in THF (0.3 M) at 0° C. under N₂. The reaction mixture was stirred for 10 min. at this temperature, and quenched by addition of a saturated aqueous NaHCO₃ solution. EtOAc was added, the phases were separated, and the aqueous layer was extracted with EtOAc (2×). The combined organic extracts were dried over MgSO₄ and concentrated. Purification via Gilson HPLC gave the desired product.

Route 5

General Procedure 30

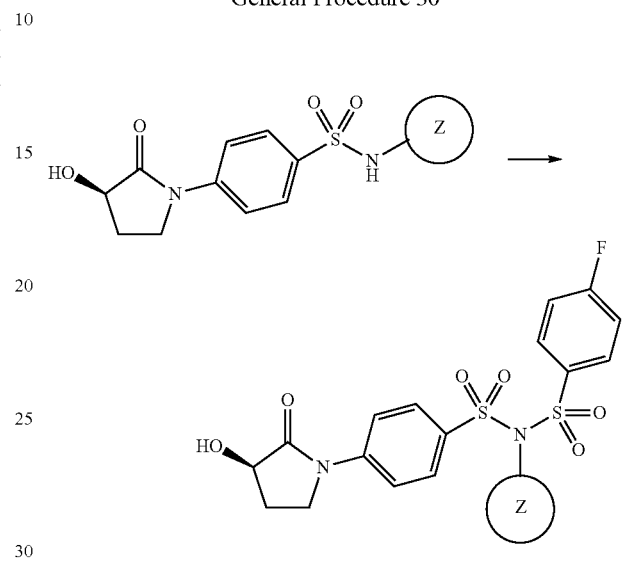

To a stirring solution of sulfonamide (1 eq.) and DMF (0.6 M), under N₂, at 5° C. (ice bath) was added N,N-diisopropylethylamine (1 eq.). To this solution was added 4-fluorobenzenesulfonyl chloride (1 eq.) portionwise over 10 minutes. The solution was stirred at ambient temperature for 20 minutes. To this solution was added MeOH. The mixture was cooled to 5° C. via an ice bath and stirred for 30 minutes. The resulting precipitate was filtered, washed with MeOH, and vacuum dried to afford the desired bissulfonamide.

(R)-4-fluoro-N-(4-(3-hydroxy-2-oxopyrrolidin-1-yl)phenylsulfonyl)-N-(thiazol-2-yl)benzenesulfonamide

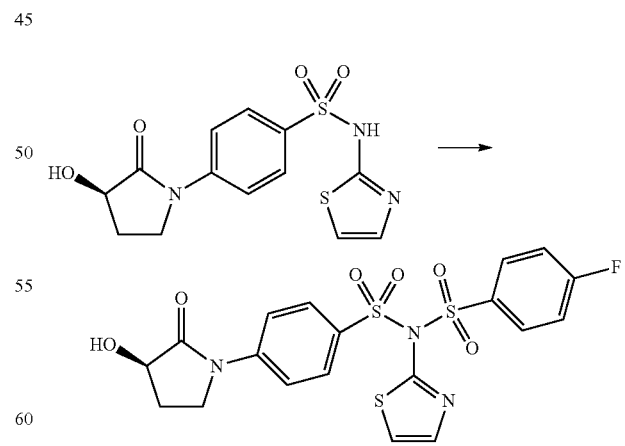

Synthesized according to General Procedure 30. To a stirring solution of (R)-4-(3-hydroxy-2-oxopyrrolidin-1-yl)-N-(thiazol-2-yl)benzenesulfonamide (5.0 g, 14.8 mmol) and DMF (25 mL), under N₂, at 5° C. (ice bath) was added diisopropylethyamine (2.5 mL, 14.8 mmol). To this solution was added 4-fluorobenzenesulfonyl chloride (2.9 g, 14.8 mmol) portionwise over 10 minutes. The solution was stirred at ambient temperature for 20 minutes. To this solution was added MeOH (75 mL). The mixture was cooled to 5° C. via an ice bath and stirred for 30 minutes. The precipitate was filtered, washed with MeOH (20 mL), and vacuum dried to give the desired sulfonamide as a white solid (6.5 g, 13.1 mmol, 89% yield). $^1$H-NMR (400 MHz, DMSO) δ 8.03-7.96 (m, 2H), 7.83-7.80 (m, 2H), 7.72 (d, J=5.1 Hz, 1H), 7.61 (dd, J=1.8, 7.1 Hz, 1H), 7.59 (s, 1H), 7.37 (s, 1H), 7.37 (dd, J=2.0, 15.6 Hz, 1H), 7.02 (d, J=5.1 Hz, 1H), 5.88 (d, J=5.9 Hz, 1H), 4.38-4.32 (m, 1H), 3.83-3.78 (m, 1H), 3.71 (td, J=9.5, 5.4 Hz, 1H), 2.52-2.42 (m, 1H), 1.87 (td, J=9.4, 4.1 Hz, 1H). LC/MS (10%-99% CH$_3$CN (0.035% TFA)/H$_2$O (0.05% TFA)), m/z: M+1 obs=498.3; $t_R$=1.32 min.

General Procedure 31

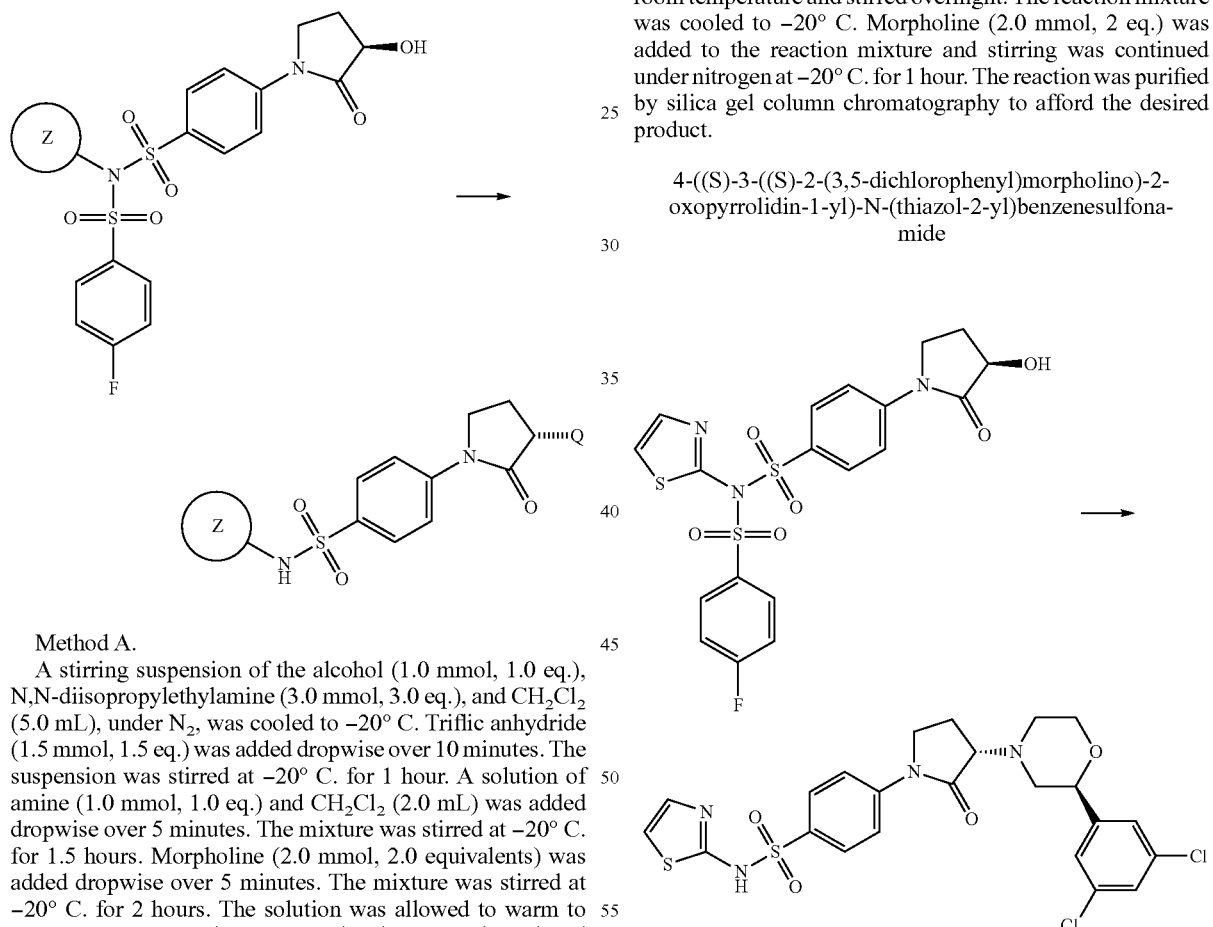

Method A.

A stirring suspension of the alcohol (1.0 mmol, 1.0 eq.), N,N-diisopropylethylamine (3.0 mmol, 3.0 eq.), and CH$_2$Cl$_2$ (5.0 mL), under N$_2$, was cooled to −20° C. Triflic anhydride (1.5 mmol, 1.5 eq.) was added dropwise over 10 minutes. The suspension was stirred at −20° C. for 1 hour. A solution of amine (1.0 mmol, 1.0 eq.) and CH$_2$Cl$_2$ (2.0 mL) was added dropwise over 5 minutes. The mixture was stirred at −20° C. for 1.5 hours. Morpholine (2.0 mmol, 2.0 equivalents) was added dropwise over 5 minutes. The mixture was stirred at −20° C. for 2 hours. The solution was allowed to warm to room temperature and concentrated to dryness under reduced pressure. The residue was purified via silica gel chromatography to obtain the desired product.

Method B.

A stirring suspension of the alcohol (1.0 mmol, 1 eq.), N,N-diisopropylethylamine (2.0 mmol, 2 eq.), and CH$_2$Cl$_2$ (7.5 mL), under N$_2$, was cooled to −40° C. Triflic anhydride (1.1 mmol, 1.1 eq.) was added dropwise over 10 minutes. The suspension was stirred at −40° C. for 1 hour. A solution of the amine (1.5 mmol, 1.5 eq.) and CH$_2$Cl$_2$ (0.5 mL) was added dropwise over 10 minutes. The mixture was allowed to slowly warm to room temperature over 6 hours. Water (20 μL) was added and the mixture was filtered through a bed of silica gel (5 g) followed by CH$_2$Cl$_2$ (20 mL). The filtrate was evaporated to dryness under reduced pressure. The residue was dissolved in anhydrous THF (5 mL). To this stirring solution, under N$_2$, at 25° C., was added tetrabutylammonium fluoride (1.0 M in THF, 1.0 mmol, 1 eq.) in a single portion. The solution was stirred at 25° C. for 30 minutes and then concentrated to dryness under reduced pressure. The residue was purified via silica gel chromatography to afford the product.

Method C.

A solution of the alcohol (1.0 mmol, 1 eq.) in DCM (5 mL) was stirred under nitrogen at −20° C. To the reaction mixture was added N,N-diisopropylethyl amine (2.0 mmol, 2 eq.) followed by dropwise addition of triflic anhydride (1.2 mmol, 1.2 eq.). The reaction was stirred at −20° C. for 1 hour. A solution of the amine (1.5 mmol, 1.5 eq.) and sodium hydride (60% dispersion in mineral oil, 0.9 mmol, 0.9 eq.) in DCM (1.25 mL) was added to the reaction mixture and stirring was continued at −20° C. The reaction was allowed to warm to room temperature and stirred overnight. The reaction mixture was cooled to −20° C. Morpholine (2.0 mmol, 2 eq.) was added to the reaction mixture and stirring was continued under nitrogen at −20° C. for 1 hour. The reaction was purified by silica gel column chromatography to afford the desired product.

4-((S)-3-((S)-2-(3,5-dichlorophenyl)morpholino)-2-oxopyrrolidin-1-yl)-N-(thiazol-2-yl)benzenesulfonamide Synthesized according to General procedure 31, Method A. A stirring suspension of ((R)-4-fluoro-N-(4-(3-hydroxy-2-oxopyrrolidin-1-yl)phenylsulfonyl)-N-(thiazol-2-yl)benzenesulfonamide (1.07 g, 2.15 mmol), N,N-diisopropylethylamine (1.15 mL, 6.50 mmol), and CH$_2$Cl$_2$ (10.0 mL), under N$_2$, was cooled to −20° C. Triflic anhydride (545 μL, 3.25 mmol) was added dropwise over 10 minutes. The suspension was stirred at −20° C. for 1 hour. A solution of (S)-2-(3,5-dichlorophenyl)morpholine (500 mg, 2.15 mmol) [this enantiomer of 2-(3,5-dichlorophenyl)morpholine was obtained by preparative SFC separation of its racemic mixture: Chiralpak AD-H column (2×15 cm), 50% ethanol (0.1% DEA)/CO$_2$, 50 mL/min)] and CH$_2$Cl$_2$ (2.0 mL) was added dropwise over 5 minutes. The mixture was stirred at −20° C. for 1.5 hours. Morpholine (375 μL, 4.30 mmol) was added dropwise over 5 minutes. The mixture was stirred at −20° C. for 2 hours. The solution was allowed to warm to room temperature and concentrated to dryness under reduced pressure. The residue was purified via silica gel chromatography using 2% MeOH in CH$_2$Cl$_2$ to obtain the desired lactam as a white solid (814 mg, 1.48 mmol, 69% yield). $^1$H-NMR (400 MHz, DMSO) δ 7.85-7.78 (m, 4H), 7.54 (t, J=1.9 Hz, 1H), 7.42 (d, J=1.8 Hz, 2H), 7.25 (d, J=4.6 Hz, 1H), 6.82 (d, J=4.6 Hz, 1H), 4.53 (dd, J=1.9, 9.9 Hz, 1H), 3.97 (d, J=9.9 Hz, 1H), 3.80-3.65 (m, 4H), 3.01-2.89 (m, 2H), 2.70-2.65 (m, 1H), 2.51-2.45 (m, 1H), 2.27-2.22 (m, 1H), 2.12-2.07 (m, 1H). LC/MS (10%-99% CH$_3$CN (0.035% TFA)/H$_2$O (0.05% TFA)), m/z: M+1 obs=553.3; $t_R$=1.44 min. SFC (Chiralpak AS-H, (0.46×25 cm), 55% methanol (1% DEA)/CO$_2$, 3 mL/min): $t_R$=6.8 min.

4-((S)-3-((R)-2-(3,5-dichlorophenyl)morpholino)-2-oxopyrrolidin-1-yl)-N-(thiazol-2-yl)benzenesulfonamide

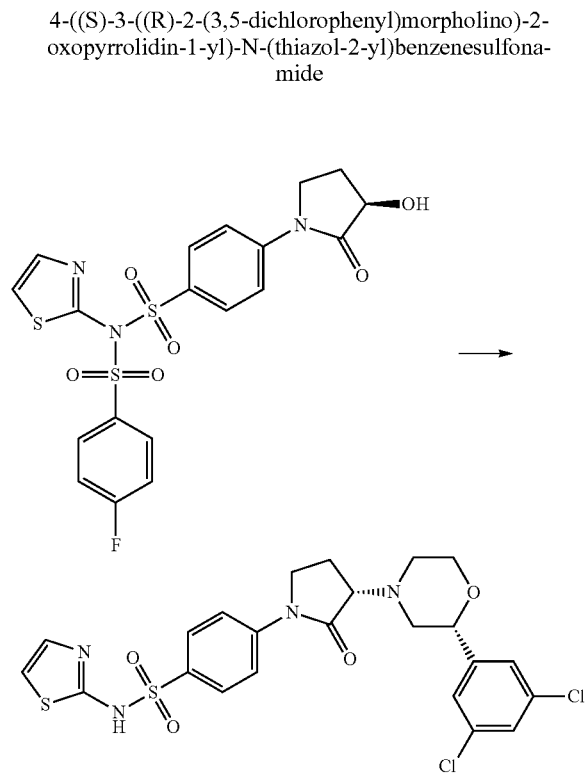

Synthesized according to General procedure 31, Method A. A stirring suspension of ((R)-4-fluoro-N-(4-(3-hydroxy-2-oxopyrrolidin-1-yl)phenylsulfonyl)-N-(thiazol-2-yl)benzenesulfonamide (500 mg, 1.00 mmol), N,N-diisopropylethylamine (465 μL, 3.00 mmol), and CH$_2$Cl$_2$ (5.0 mL), under N$_2$, was cooled to −20° C. Triflic anhydride (220 μL, 1.3 mmol) was added dropwise over 10 minutes. The suspension was stirred at −20° C. for 1 hour. A solution of (R)-2-(3,5-dichlorophenyl)morpholine (248 mg, 1.00 mmol) [this enantiomer of 2-(3,5-dichlorophenyl)morpholine was obtained by preparative SFC separation of its racemic mixture: Chiralpak AD-H column (2×25 cm), 50% ethanol (0.1% DEA)/CO$_2$, 50 mL/min)] and CH$_2$Cl$_2$ (1.0 mL) was added dropwise over 5 minutes. The mixture was stirred at −20° C. for 1.5 hours. Morpholine (174 μL, 2.0 mmol) was added dropwise over 5 minutes. The mixture was stirred at −20° C. for 2 hours. The solution was allowed to warm to room temperature and concentrated to dryness under reduced pressure. The residue was purified via silica gel chromatography using 2% MeOH in CH$_2$Cl$_2$ to obtain the desired lactam as a white solid (420 mg, 0.76 mmol, 76% yield). $^1$H-NMR (400 MHz, DMSO) δ 12.71 (s, 1H), 7.84-7.77 (m, 4H), 7.54-7.50 (m, 1H), 7.44 (d, J=1.8 Hz, 2H), 7.24 (d, J=4.6 Hz, 1H), 6.82 (d, J=4.6 Hz, 1H), 4.57 (dd, J=1.7, 9.8 Hz, 1H), 3.97-3.91 (m, 1H), 3.79-3.62 (m, 4H), 3.21-3.17 (m, 1H), 2.95-2.86 (m, 2H), 2.69-2.66 (m, 1H), 2.22-2.12 (m, 2H). LC/MS (10%-99% CH$_3$CN (0.035% TFA)/H$_2$O (0.05% TFA)), m/z: M+1 obs=553.3; $t_R$=1.45 min. SFC (Chiralpak AS-H, (0.46×25 cm), 55% methanol (1% DEA)/CO$_2$, 3 mL/min): $t_R$=5.6 min.

4-((S)-3-((R)-2-(3,4-dichlorophenyl)morpholino)-2-oxopyrrolidin-1-yl)-N-(thiazol-2-yl)benzenesulfonamide

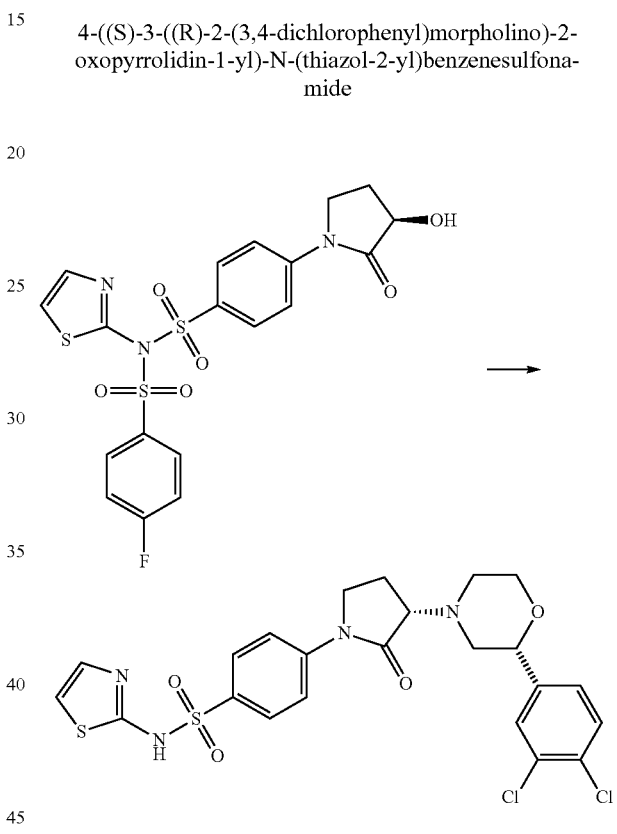

Synthesized according to General procedure 31, Method A. To a solution of (R)-4-fluoro-N-(4-(3-hydroxy-2-oxopyrrolidin-1-yl)phenylsulfonyl)-N-(thiazol-2-yl)benzene-sulfonamide (540 mg, 1.10 mmol) in anhydrous DCM (5.0 mL) at −20° C. under nitrogen, were successively added DIEA (0.57 mL, 3.24 mmol) followed by triflic anhydride (460 mg, 0.27 mL, 1.62 mmol) dropwise. The mixture was stirred at this temperature for 1 h, then (R)-2-(3,4-dichlorophenyl)morpholine (250 mg, 1.08 mmol) was added dropwise at −20° C. in anhydrous DCM (2.0 mL). The mixture was stirred at this temperature for 1 h. Morpholine (0.18 mL, 0.30 mmol) was added dropwise at −20° C. The mixture was stirred at this temperature for 1 h. The solvent was removed and the residue obtained was purified by silica-gel column chromatography (0.5-10% MeOH in DCM) to afford the product as a white solid (210 mg, 35% yield). LC/MS (10%-99% CH$_3$CN (0.035% TFA)/H$_2$O (0.05% TFA)), m/z: M+1 obs=553.0; $t_R$=1.37 min. $^1$H NMR (400.0 MHz, CDCl$_3$) δ 7.96-7.91 (m, 2H), 7.77 (d, J=8.9 Hz, 2H), 7.50 (d, J=1.9 Hz, 1H), 7.41 (d, J=8.3 Hz, 1H), 7.22-7.16 (m, 1H), 6.55-6.53 (m, 1H), 4.59 (dd, J=2.2, 10.1 Hz, 1H), 4.17-4.06 (m, 1H), 3.94-3.75 (m, 4H), 3.71-3.66 (m, 1H), 3.02 (d, J=11.0 Hz, 1H), 2.86 (d, J=11.0 Hz, 1H), 2.73-2.64 (m, 2H), 2.38-2.31 (m, 1H) and 2.24-2.14 (m, 1H).

General Procedure 32

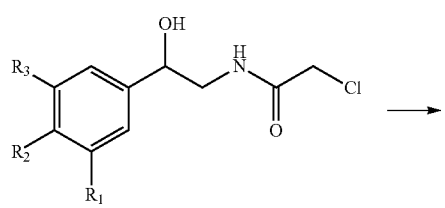

To a stirring solution of 2-chloroacetamide (1.0 mmol, 1 eq.) and ethyl alcohol (2.8 mL) was added a solution of potassium hydroxide (2.0 mmol, 2 eq.) in ethyl alcohol (2.3 mL). The mixture was heated via microwave at 100° C. for 20 minutes. The solution was evaporated at reduced pressure and partitioned with dichloromethane and water. The organic phase was dried over $MgSO_4$ and evaporated under reduced pressure. Trituration with hot ethyl acetate afforded the desired morpholin-3-one.

General Procedure 33

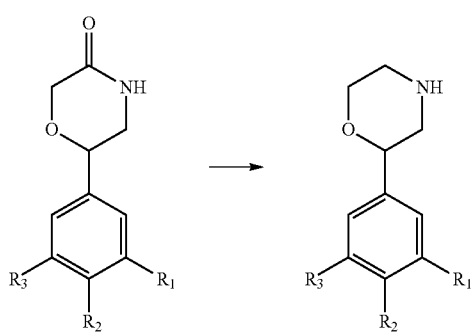

To a stirring solution of morpholin-3-one (1.0 mmol, 1 eq.) and ethyl alcohol (3.75 mL) under $N_2$ at 0° C. was added borane tetrahydrofuran complex (1.0 M in THF, 1.0 mmol, 1 eq.) dropwise over 5 minutes. The reaction mixture was stirred at 0° C. for an additional 5 minutes and then quenched by dropwise addition of water over 5 minutes. The pH was adjusted to pH 0 with conc. aqueous HCl and stirred for 5 minutes. The pH was adjusted to pH 13 with 2M aqueous NaOH solution and then partitioned with dichloromethane (10 mL). The organic phase was separated, and the aqueous phase was extracted with dichloromethane (3×10 mL). The combined organic extracts were dried over $MgSO_4$ and evaporated under reduced pressure. A solution of HCl in 1,4-dioxane (4M, 1 mmol, 1 eq.) was added, and the resulting mixture was evaporated under reduced pressure. Crystallization of the residue from $MeOH/Et_2O$ provided the desired product.

General Procedure 34

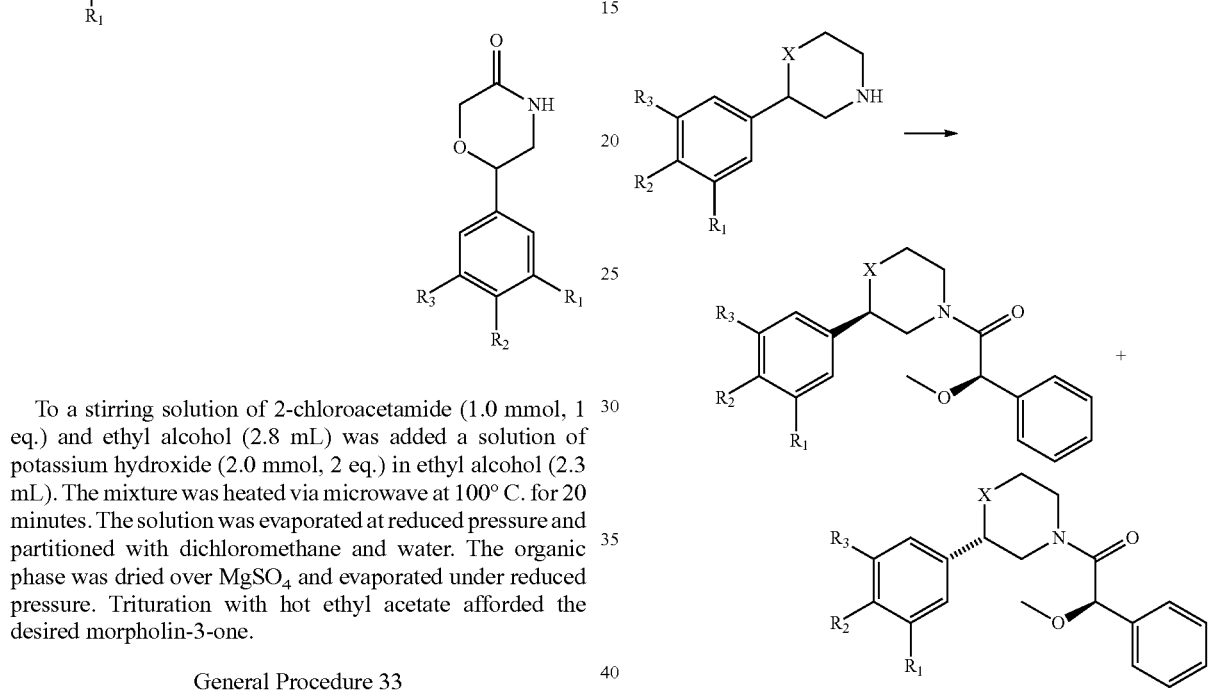

To a stirring solution of amine (1.0 mmol, 1 eq.), triethylamine (1.0 mmol, 1 eq.), (R)-(−)-α-OMe-phenylacetic acid (1.0 mmol, 1 eq.), and $CH_2Cl_2$ (1.0 mL), under $N_2$, at 5° C., was added HATU (1.0 mmol, 1 eq.). The solution was stirred at ambient temperature for 1 hour. Purification and separation by silica gel chromatography afforded the two discrete diastereomers which were arbitratily assigned.

(R)-1-((R)-2-(3,4-dichlorophenyl)morpholino)-2-methoxy-2-phenylethanone and (R)-1-((S)-2-(3,4-dichlorophenyl)morpholino)-2-methoxy-2-phenylethanone

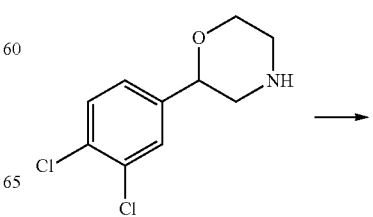

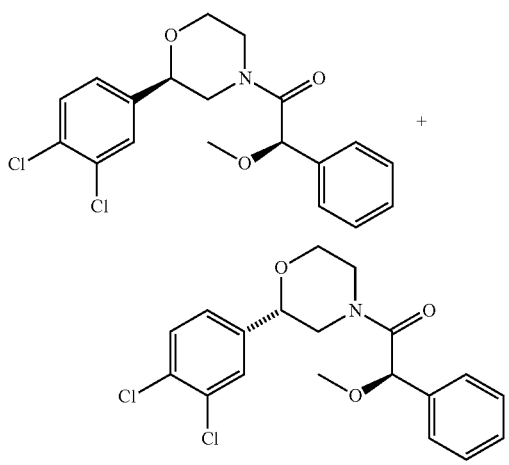

Synthesized according to General Procedure 34. To a stirring solution of 2-(3,4-dichlorophenyl)morpholine (1.0 g, 4.3 mmol), triethylamine (435 mg, 600 µL, 4.3 mmol), (R)-(−)-α-OMe-phenylacetic acid (715 mg, 4.3 mmol), and CH$_2$Cl$_2$ (5 mL), under N$_2$, at 5° C., was added HATU (1.6 g, 4.3 mmol). The solution was stirred at ambient temperature for 1 hour. The solution was purified via silica gel using 50% EtOAc in hexane to obtain a diastereomeric mixture (1.9 g). The mixture was purified via silica gel using 20% EtOAc in hexane to obtain the arbitrarily assigned (R, R)-product (620 mg, 1.6 mmol, 76% yield) and (R, S)-product (620 mg, 1.6 mmol, 76% yield) as clear oils. LC/MS (10%-99% CH$_3$CN (0.035% TFA)/H$_2$O (0.05% TFA)), (R, R) m/z: M+1 obs=380.3; t$_R$=1.84 min. (R, 5) m/z: M+1 obs=380.3; t$_R$=1.89 min.

(R)-1-((R)-2-(3,5-dichlorophenyl)morpholino)-2-methoxy-2-phenylethanone and (R)-1-((S)-2-(3,5-dichlorophenyl)morpholino)-2-methoxy-2-phenylethanone

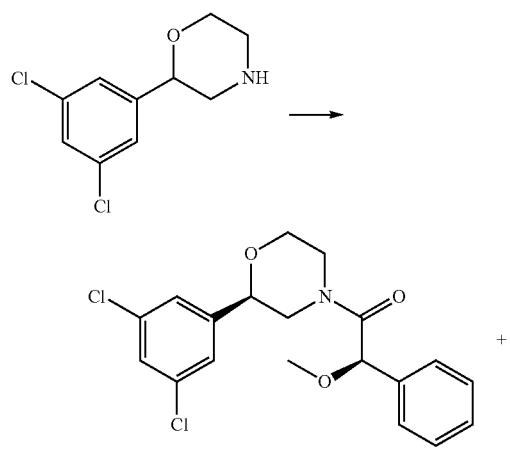

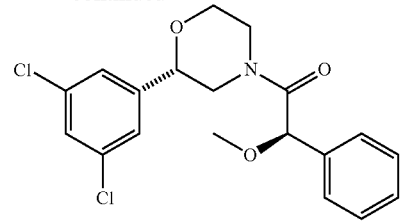

Synthesized according to General Procedure 34. To a stirring solution of 2-(3,5-dichlorophenyl)morpholine oxalate (50 mg, 0.16 mmol), triethylamine (22 µL, 0.16 mmol), (R)-(−)-α-OMe-phenylacetic acid (26 mg, 0.16 mmol), and CH$_2$Cl$_2$ (0.5 mL), under N$_2$, at 5° C., was added HATU (58 mg, 0.16 mmol). The solution was stirred at ambient temperature for 1 hour. The solution was purified via silica gel using 20-50% EtOAc in hexane to obtain the (R, R)-product (first to elute, 24 mg, 81% yield) and (R, 5)-product (second to elute, 25 mg, 85% yield) as clear oils. LC/MS (10%-99% CH$_3$CN (0.035% TFA)/H$_2$O (0.05% TFA)), (R, R) m/z: M+1 obs=380.3; t$_R$=2.05 min. (R, 5) m/z: M+1 obs=380.3; t$_R$=1.96 min.

General Procedure 35

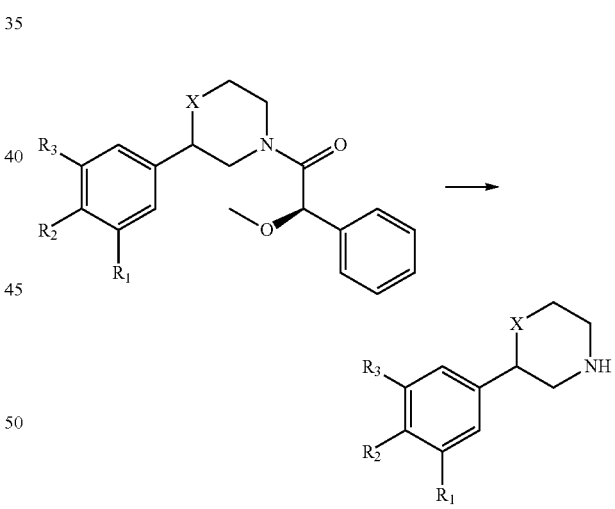

To a stirring solution of the amide (1.0 mmol, 1 eq.) and THF (5.5 mL), under N$_2$, at 0° C., was added a solution of Super-hydride in THF (1.0 M, 6.3 mmol, 6.3 eq.) dropwise over 10 minutes. The solution was stirred at 0° C. for 30 minutes. The solution was poured into 1 M aqueous HCl solution (15 mL). The solution was then bascified with NH$_4$OH and extracted with CH$_2$Cl$_2$ (3×30 mL). Purification via silica gel chromatography afforded the enantiomerically pure amine.

(R)-2-(3,4-dichlorophenyl)morpholine

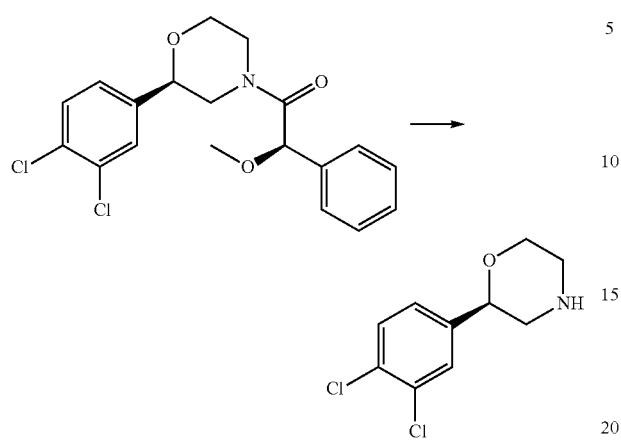

Synthesized according to General Procedure 35. To a stirring solution of (R)-1-((R)-2-(3,4-dichlorophenyl)-morpholino)-2-methoxy-2-phenylethanone (620 mg, 1.63 mmol) and THF (9 mL), under $N_2$, at 0° C., was added a solution of Super-hydride in THF (1.0 M, 10.3 mL, 10.3 mmol) dropwise over 10 minutes. The solution was stirred at 0° C. for 30 minutes. The solution was poured into 1M aqueous HCl solution (20 mL). The solution was then basified with $NH_4OH$ and extracted with $CH_2Cl_2$ (3×50 mL). Purified via silica gel chromatography using 10% MeOH in $CH_2Cl_2$ to obtain the desired morpholine, arbitrarily assigned (R) configuration, as a clear oil (290 mg, 1.3 mmol, 80% yield). $^1$H-NMR (400 MHz, CDCl$_3$) δ 7.50-7.49 (m, 2H), 7.19 (dd, J=1.6, 8.3 Hz, 1H), 4.47 (dd, J=2.4, 10.4 Hz, 1H), 4.09 (s, 1H), 4.08 (dd, J=1.9, 12.9 Hz, 1H), 3.82-3.75 (m, 1H), 3.09 (dd, J=2.5, 12.5 Hz, 1H), 2.97 (dd, J=3.1, 10.2 Hz, 2H), 2.72-2.69 (m, 1H). LC/MS (10%-99% CH$_3$CN (0.035% TFA)/H$_2$O (0.05% TFA)), m/z: M+1 obs=232.3; $t_R$=0.67 min.

(R)-2-(3,4-Dichlorophenyl)oxirane

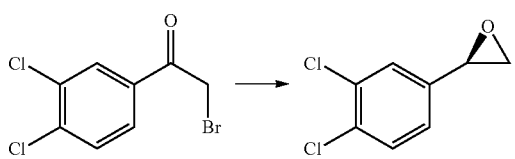 [SMILES: O=C(CBr)c1ccc(Cl)c(Cl)c1 ; Clc1ccc([C@@H]2CO2)cc1Cl]

In a 5 L 3 neck flask in a water bath equipped with a mechanical stirrer, thermocouple and 1 L addition funnel under nitrogen at RT was charged (3aR)-1-methyl-3,3-diphenyl-3a,4,5,6-tetrahydropyrrolo[1,2-c][1,3,2]oxazaborole (49.8 mL of 1 M, 49.8 mmol) followed by borane-tetrahydrofuran complex (897 g, 999 mL of 1 M, 999 mmol) via a cannula with nitrogen pressure. After stirring the mixture for 15 minutes a solution of 2-bromo-3',4',dichloroacetophenone (267 g, 997 mmol) in THF (1.0 L) was added dropwise at a rate of 2-4 mL/min over 6 hours maintaining the pot temperature at <25° C. The reaction mixture was stirred at RT for 1 hour following the addition. The reaction was quenched with methanol (202 mL, 4.98 mol) dropwise over 10 minutes. To the mixture was carefully added NaOH (997 mL of 2 M, 1.99 mol) (slight exotherm to 35° C.) and the mixture stirred at rt for 1 h. The mixture was transferred to a separatory funnel and the phases separated. The organic phase was concentrated in vacuo then diluted with 600 mL of MTBE. The aqueous phase was extracted with 600 mL of MTBE and the organic phase combined with the first organic phase. The combined organic phases were washed with 1 L of brine, dried over MgSO$_4$, filtered over celite and concentrated in vacuo affording (2R)-2-(3,4-dichlorophenyl)oxirane (184 g, 98%) of as a thick oil. $^1$H-NMR (400 MHz, CDCl$_3$) δ 7.54-7.38 (m, 3H), 7.14 (dd, J=2.2, 8.0 Hz, 1H), 3.84 (dd, J=2.8, 4.0 Hz, 1H), 3.17 (dd, J=4.0, 5.2 Hz, 1H), 2.77-2.71 (m, 1H). LC/MS (10%-99% CH$_3$CN (0.035% TFA)/H$_2$O (0.05% TFA)), no observed ion; $t_R$=1.57 min.

(R)-1-(3,4-Dichlorophenyl)-2-(2-hydroxyethylamino)ethanol

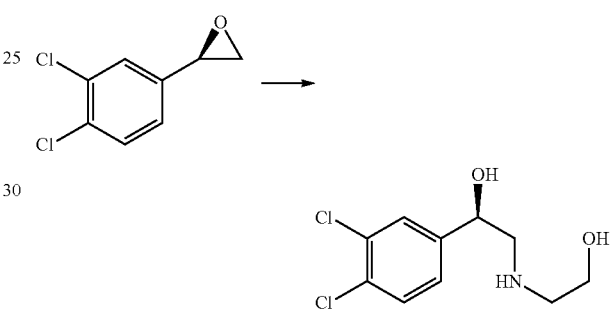

In a 3 neck flask equipped with a mechanical stirrer, thermocouple and addition funnel in an ambient temperature water bath was added ethanolamine (330 mL, 5.47 mol). (R)-2-(3,4-dichlorophenyl)oxirane (184 g, 976 mmol) in isopropanol (75 mL) was added dropwise over 1 h. Reaction temperature stayed <30° C. during addition. The reaction mixture was stirred at ambient temperature for 14 h, diluted with 2000 mL of ice water and extracted three times with 1000 mL of ethyl acetate. The combined organic phases were dried over MgSO$_4$, filtered over Celite and concentrated in vacuo affording (1R)-1-(3,4-dichlorophenyl)-2-(2-hydroxyethylamino)-ethanol (244 g, 100%) as a white semi-solid. $^1$H-NMR (400 MHz, CDCl$_3$) δ 7.58-7.54 (m, 2H), 7.35-7.32 (m, 1H), 5.51 (s, 1H), 4.64 (dd, J=5.0, 7.2 Hz, 1H), 4.49 (s, 1H), 3.43 (dd, J=5.0, 10.4 Hz, 2H), 2.69-2.50 (m, 4H). LC/MS (10%-99% CH$_3$CN (0.035% TFA)/H$_2$O (0.05% TFA)), m/z: M+1 obs=250.3; $t_R$=0.84 min.

(R)-tert-Butyl 2-(3,4-dichlorophenyl)-2-hydroxyethyl(2-hydroxyethyl)-carbamate

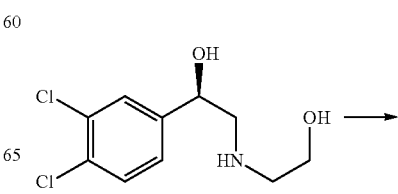

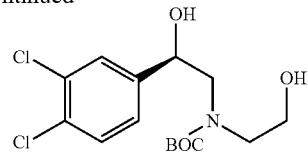

In a 3 neck flask equipped with a mechanical stirrer, thermocouple and addition funnel was added (R)-1-(3,4-dichlorophenyl)-2-(2-hydroxyethylamino)ethanol (370 g, 1.48 mol) followed by DCM (1.48 L). A solution of (Boc)$_2$O (307 g, 323 mL, 1.41 mol) in 500 mL of DCM was added dropwise using an addition funnel. The reaction mixture was stirred at RT for 2 h. The mixture was washed with 1000 mL of water, twice with 1000 mL of brine, dried over MgSO$_4$, filtered over Celite and concentrated in vacuo to afford (R)-tert-Butyl 2-(3,4-dichlorophenyl)-2-hydroxyethyl(2-hydroxyethyl)-carbamate (518 g, 100%) as a thick, foamy oil. $^1$H-NMR (400 MHz, DMSO) δ 7.59 (t, J=8.0 Hz, 1H), 7.51 (s, 1H), 7.27 (t, J=8 Hz, 1H), 5.74-5.70 (m, 1H), 4.76-4.70 (m, 2H), 3.49-3.24 (m, 4H), 1.26 (s, 9H). LC/MS (10%-99% CH$_3$CN (0.035% TFA)/H$_2$O (0.05% TFA)), m/z: M+1 obs=350.3; t$_R$=1.64 min.

(R)-2-(3,4-Dichlorophenyl)morpholine

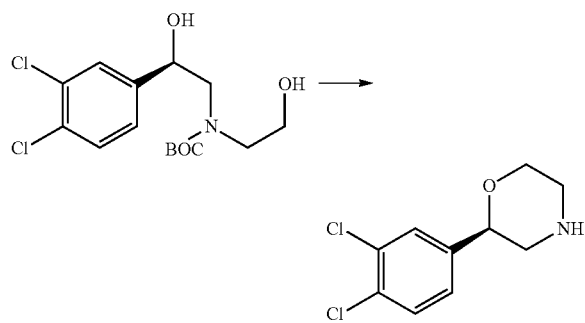

In a 3 neck flask equipped with a mechanical stirrer, thermocouple and addition funnel using a water bath was added (R)-tert-butyl 2-(3,4-dichlorophenyl)-2-hydroxyethyl(2-hydroxyethyl)-carbamate (588 g, 1.679 mol) followed by MTBE (2.5 L). To the mixture was added triphenylphosphine (528 g, 467 mL, 2.02 mol) followed by isopropyl N-isopropoxycarbonyliminocarbamate (407 g, 390 mL, 2.02 mol) dropwise. During the addition, the reaction temperature gradually increased to reflux. The reaction mixture was allowed to stir at ambient temperature for 1 h. A precipitate occurred and the mixture was chilled with an ice bath to 15° C. The resulting precipitate was filtered, and the filter cake was washed with 2 L of MTBE. The filtrate was concentrated to approximately 2 L in vacuo and returned to the reaction vessel. HCl (1.26 L of 4 M in dioxane, 5.04 mol) was added and the mixture was stirred at 55° C. for 3 h. Effervescence occurred. The mixture was allowed to stir at RT for 10 h and quenched with 1 L of 5M NaOH. The phases were separated and the organic phase was washed with 1 L of brine, and concentrated in vacuo affording an oil which was 98% ee (chiral HPLC). In a 3 neck flask equipped with a mechanical stirrer, thermocouple and heating mantle was added crude yellow oil using glacial acetic acid (2.5 L) The solution was heated and to the mixture was added (2R,3R)-2,3-bis[(4-methylbenzoyl)oxy]butanedioic acid (649 g, 1.68 mol) affording a white slurry. The mixture was heated to reflux affording a clear amber solution. The mixture was vacuum transferred to a clean 5 L flask using a transfer tube and a course sparge tube as a filter. The mixture was seeded and allowed to cool to −45° C. at ambient temperature and then cooled with an ice-bath to 12° C. The resulting mixture was filtered over a medium fritted funnel and washed with 500 mL of glacial acetic acid. The filter cake was slurried with MTBE (500 mL twice), filtered and dried affording (R)-2-(3,4-dichlorophenyl)morpholine (2R,3R)-2,3-bis[(4-methylbenzoyl)oxy]butanedioic acid salt (233 g) as a white solid. The combined mother liquors were concentrated to 2 L in vacuo. The solution was allowed to sit for 12 h, filtered and the filter cake washed with 1 L of MTBE. This afforded an additional 186 g of product for a total of 419 g (40%, >99% ee) of product. To prepare the free base, the salt (178 g, 288 mmol) was added to a 2 L Erlenmeyer flask and diluted with 1 L of MTBE. 2M NaOH (400 mL) was added and the mixture was stirred until clear. The organic phase was separated and the aqueous phase was extracted with 500 mL of MTBE. The combined organic phases were dried over MgSO$_4$ and concentrated in vacuo to afford the free base (R)-2-(3,4-dichlorophenyl)-morpholine (66 g, 100%) as a colorless oil. $^1$H-NMR (400 MHz, CDCl$_3$) δ 7.50-7.49 (m, 2H), 7.19 (dd, J=1.6, 8.3 Hz, 1H), 4.47 (dd, J=2.4, 10.4 Hz, 1H), 4.09 (s, 1H), 4.08 (dd, J=1.9, 12.9 Hz, 1H), 3.82-3.75 (m, 1H), 3.09 (dd, J=2.5, 12.5 Hz, 1H), 2.97 (dd, J=3.1, 10.2 Hz, 2H), 2.72-2.69 (m, 1H). LC/MS (10%-99% CH$_3$CN (0.035% TFA)/H$_2$O (0.05% TFA)), m/z: M+1 obs=232.3; t$_R$=0.67 min. Chiral HPLC (Astec Chirobiotic V2 column (25 cm×4.6 mm, 5 um), 100% methanol (0.1% NH$_4$TFA, 1.5 mL/min) t$_R$ (R)=10.81 min; t$_R$ (S)=13.65 min.

(S)-2-(3,4-dichlorophenyl)morpholine

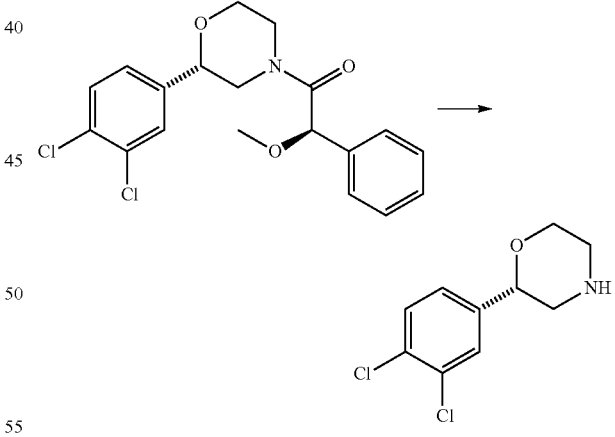

Synthesized according to General Procedure 35. To a stirring solution of (R)-1-((S)-2-(3,4-dichlorophenyl)-morpholino)-2-methoxy-2-phenylethanone (620 mg, 1.63 mmol) and THF (9 mL), under N$_2$, at 0° C., was added a solution of Super-hydride in THF (1.0 M, 10.3 mL, 10.3 mmol) dropwise over 10 minutes. The solution was stirred at 0° C. for 30 minutes. The solution was poured into 1M aqueous HCl solution (20 mL). The solution was then basified with NH$_4$OH and extracted with CH$_2$Cl$_2$ (3×50 mL). Purified via silica gel chromatography using 10% MeOH in CH$_2$Cl$_2$ to obtain the desired morpholine, arbitrarily assigned the (5) configuration, as a clear oil (250 mg, 1.1 mmol, 67% yield). ¹H-NMR (400 MHz, CDCl₃) δ 7.50-7.49 (m, 2H), 7.19 (dd, J=1.6, 8.3 Hz, 1H), 4.47 (dd, J=2.4, 10.4 Hz, 1H), 4.09 (s, 1H), 4.08 (dd, J=1.9, 12.9 Hz, 1H), 3.82-3.75 (m, 1H), 3.09 (dd, J=2.5, 12.5 Hz, 1H), 2.97 (dd, J=3.1, 10.2 Hz, 2H), 2.72-2.69 (m, 1H). LC/MS (10%-99% CH₃CN (0.035% TFA)/H₂O (0.05% TFA)), m/z: M+1 obs=232.3; $t_R$=0.65 min.

(S)-2-(3,5-dichlorophenyl)morpholine

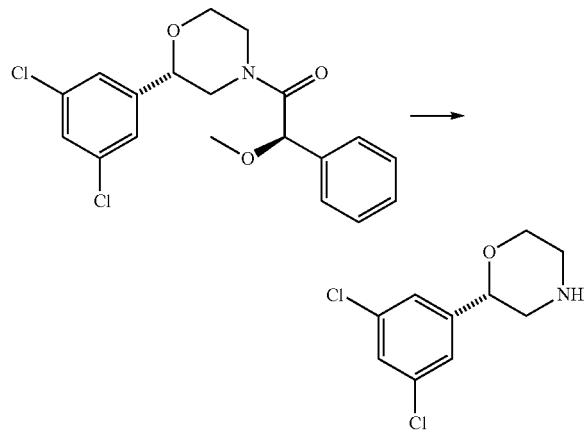

Synthesized according to General Procedure 35. To a stirring solution of (R)-1-((S)-2-(3,5-dichlorophenyl)-morpholino)-2-methoxy-2-phenylethanone (24 mg, 0.06 mmol) and THF (2.2 mL), under N₂, at 0° C., was added a solution of Super-hydride in THF (1.0 M, 0.4 mL, 0.4 mmol) dropwise over 10 minutes. The solution was stirred at 0° C. for 30 minutes. The solution was poured into 2M aqueous HCl solution (3 mL) and washed with diethyl ether (3×3 mL). The aqueous phase was concentrated and purified by preparative HPLC. The ee was determined to be >98%. LC/MS (10%-99% CH₃CN (0.035% TFA)/H₂O (0.05% TFA)), m/z: M+1 obs=232.1; $t_R$=1.04 min. SFC (Chiralpak IA, (0.46×25 cm), 35% methanol (0.1% DEA)/CO₂, 3 mL/min): $t_R$ (S)=2.0 min, $t_R$ (R)=3.39 min.

General Procedure 36

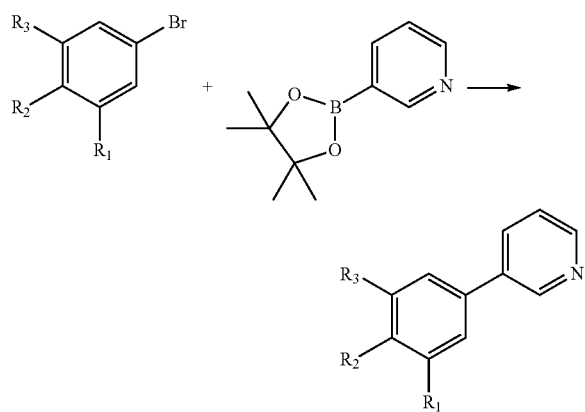

A mixture of aryl bromide (1.0 mmol, 1 eq.), 3-pyridineboronic acid pinacol ester (1.3 mmol, 1.3 eq.), aqueous 2M Na₂CO₃ (2.1 mmol, 2.1 eq.) and Pd(PPh₃)₄ (4 mol %) in anhydrous toluene (10 mL) was stirred overnight at 80° C. under nitrogen. The reaction was cooled down to room temperature, diluted with water (5 ml) and ethyl acetate (10 ml). The organic phase was separated, dried (Na₂SO₄), filtered and concentrated under reduced pressure. Purification by silica-gel column chromatography afforded the product.

3-(3,5-dichlorophenyl)pyridine

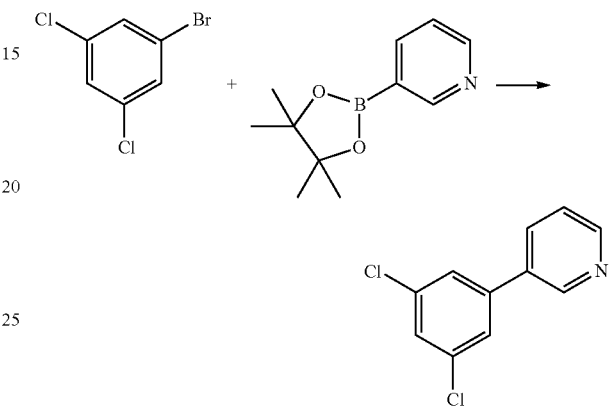

Synthesized according to General Procedure 36. A mixture of 1-bromo-3,5-dichloro-benzene (424 mg, 1.88 mmol), 3-pyridineboronic acid pinacol ester (500 mg, 2.44 mmol), aqueous 2M Na₂CO₃ (1.96 mL, 3.93 mmol) and Pd(PPh₃)₄ (89 mg, 4 mol %) in anhydrous toluene (18 mL) was stirred overnight at 80° C. under nitrogen. The reaction was cooled down to room temperature, diluted with water (5 ml) and ethyl acetate (10 ml). The organic phase was separated, dried (Na₂SO₄), filtered and concentrated under reduced pressure to give a pale yellow oil, which was purified by silica-gel column chromatography to give 3-(3,5-dichlorophenyl)pyridine (481 mg, 74%) as a white solid. ¹H-NMR (400 MHz, CDCl₃) δ 8.81 (d, J=2.1 Hz, 1H), 8.65 (dd, J=1.4, 4.8 Hz, 1H), 7.85-7.82 (m, 1H), 7.46 (d, J=1.8 Hz, 2H), 7.41-7.38 (m, 2H). LC/MS (10%-99% CH₃CN (0.035% TFA)/H₂O (0.05% TFA)), m/z: M+1 obs=224.3; $t_R$=1.21 min.

General Procedure 37

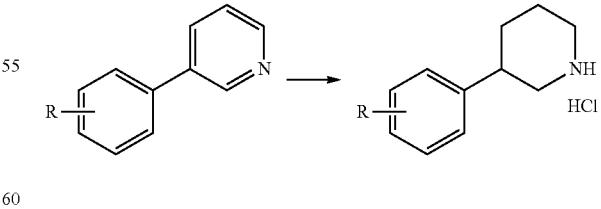

A solution of the pyridine (1.0 mmol, 1 eq.) in MeOH (2 mL) and 2 M HCl (0.3 mL) was stirred under 60 psi of H₂ in the presence of PtO₂ (0.6 mmol, 0.6 eq.) for 3 h using a Parr shaker. The reaction mixture was filtrated through Celite and the filter cake was washed thoroughly with MeOH. The filtrate was concentrated under reduced pressure to afford the desired product.

3-(3,5-dichlorophenyl)piperidine hydrochloride

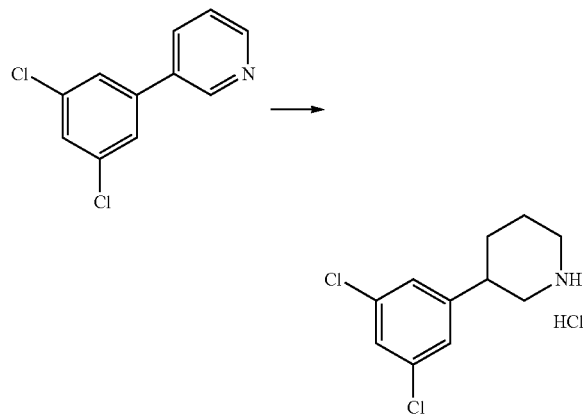

Synthesized according to General Procedure 37. A solution of 3-(3,5-dichlorophenyl)-pyridine (481 mg, 2.15 mmol) in MeOH (4.6 mL) and 2 M HCl (0.6 mL) was stirred under 60 psi of $H_2$ in the presence of $PtO_2$ (283 mg, 1.246 mmol) for 3 h using a Parr shaker. The reaction mixture was filtrated through Celite, and the filter cake was washed thoroughly with MeOH. The filtrate was concentrated under reduced pressure to afford 3-(3,5-dichlorophenyl)piperidine hydrochloride (564 mg, 92%). LC/MS (10%-99% $CH_3CN$ (0.035% TFA)/$H_2O$ (0.05% TFA)), m/z: M+1 obs=230.3; $t_R$=1.14 min.

(R)-1-((R)-3-(3,5-dichlorophenyl)piperidin-1-yl)-2-methoxy-2-phenylethanone and (R)-1-((S)-3-(3,5-dichlorophenyl)piperidin-1-yl)-2-methoxy-2-phenylethanone

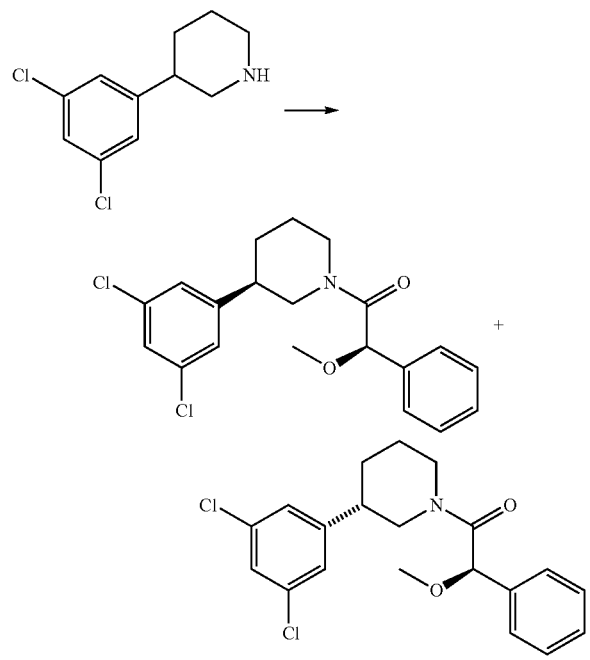

Synthesized according to General procedure 34. To a solution of 3-(3,5-dichlorophenyl)-piperidine hydrochloride (527 mg, 1.98 mmol), (R)-(−)-α-methoxy-phenylacetic acid (329 mg, 1.98 mmol), and triethylamine (400 mg, 0.55 mL, 3.95 mmol) in anhydrous DCM (9 mL) was added HATU (752 mg, 1.98 mmol) in one portion at room temperature. After 1 h, the solvent was removed and the residue was purified by silica-gel column chromatography (15% ethyl acetate in hexanes). The first fraction to elute was arbitrarily assigned as (R)-1-(R)-3-(3,5-dichlorophenyl)piperidin-1-yl)-2-methoxy-2-phenylethanone (222 mg, 30%), and the second fraction to elute was arbitrarily assigned as (R)-1-((S)-3-(3,5-dichlorophenyl)piperidin-1-yl)-2-methoxy-2-phenylethanone (220 mg, 30%). LC/MS (10%-99% $CH_3CN$ (0.035% TFA)/$H_2O$ (0.05% TFA)), m/z: M+1 obs=278.3; $t_R$ (R,R)=2.06 min, $t_R$ (R,S)=2.00 min.

(S)-3-(3,5-dichlorophenyl)piperidine

Synthesized according to General procedure 35. To a solution of (R)-1-((S)-3-(3,5-dichlorophenyl)piperidin-1-yl)-2-methoxy-2-phenylethanone (98 mg, 0.26 mmol) in anhydrous THF (9 mL) under nitrogen at 0° C. was added Super-hydride (1.0 M in THF, 1.63 mL, 1.63 mmol) dropwise. The solution was stirred at 0° C. for 2 h, and then poured into 2M aqueous HCl (3 mL). The aqueous phase was washed twice with $Et_2O$ (2×3 ml), then basified by addition of $NH_4OH$ at 0° C. The product was extracted with DCM (3×3 ml), the organic phases were combined, dried over sodium sulfate, filtered, then concentrated under reduced pressure, providing 3-(3,5-dichlorophenyl)piperidine (59 mg, 67%) which was arbitrarily assigned the (S)-configuration, as a pale yellow oil. This material was used without further purification. $^1$H-NMR (400 MHz, $CDCl_3$) δ 7.22 (s, 1H), 7.20 (t, J=1.8 Hz, 1H), 7.09 (d, J=1.8 Hz, 2H), 3.17-3.05 (m, 2H), 2.65-2.57 (m, 3H), 2.01-1.96 (m, 1H), 1.81-1.77 (m, 1H), 1.60-1.53 (m, 2H), 1.60-1.53 (m, 2H). LC/MS (10%-99% $CH_3CN$ (0.035% TFA)/$H_2O$ (0.05% TFA)), m/z: M+1 obs=230.3; $t_R$=1.10 min.

General Procedure 38

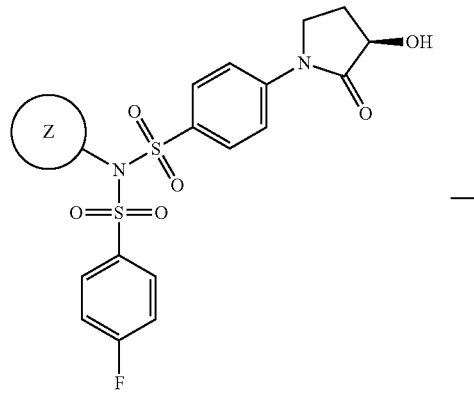

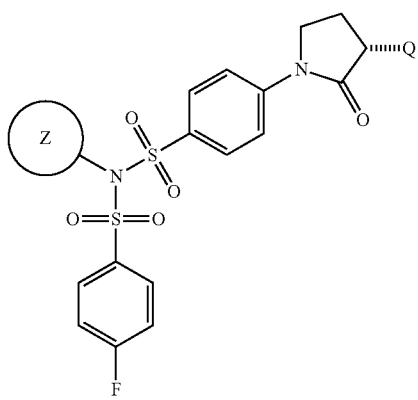

To a solution of the alcohol (1.0 mmol, 1 eq.) in dichloromethane (3 mL) at −40° C. under nitrogen was added N,N-diisopropylethylamine (3.0 mmol, 3 eq.), followed by trifluoromethanesulfonic anhydride (2.0 mmol, 2 eq.). The reaction was stirred for 1 h, keeping the temperature between −40° C. and −50° C. A solution of the amine (1.5 mmol, 1.5 eq.) in dichloromethane (1.5 mL) was added. The reaction was allowed to slowly warm to room temperature and was stirred overnight. Purification of the crude material was carried out using silica gel chromatography to afford the desired product.

General Procedure 39

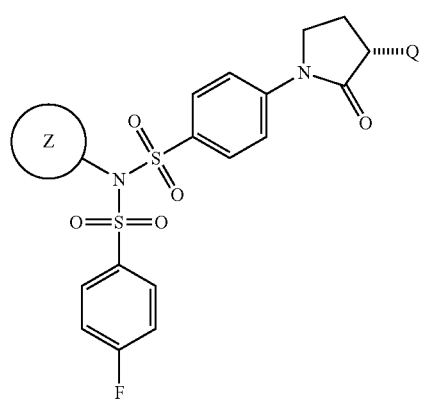

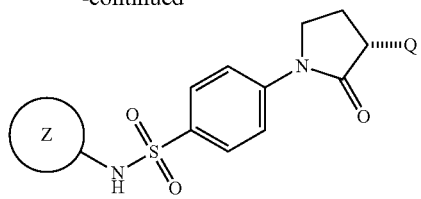

To a solution of the bissulfonamide (1.0 mmol, 1 eq.) in anhydrous acetonitrile (10 mL) was added morpholine (2.0 mmol, 2 eq.) dropwise at room temperature. The reaction mixture was stirred for 15 min, then the solvent was removed and the residue obtained was purified by silica-gel column chromatography to afford the product.

4-((S)-3-((S)-3-(3,5-dichlorophenyl)piperidin-1-yl)-2-oxopyrrolidin-1-yl)-N-(4-fluorophenylsulfonyl)-N-(thiazol-2-yl)benzenesulfonamide

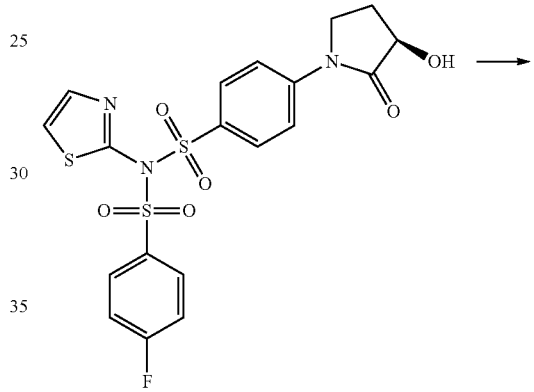

Synthesized according to General procedure 38. To a solution of (R)-4-fluoro-N-(4-(3-hydroxy-2-oxopyrrolidin-1-yl)phenylsulfonyl)-N-(thiazol-2-yl)benzene-sulfonamide (144 mg, 0.29 mmol) in anhydrous DCM (0.95 mL) at −45° C. under nitrogen, were successively added DIEA (113 mg, 0.15 mL, 0.87 mmol) followed by triflic anhydride (164 mg, 0.098 mL, 0.58 mmol) dropwise. The mixture was stirred at this temperature for 1 h, then 3-(3,5-dichlorophenyl)piperidine (88 mg, 0.44 mmol) was added dropwise in anhydrous DCM (0.5 mL). The reaction mixture was stirred overnight, the temperature allowed to raise gradually to room temperature. The solvent was removed under reduced pressure and the residue obtained was purified by silica-gel column chromatography (20-100% ethyl acetate in hexanes) providing the product (107 mg, 52%). Configuration of the piperidine arbitrarily assigned as (S). LC/MS (10%-99% CH$_3$CN (0.035% TFA)/H$_2$O (0.05% TFA)), m/z: M+1 obs=709.5; t$_R$=1.66 min.

4-((S)-3-((R)-3-(3,5-dichlorophenyl)piperidin-1-yl)-2-oxopyrrolidin-1-yl)-N-(4-fluorophenylsulfonyl)-N-(thiazol-2-yl)benzenesulfonamide

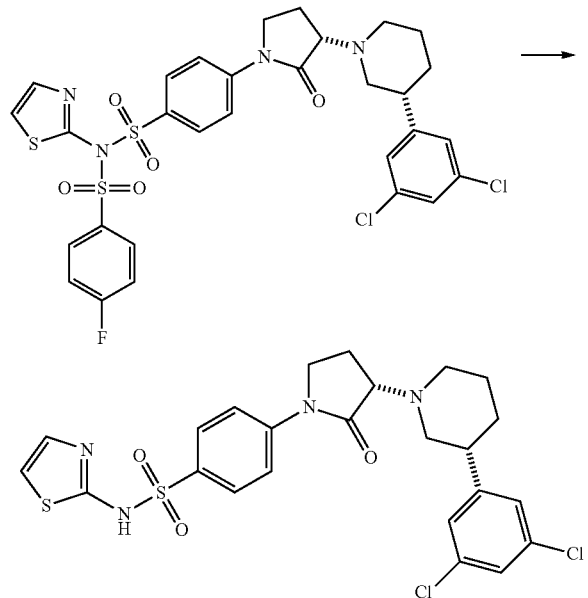

Synthesized according to General procedure 39. To a solution of 4-((S)-3-((S)-3-(3,5-dichlorophenyl)piperidin-1-yl)-2-oxopyrrolidin-1-yl)-N-(4-fluorophenylsulfonyl)-N-(thiazol-2-yl)benzenesulfonamide (107 mg, 0.15 mmol) in dry acetonitrile (1.45 mL) was added morpholine (26 mg, 26 µL, 0.30 mmol) dropwise at room temperature. The reaction mixture was stirred for 15 min, then the solvent was removed and the residue obtained was purified by silica-gel column chromatography (0.5-10% MeOH in DCM) to afford the product as a white solid (60 mg, 72%). LC/MS (10%-99% CH$_3$CN (0.035% TFA)/H$_2$O (0.05% TFA)), m/z: M+1 obs=551.3; t$_R$=1.31 min. $^1$H NMR (400.0 MHz, DMSO) δ 7.84-7.77 (m, 4H), 7.43 (t, J=1.9 Hz, 1H), 7.36 (d, J=1.9 Hz, 2H), 7.24 (d, J=4.6 Hz, 1H), 6.81 (d, J=4.6 Hz, 1H), 3.80-3.70 (m, 3H), 2.97 (d, J=10.6 Hz, 1H), 2.80-2.73 (m, 3H), 2.33 (dd, J=9.0, 11.0 Hz, 1H), 2.22-2.17 (m, 1H), 2.09 (dd, J=9.2, 12.5 Hz, 1H), 1.80 (d, J=11.2 Hz, 1H), 1.73-1.70 (m, 1H) and 1.58-1.44 (m, 2H).

Table 3 below recites the analytical data for the compounds of Table 2 above.

TABLE 3

| Cmpd No. | LC/MS M + 1 | LC/RT min | $^1$HNMR (400.0 MHz, CDCl$_3$) |
|---|---|---|---|
| 1 | 553.3 | 1.42 | δ 12.71 (s, 1H), 7.84-7.77 (m, 4H), 7.54-7.50 (m, 1H), 7.44 (d, J = 1.8 Hz, 2H), 7.24 (d, J = 4.6 Hz, 1H), 6.82 (d, J = 4.6 Hz, 1H), 4.57 (dd, J = 1.7, 9.8 Hz, 1H), 3.97-3.91 (m, 1H), 3.79-3.62 (m, 4H), 3.21-3.17 (m, 1H), 2.95-2.86 (m, 2H), 2.69-2.66 (m, 1H), 2.22-2.12 (m, 2H) |
| 2 | 553 | 1.37 | δ 7.96-7.91 (m, 2H), 7.77 (d, J = 8.9 Hz, 2H), 7.50 (d, J = 1.9 Hz, 1H), 7.41 (d, J = 8.3 Hz, 1H), 7.22-7.16 (m, 1H), 6.55-6.53 (m, 1H), 4.59 (dd, J = 2.2, 10.1 Hz, 1H), 4.17-4.06 (m, 1H), 3.94-3.75 (m, 4H), 3.71-3.66 (m, 1H), 3.02 (d, J = 11.0 Hz, 1H), 2.86 (d, J = 11.0 Hz, 1H), 2.73-2.64 (m, 2H), 2.38-2.31 (m, 1H) and 2.24-2.14 (m, 1H) |
| 3 | 551 | 1.32 | δ 7.84-7.77 (m, 4H), 7.43 (t, J = 1.9 Hz, 1H), 7.36 (d, J = 1.9 Hz, 2H), 7.24 (d, J = 4.6 Hz, 1H), 6.81 (d, J = 4.6 Hz, 1H), 3.80-3.70 (m, 3H), 2.97 (d, J = 10.6 Hz, 1H), 2.80-2.73 (m, 3H), 2.33 (dd, J = 9.0, 11.0 Hz, 1H), 1.80 (d, J = 11.2 Hz, 1H), 1.73-1.70 (m, 1H) and 1.58-1.44 (m, 2H) |
| 4 | 553 | 1.37 | |
| 5 | 553 | 1.44 | δ 7.85-7.78 (m, 4H), 7.54 (t, J = 1.9 Hz, 1H), 7.42 (d, J = 1.8 Hz, 2H), 7.25 (d, J = 4.6 Hz, 1H), 6.82 (d, J = 4.6 Hz, 1H), 4.53 (dd, J = 1.9, 9.9 Hz, 1H), 3.97 (d, J = 9.9 Hz, 1H), 3.80-3.65 (m, 4H), 3.01-2.89 (m, 2H), 2.70-2.65 (m, 1H), 2.51-2.45 (m, 1H), 2.27-2.22 (m, 1H), 2.12-2.07 (m, 1H) |
| 6 | 551 | 1.32 | |

Assays for Detecting and Measuring NaV Inhibition Properties of Compound

Optical Methods for Assaying NaV Inhibition Properties of Compounds:

Compounds of the invention are useful as antagonists of voltage-gated sodium ion channels. Antagonist properties of test compounds were assessed as follows. Cells expressing the NaV of interest were placed into microtiter plates. After an incubation period, the cells were stained with fluorescent dyes sensitive to the transmembrane potential. The test compounds were added to the microtiter plate. The cells were stimulated with either a chemical or electrical means to evoke a NaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" Biophys J 69(4): 1272-80, and Gonzalez, J. E. and R. Y. Tsien (1997) "Improved indicators of cell membrane potential that use fluorescence resonance energy transfer" Chem Biol 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" Drug Discov Today 4(9): 431-439).

VIPR® Optical Membrane Potential Assay Method with Chemical Stimulation

Cell Handling and Dye Loading 24 hours before the assay on VIPR, CHO cells endogenously expressing a NaV1.2 type voltage-gated NaV are seeded in 96-well poly-lysine coated plates at 60,000 cells per well. Other subtypes are performed in an analogous mode in a cell line expressing the NaV of interest.

1) On the day of the assay, medium is aspirated and cells are washed twice with 225 µL of Bath Solution #2 (BS#2).
2) A 15 uM CC2-DMPE solution is prepared by mixing 5 mM coumarin stock solution with 10% Pluronic 127 1:1 and then dissolving the mix in the appropriate volume of BS#2.

3) After bath solution is removed from the 96-well plates, the cells are loaded with 80 μL of the CC2-DMPE solution. Plates are incubated in the dark for 30 minutes at room temperature.
4) While the cells are being stained with coumarin, a 15 μL oxonol solution in BS#2 is prepared. In addition to DiSBAC$_2$(3), this solution should contain 0.75 mM ABSC1 and 300 μL veratridine (prepared from 10 mM EtOH stock, Sigma #V-5754).
5) After 30 minutes, CC2-DMPE is removed and the cells are washed twice with 225 μL of BS#2. As before, the residual volume should be 40 μL.
6) Upon removing the bath, the cells are loaded with 80 μL of the DiSBAC$_2$(3) solution, after which test compound, dissolved in DMSO, is added to achieve the desired test concentration to each well from the drug addition plate and mixed thoroughly. The volume in the well should be roughly 121 μL. The cells are then incubated for 20-30 minutes.
7) Once the incubation is complete, the cells are ready to be assayed on VIPR® with a sodium add back protocol. 120 μL of Bath solution #1 is added to stimulate the NaV dependent depolarization. 200 μL tetracaine was used as an antagonist positive control for block of the NaV channel.

Analysis of VIPR® Data:

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\ nm} - background_{460\ nm})}{(intensity_{580\ nm} - background_{580\ nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated. For the Na$^+$ addback analysis time windows, baseline is 2-7 sec and final response is sampled at 15-24 sec.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R - P}{N - P} * 100.$$

where R is the ratio response of the test compound
Solutions [mM]
Bath Solution #1: NaCl 160, KCl 4.5, CaCl$_2$ 2, MgCl$_2$ 1, HEPES 10, pH 7.4 with NaOH
Bath Solution #2 TMA-Cl 160, CaCl$_2$ 0.1, MgCl$_2$ 1, HEPES 10, pH 7.4 with KOH (final K concentration ~5 mM)
CC2-DMPE: prepared as a 5 mM stock solution in DMSO and stored at -20° C.
DiSBAC$_2$(3): prepared as a 12 mM stock in DMSO and stored at -20° C.
ABSC1: prepared as a 200 mM stock in distilled H$_2$O and stored at room temperature Cell Culture CHO cells are grown in DMEM (Dulbecco's Modified Eagle Medium; GibcoBRL #10569-010) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% CO$_2$, to 100% confluence. They are usually split by trypsinization 1:10 or 1:20, depending on scheduling needs, and grown for 2-3 days before the next split.

VIPR® Optical Membrane Potential Assay Method with Electrical Stimulation

The following is an example of how NaV1.3 inhibition activity is measured using the optical membrane potential method#2. Other subtypes are performed in an analogous mode in a cell line expressing the NaV of interest.

HEK293 cells stably expressing NaV1.3 are plated into 96-well microtiter plates. After an appropriate incubation period, the cells are stained with the voltage sensitive dyes CC2-DMPE/DiSBAC2(3) as follows.

Reagents 100 mg/mL Pluronic F-127 (Sigma #P2443), in dry DMSO
10 mM DiSBAC$_2$(3) (Aurora #00-100-010) in dry DMSO
10 mM CC2-DMPE (Aurora #00-100-008) in dry DMSO
200 mM ABSC1 in H$_2$O
Hank's Balanced Salt Solution (Hyclone #SH30268.02) supplemented with 10 mM HEPES (Gibco #15630-080)

Loading Protocol

2×CC2-DMPE=20 μM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 μL of 2×CC2-DMPE is to wells containing washed cells, resulting in a 10 μM final staining concentration. The cells are stained for 30 minutes in the dark at RT.

2×DISBAC$_2$(3) with ABSC1=6 μM DISBAC$_2$(3) and 1 mM ABSC1: The required amount of 10 mM DISBAC$_2$(3) is added to a 50 ml conical tube and mixed with 1 μL 10% pluronic for each mL of solution to be made and vortexed together. Then HBSS/HEPES is added to make up 2× solution. Finally, the ABSC1 is added.

The 2×DiSBAC$_2$(3) solution can be used to solvate compound plates. Note that compound plates are made at 2× drug concentration. Wash stained plate again, leaving residual volume of 50 μL. Add 50 uL/well of the 2×DiSBAC$_2$(3) w/ABSC1. Stain for 30 minutes in the dark at RT.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Reagents

Assay Buffer #1
140 mM NaCl, 4.5 mM KCl, 2 mM CaCl$_2$, 1 mM MgCl$_2$, 10 mM HEPES, 10 mM glucose, pH 7.40, 330 mOsm Pluronic stock (1000×): 100 mg/mL pluronic 127 in dry DMSO Oxonol stock (3333×): 10 mM DiSBAC$_2$(3) in dry DMSO Coumarin stock (1000×): 10 mM CC2-DMPE in dry DMSO ABSC1 stock (400×): 200 mM ABSC1 in water

Assay Protocol

Insert or use electrodes into each well to be assayed.

Use the current-controlled amplifier to deliver stimulation wave pulses for 3 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\,nm} - background_{460\,nm})}{(intensity_{580\,nm} - background_{580\,nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R - P}{N - P} * 100.$$

where R is the ratio response of the test compound.

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 µm in diameter) have been visually identified and probed with fine tip glass electrodes connected to an amplifier (Axon Instruments). The "voltage clamp" mode has been used to assess the compound's IC$_{50}$ holding the cells at −60 mV. In addition, the "current clamp" mode has been employed to test the efficacy of the compounds in blocking action potential generation in response to current injections. The results of these experiments have contributed to the definition of the efficacy profile of the compounds.

Voltage-Clamp Assay in DRG Neurons

TTX-resistant sodium currents were recorded from DRG somata using the whole-cell variation of the patch clamp technique. Recordings were made at room temperature (~22° C.) with thick walled borosilicate glass electrodes (WPI; resistance 3-4 MΩ using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +10 mV once every 60 seconds. Blocking effects were allowed to plateau before proceeding to the next test concentration.

Solutions

Intracellular solution (in mM): Cs-F (130), NaCl (10), MgCl$_2$ (1), EGTA (1.5), CaCl$_2$ (0.1), HEPES (10), glucose (2), pH=7.42, 290 mOsm.

Extracellular solution (in mM): NaCl (138), CaCl2 (1.26), KCl (5.33), KH$_2$PO$_4$ (0.44), MgCl$_2$ (0.5), MgSO$_4$ (0.41), NaHCO$_3$ (4), Na$_2$HPO4 (0.3), glucose (5.6), HEPES (10), CdCl$_2$ (0.4), NiCl$_2$ (0.1), TTX (0.25×10$^{-3}$).

Current-Clamp Assay for NaV channel Inhibition Activity of Compounds

Cells were current-clamped in whole-cell configuration with a Multiplamp 700A amplifier (Axon Inst). Borosilicate pipettes (4-5 Mohm) were filled with (in mM):150 K-gluconate, 10 NaCl, 0.1 EGTA, 10 Hepes, 2 MgCl$_2$, (buffered to pH 7.34 with KOH). Cells were bathed in (in mM): 140 NaCl, 3 KCl, 1 MgCl$_2$, 1 CaCl$_2$, and 10 Hepes). Pipette potential was zeroed before seal formation; liquid junction potentials were not corrected during acquisition. Recordings were made at room temperature.

The exemplified compounds of Table 2 herein are active against one or more sodium channels as measured using the assays described hereinabove as presented in Table 4.

TABLE 4

| IC50/EC50 Bins: +++ <= 2.0 < ++ <= 5.0 < + | |
|---|---|
| Cmpd. No. | Binned IC50 |
| 1 | +++ |
| 2 | +++ |
| 3 | +++ |
| 4 | +++ |
| 5 | +++ |
| 6 | +++ |

Many modifications and variations of the embodiments described herein may be made without departing from the scope, as is apparent to those skilled in the art. The specific embodiments described herein are offered by way of example only.

We claim:

1. A method of treating or lessening the severity in a subject of acute, chronic, neuropathic, or inflammatory pain, visceral pain, osteoarthritis pain, radicular pain, back pain, head or neck pain, severe or intractable pain, nociceptive pain, breakthrough pain, postsurgical pain, or cancer pain, comprising administering an effective amount of a compound according to formula I:

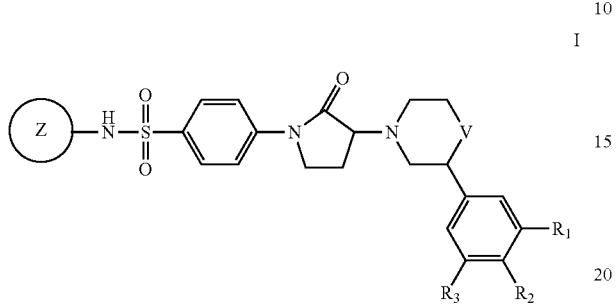

I or a pharmaceutically acceptable salt thereof,
wherein, independently for each occurrence:
ring Z is a thiazole or thiadiazole optionally substituted with 0-2 occurrences of R;
V is O or S; and
R, $R_1$, $R_2$, and $R_3$ are hydrogen, C1-C6 aliphatic, aryl, C3-C8 cycloaliphatic, halo, CN, $NO_2$, $CF_3$, $OCF_3$, OH, $NH_2$, NH(C1-C6 aliphatic), N(C1-C6 aliphatic)$_2$, COOH, COO(C1-C6 aliphatic), O(C1-C6 aliphatic), $CHF_2$, or $CH_2F$;
or a pharmaceutically acceptable composition comprising a compound of formula I to said subject in need thereof.

2. The method according to claim 1, wherein said method is used for treating or lessening the severity of femur cancer pain; non-malignant chronic bone pain; neuropathic low back pain; neuropathic low back pain; myofascial pain syndrome; temporomandibular joint pain; chronic visceral pain, IBS pain; chronic and acute headache pain; chronic and acute neuropathic pain, chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; injury/exercise pain; acute visceral pain, abdominal pain; chest pain, cardiac pain; pelvic pain, renal colic pain, acute obstetric pain, labor pain; cesarean section pain; burn and trauma pain; acute intermittent pain, acute herpes zoster pain; breakthrough pain; orofacial pain, sinusitis pain, dental pain; multiple sclerosis (MS) pain; leprosy pain; Behcet's disease pain; phlebitic pain; Guillain-Barre pain; erythromelalgia pain; Fabry's disease pain; painful bladder syndrome; complex regional pain syndrome (CRPS), or angina-induced pain.

3. The method of claim 1, wherein Z is

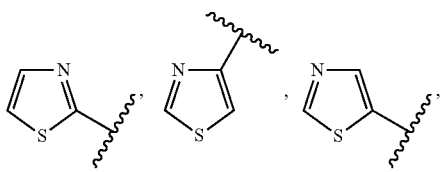

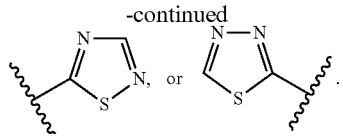

4. The method of claim 1, wherein Z is

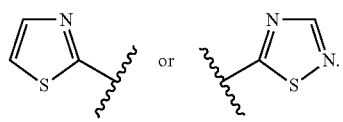 [SMILES: *c1nccs1 ; *c1ncns1]

5. The method of claim 1, wherein $R_1$, $R_2$, and $R_3$ are hydrogen, C1-C6 aliphatic, halo, or $CF_3$.

6. The method of claim 1, wherein Z is

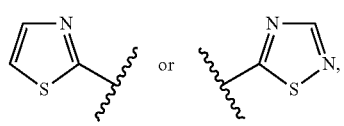

and $R_1$, $R_2$, and $R_3$ are hydrogen, C1-C6 aliphatic, halo, or $CF_3$.

7. The method of claim 1, wherein V is O.

8. The method of claim 1, wherein at least two of $R_1$, $R_2$, or $R_3$ are halo.

9. The method of claim 1, wherein $R_1$, $R_2$, and $R_3$ are H or Cl.

10. The method of claim 1, wherein Z is

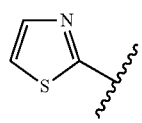

and V is O.

11. The method of claim 1, wherein Z is

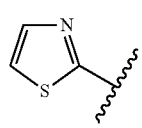

and $R_1$ and $R_3$ are Cl.

12. The method of claim 1, wherein Z is

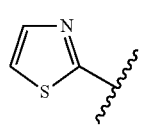 [SMILES: *c1nccs1]

and $R_1$ and $R_2$ are Cl.

13. The method of claim 1, wherein the compound is of formula Ia:

Ia

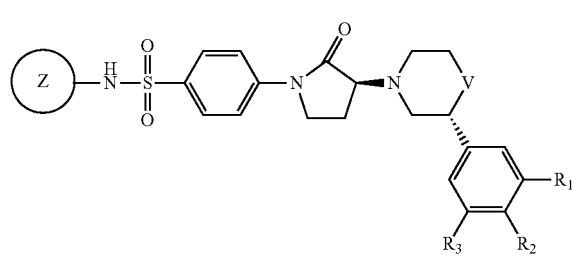

Ib

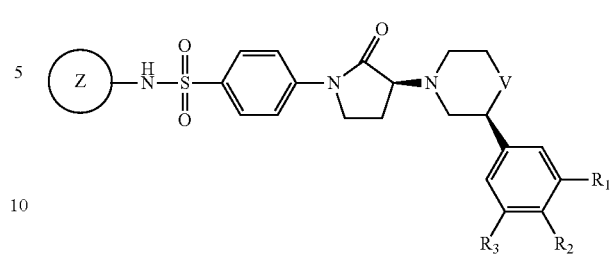

or a pharmaceutically acceptable salt thereof,
wherein, independently for each occurrence:
ring Z is a thiazole or thiadiazole optionally substituted with 0-2 occurrences of R;
V is O or S; and
R, $R_1$, $R_2$, and $R_3$ are hydrogen, C1-C6 aliphatic, aryl, C3-C8 cycloaliphatic, halo, CN, $NO_2$, $CF_3$, $OCF_3$, OH, $NH_2$, NH(C1-C6 aliphatic), N(C1-C6 aliphatic)$_2$, COOH, COO(C1-C6 aliphatic), O(C1-C6 aliphatic), $CHF_2$, or $CH_2F$.

14. The method of claim 13, wherein Z is

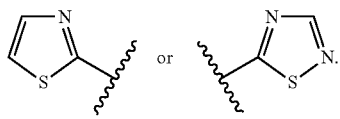

15. The method of claim 13, wherein $R_1$, $R_2$, and $R_3$ are hydrogen, C1-C6 aliphatic, halo, or $CF_3$.
16. The method of claim 13, wherein V is O.
17. The method of claim 13, wherein at least two of $R_1$, $R_2$, or $R_3$ are halo.
18. The method of claim 13, wherein $R_1$, $R_2$, and $R_3$ are H or Cl.
19. The method of claim 13, wherein the compound is selected from the group consisting of

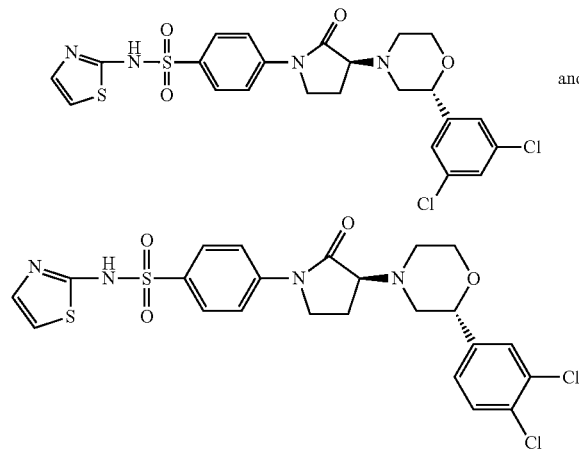

20. The method of claim 1, wherein the compound is of formula Ib:

or a pharmaceutically acceptable salt thereof,
wherein, independently for each occurrence:
ring Z is a thiazole or thiadiazole optionally substituted with 0-2 occurrences of R;
V is O or S; and
R, $R_1$, $R_2$, and $R_3$ are hydrogen, C1-C6 aliphatic, aryl, C3-C8 cycloaliphatic, halo, CN, $NO_2$, $CF_3$, $OCF_3$, OH, $NH_2$, NH(C1-C6 aliphatic), N(C1-C6 aliphatic)$_2$, COOH, COO(C1-C6 aliphatic), O(C1-C6 aliphatic), $CHF_2$, or $CH_2F$.

21. The method of claim 20, wherein Z is

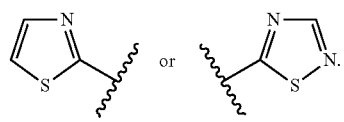 [SMILES: *c1nccs1 ; *c1ncns1]

22. The method of claim 20, wherein $R_1$, $R_2$, and $R_3$ are hydrogen, C1-C6 aliphatic, halo, or $CF_3$.
23. The method of claim 20, wherein V is O.
24. The method of claim 20, wherein at least two of $R_1$, $R_2$, or $R_3$ are halo.
25. The method of claim 20, wherein $R_1$, $R_2$, and $R_3$ are H or Cl.
26. The method of claim 20, wherein the compound is selected from the group consisting of

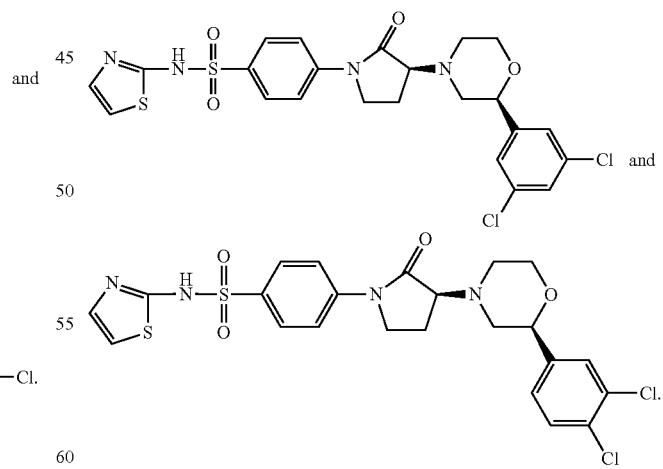

* * * * *